US012767972B2

(12) United States Patent
Hull et al.

(10) Patent No.: US 12,767,972 B2
(45) Date of Patent: Oct. 20, 2026

(54) METHOD TO SCREEN COMPOUNDS FOR ANTIFUNGAL ACTIVITY AND PHARMACEUTICAL COMPOSITIONS AND METHODS TO TREAT FUNGAL DISEASES BY INHIBITING SPORE GERMINATION

(71) Applicant: Wisconsin Alumni Research Foundation, Madison, WI (US)

(72) Inventors: Christina Marie Hull, Middleton, WI (US); Mingwei Huang, Madison, WI (US); Sebastien Claude Ortiz, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 86 days.

(21) Appl. No.: 18/631,396

(22) Filed: Apr. 10, 2024

(65) Prior Publication Data

US 2024/0247299 A1 Jul. 25, 2024

Related U.S. Application Data

(63) Continuation of application No. 16/369,939, filed on Mar. 29, 2019, now Pat. No. 11,981,953.

(60) Provisional application No. 62/649,802, filed on Mar. 29, 2018.

(51) Int. Cl.

| | |
|---|---|
| ***C12Q 1/18*** | (2006.01) |
| ***A01N 33/10*** | (2006.01) |
| ***A01N 37/44*** | (2006.01) |
| ***A01N 41/12*** | (2006.01) |
| ***A01N 47/40*** | (2006.01) |
| ***A61K 31/137*** | (2006.01) |
| ***A61K 31/145*** | (2006.01) |
| ***A61K 31/155*** | (2006.01) |
| ***A61K 31/24*** | (2006.01) |
| ***A61P 31/10*** | (2006.01) |
| ***C12Q 1/66*** | (2006.01) |

(52) U.S. Cl.

CPC ............... *C12Q 1/18* (2013.01); *A01N 33/10* (2013.01); *A01N 37/44* (2013.01); *A01N 41/12* (2013.01); *A01N 47/40* (2013.01); *A61K 31/137* (2013.01); *A61K 31/145* (2013.01); *A61K 31/155* (2013.01); *A61K 31/24* (2013.01); *A61P 31/10* (2018.01); *C12Q 1/66* (2013.01); *G01N 2333/375* (2013.01)

(58) Field of Classification Search

None

See application file for complete search history.

(56) References Cited

U.S. PATENT DOCUMENTS

2005/0119306 A1 6/2005 Trail

FOREIGN PATENT DOCUMENTS

| | | | | | |
|---|---|---|---|---|---|
| EP | 0174477 A1 | | 3/1986 | | |
| GB | 2208598 A | * | 4/1989 | ............. A61P 31/04 | |
| WO | AWO 0029610 A1 | | 5/2000 | | |

OTHER PUBLICATIONS

Hughes ("Comparison of pentamidine isethionate and trimethoprim-sulfamethoxazole in the treatment of Pneumocystis carinii pneumonia" The Journal of Pediatrics, vol. 92, Issue 2, 1978, 285-291, abstract provided). (Year: 1978).*

Abhyankar ("Spore proteomics: the past, present and the future" FEMS Microbiol Lett, 2014, 358, 137-144. (Year: 2014).

Ganendren, R., Widmer, F., Singhal, V., Wilson, C., Sorrell, T., & Wright, L. (2004). In vitro antifungal activities of inhibitors of phospholipases from the fungal pathogen Cryptococcus neoformans. Antimicrobial agents and chemotherapy, 48(5), 1561-1569.

Walsh, G. (2018). Biopharmaceutical benchmarks 2018. Nature biotechnology, 36(12), 1136-1145.

Zhao, (Cytological adn proteomic analyses of horsetail (*Equisetum arvense* L.) spore germination), Frontiers in Plant Science, 2015, 17:44, 1-20) (Year: 2015).

Alspaugh JA, Perfect JR, Heitman J. (1998) "Signal transduction pathways regulating differentiation and pathogenicity of *Cryptococcus neoformans," Fungal Genet Biol.* 25:1-14 (pmid:9806801).

Barkal LJ, Walsh NM, Botts MR, Beebe DJ, Hull CM. 2016. Leveraging a high resolution microfluidic assay reveals insights into pathogenic fun-gal spore germination. Integr Biol 8:603-615. https://doi.org/10.1039/c6ib00012f.

Botts et al., Isolation and characterization of Cryptococcus neoformans spores reveal a critical role for capsule biosynthesis genes in spore biogenesis. Eukaryotic Cell. Apr. 2009; 8(4):595-605. doi: 10.1128/EC.00352-08.

(Continued)

*Primary Examiner* — Robert J Yamasaki
*Assistant Examiner* — Charles Zoltan Constantine
(74) *Attorney, Agent, or Firm* — Joseph T. Leone; Yanjun Ma; De Witt LLP

(57) ABSTRACT

A method of testing compounds for activity to inhibit germination of spores. The method includes the steps of (a) providing bacterial, fungal, or plant spores transformed to contain and express a detectable marker, wherein the marker when expressed, is operationally linked to a spore-specific or yeast-specific protein, in a medium and under environmental conditions in which the spores will germinate, and measuring a first signal output generated by the marker prior to the spores initiating germination; (b) contacting the spores of step (a) with a compound whose activity to inhibit germination of spores is to be measured; (c) incubating the spores of step (b) under environmental conditions and for a time wherein spores not treated with the compound will germinate; and (d) determining extent of germination of the spores by measuring a second signal output generated by the marker, wherein a difference between the first signal output and the second signal output is proportional to the extent of germination of the spores. Also described are compositions of matter for inhibiting spore germination in vitro and in vivo.

5 Claims, 13 Drawing Sheets

Specification includes a Sequence Listing.

(56) References Cited

OTHER PUBLICATIONS

Davidson RC, Blankenship JR, Kraus PR, De J Berrios M, Hull CM, D'Souza C, et al., A PCR-based strategy to generate integrative targeting alleles with large regions of homology. *Microbiology*. 2002; 148: 2607-2615. PMID: 12177355.

Giles SS, Dagenais TRT, Botts MR, Keller NP, Hull CM (2009) "Elucidating the pathogenesis of spores from the human fungal pathogen *Cryptococcus neoformans,*" *Infect Immun* 77(8):3491-3500 (pmid:19451235).

Handbook of Pharmaceutical Salts, Properties, Selection, and Use, P.H. Stahl and C.G. Wermuch, Eds., © 2008, Wiley-VCH (Zurich, Switzerland), ISBN: 978-3-90639-058-1 (Book—Copy Not Provided).

Huang M, Hebert AS, Coon JJ, Hull CM, (2015) Protein Composition of Infectious Spores Reveals Novel Sexual Development and Germination Factors in *Cryptococcus*, PLoS Genet 11(8): e 1005490 (https://doi.org/10.1371/journal.pgen.1005490).

Kwon-Chung KJ, Edman JC, Wickes BL, (1992) "Genetic association of mating types and virulence in *Cryptococcus neoformans,*" *Infect Immun.* 60:602-605 (pmid:1730495).

Moore TD, Edman JC, (1993) "The alpha-mating type locus of *Cryptococcus neoformans* contains a peptide pheromone gene," *Mol Cell Biol.* 13:1962-1970 (pmid:8441425).

Rajasingjam R, Smith RM, Park BJ, Jarvis JM, Govender N, Chiller TM, Denning DW, Loyse A, Boulware DR, (2017) "Global burden of disease of HIV-associated cryptococcal meningitis: and updated analysis" *Lancet Infectious Disease* 17: 873-881 (pmid:2848341).

Sherman F, Fink GR, Hicks JB. Laboratory course manual for methods in yeast genetics. Cold Spring Harbor Laboratory; 1987 (Book—Copy Not Provided).

Sherman F. (2002) "Getting started with yeast," *Methods Enzymol.* 350:3-41(pmid:12073320).

Toffaletti DL, Rude TH, Johnston SA, Durack DT, Perfect JR. Gene transfer in Cryptococcus neoformans by use of biolistic delivery of DNA. *J Bacteriol.* 1993; 175: 1405-1411. PMID: 8444802.

Velagapudi R, Hsueh Y-P, Geunes-Boyer S, Wright JR, Heitman J, (2009) "Spores as infectious propagules of *Cryptococcus neoformans,*" *Infect Immun.* 77:4345-4355 (pmid:19620339).

Walsh NM, Wuthrich M, Wang H, Klein B, and Hull CM. 2017. Characterization of C-type lectins reveals an unexpectedly limited interaction between *Cryptococcus neoformans* spores and Dectin-1. *PloS One* 12(3):e0173866.

* cited by examiner

METHOD TO SCREEN COMPOUNDS FOR ANTIFUNGAL ACTIVITY AND PHARMACEUTICAL COMPOSITIONS AND METHODS TO TREAT FUNGAL DISEASES BY INHIBITING SPORE GERMINATION

CROSS-REFERENCE TO RELATED APPLICATIONS

The present application is a continuation of co-pending U.S. application Ser. No. 16/369,939, filed Mar. 29, 2019, which claims benefit of priority to U.S. provisional application Ser. No. 62/649,802, filed Mar. 29, 2018, both of which are incorporated herein by reference.

FEDERAL FUNDING STATEMENT

This invention was made with government support under AI089370 and AI137409 awarded by the National Institutes of Health. The government has certain rights in the invention.

SEQUENCE LISTING

The instant application contains a Sequence Listing which has been submitted in an XML file with the USPTO through Patent Center and is hereby incorporated by reference in its entirety. The Sequence Listing XML, created on Mar. 26, 2024, is named "SEQ_LIST-09824507-P180117US03.xml" and is 124,578 bytes in size.

BACKGROUND

Spores are an essential cell type required for long-term survival across diverse organisms and are a hallmark of fungal reproduction, persistence, and dispersal. Among human fungal pathogens, spores are presumed infectious particles, but relatively little is known about this robust cell type. Sporulation enables a relative quiescence—a type of hibernation—that contributes to the survival of fungi. However, sporulation also requires a transition back into a vegetative form so that the fungi can replicate—i.e., germination. Germination, despite its central importance in fungal reproduction and pathology in plants and animals, is not well understood.

Spores are a particularly successful cell type used by many microorganisms, including bacteria, fungi, and protozoa to survive unsuitable growth conditions and/or to disperse to new environments. Among eukaryotes, some of the most environmentally resistant spores are those of fungi, and much of our current understanding of spores comes from studies in model fungi such as *Saccharomyces cerevisiae* and *Aspergillus nidulans*. There are two general categories of fungal spores—sexual and asexual, and both forms occur across diverse fungal species via myriad developmental strategies. For example, in the budding yeast *S. cerevisiae* sexual spores are formed when yeast diploids are subject to nitrogen starvation and a non-fermentable carbon source, resulting in four haploid ascospores; *S. cerevisiae* does not produce asexual spores. In contrast, the filamentous fungus *Aspergillus nidulans* produces both asexual and sexual spores via the development of multicellular fruiting structures with thousands of spores per structure. In all instances, however, spores are adapted for general survivability.

As a consequence, fungal spores share three basic characteristics: First, mature spores are relatively metabolically quiescent, allowing them to remain dormant for long periods of time under sub-optimal growth conditions (e.g. in the absence of nutrients). Second, spores are resistant to environmental stresses, such as high temperatures, desiccation, and UV radiation, thus facilitating long-term survival and/or dispersal across great distances. Third, upon encountering growth-promoting environments, spores rapidly escape quiescence and germinate to resume vegetative growth. As a result, fungi are ubiquitous across all ecosystems on earth.

Spore-producing fungi commonly generate spores with thick, protective coats and robust stress resistance. Spores respond to different environmental signals to initiate germination, depending on their adapted niches. For example, spores of *S. cerevisiae* germinate readily in response to the presence of a fermentable carbon source. In contrast, spores of *Talaromyces macrosporus* require nutrients and a rigorous external trigger of very high temperature or pressure. These triggers generally result in responses such as water uptake, cell wall remodeling, and activation of nutrient metabolism and protein synthesis, leading to active fungal growth.

The transition from dormant particle to actively growing cell is particularly important because fungal survival cannot occur in the absence of the ability to germinate when (and only when) appropriate for vegetative growth. Environmental fungi are well adapted to their niches, and interestingly, these adaptations have led to a handful of fungi with the ability to cause life-threatening diseases in humans. *Histoplasma capsulatum, Blastomyces dermatitidis, Aspergillus fumigatus, Coccidioides immitis, Sporothrix schenkii, Penicillium marneffei*, and *Cryptococcus neoformans* are the most common environmental fungi that can cause disease in humans. The general route of infection is by inhaling cells from environmental sources. Spores (sexual or asexual, depending on the fungus) are the most likely infectious particles for all of these pathogens; however, very little is known about their basic spore biology, making the development of disease prevention and treatment strategies challenging.

Among human fungal pathogens, the most common cause of fatal fungal disease (and a well-developed model for study) is *Cryptococcus neoformans*, a primarily opportunistic pathogenic yeast that causes meningoencephalitis. People with AIDS are particularly susceptible, and there are an over 200,000 cases and nearly as many deaths annually worldwide from cryptococcosis. Rajasingjam R, Smith R M, Park B J, Jarvis J M, Govender N, Chiller T M, Denning D W, Loyse A, Boulware D R (2017) "Global burden of disease of HIV-associated cryptococcal meningitis: and updated analysis" *Lancet Infectious Disease* 17: 873-881 (pmid: 2848341). *C. neoformans* is ubiquitous in the environment, and inhalation of aerosolized spores and/or yeast is the most common route of infection of humans. Under laboratory conditions, spores are produced through sexual development between haploid yeast of opposite mating types (a and $\alpha$) or by $\alpha$ fruiting. In response to specific environmental conditions, cells form filaments and fruiting bodies (basidia) from which haploid, recombinant spores bud in chains.

Spores of *C. neoformans* exhibit the fundamental properties of most fungal spores, such as stability in the absence of nutrients and resistance to a variety of environmental stresses, including high temperature, desiccation, and oxidative stress. These spores have also been shown to germinate efficiently and synchronously in response to nutrients, and they germinate and cause disease in a mouse inhalation model of infection. See Velagapudi R, Hsuch Y-P, Geunes-Boyer S, Wright J R, Heitman J (2009) "Spores as infectious propagules of *Cryptococcus neoformans*," *Infect Immun.* 77:4345-4355 (pmid: 19620339) and Giles S S, Dagenais T R T, Botts M R, Keller N P, Hull C M (2009) "Elucidating the pathogenesis of spores from the human fungal pathogen *Cryptococcus neoformans*," *Infect Immun* 77:3491-3500 (pmid: 19451235). These findings indicate that *C. neoformans* spores harbor intrinsic properties that facilitate survival in the environment, maintain spore viability and stability, and initiate germination in response to external signals, including those of a mammalian host.

Current antifungal therapeutics are relatively limited because of high toxicity or insufficient efficacy. These issues arise because, unlike bacteria, fungi are eukaryotes. Thus, fungi are far more similar (metabolically and biochemically) to plants and animals than are bacteria. In short, compounds that interfere with fungal biology or are toxic to fungi, tend also to interfere with or be toxic to humans and animals.

A comparatively small number of antifungal compounds are approved for human, veterinary, and agricultural use in the United States. Focusing on antifungal drugs approved for use in humans, the gold standard by which all other antifungal pharmaceuticals are measured in terms of systemic antifungal activity is the polyene amphotericin B, first marketed in 1955. It is widely used to treat life-threatening fungal infections such as invasive mucormycosis, cryptococcal meningitis, aspergillosis, and candidiasis. While highly effective against fungi, amphotericin B itself has a slew of well-known and potentially life-threatening side effects. When administered intravenously, amphotericin B typically induces a debilitating set of symptoms, including high fever, shaking chills, hypotension, anorexia, nausea, vomiting, headache, dyspnea and tachypnea, drowsiness, and generalized weakness. Kidney damage is a commonly reported side effect. As a result, amphotericin B is administered with very close monitoring of the patient by healthcare professionals.

Other antifungal compounds approved for use in humans include imidazoles (e.g., miconazole), triazoles (e.g., fluconazole), and thiazole antifungals (e.g., abafungin). Most of these types of antifungal compounds, however, are used topically, rather than systemically. They are much less toxic that amphotericin B, but not as efficacious.

Echinocandins are a much newer class of systemic antifungal compounds approved for use in humans. The echinocandins are macrocyclic lipopeptides. Their structure is characterized by (typically) a 6-mer macrocyclic peptoid moiety bonded to a long (e.g., >C10) hydrocarbon tail. Echinocandins inhibit the synthesis of glucan in the cell wall of fungi via noncompetitive inhibition of the enzyme 1,3-β glucan synthase. In this sense, they exert a pharmacological activity against fungi that is analogous to the pharmacological activity of beta-lactam antibiotics against bacteria. Echinocandins are also far less toxic than amphotericin B, but again, not as effective.

Thus, there remains a long-felt and unmet need for a method to test new and existing compounds for their ability to inhibit fungal growth.

SUMMARY

While vegetative fungi are similar metabolically and biochemically to other eukaryotic cells, fungi also sporulate and germinate. Thus, chemical inhibitors of fungal germination are potentially highly useful compounds in antifungal compositions (i.e., human and veterinary pharmaceuticals, topical and systemic pharmaceuticals, and agricultural and industrial fungicides). Thus, disclosed herein is a fluorescence-based quantitative germination assay suitable for high throughput screening. Using the subject germination assay, a screening of a 75,000-compound library yielded 108 germination-inhibiting compounds. Some of these compounds exhibited specific activity to inhibit germination of *Cryptococcus* spores (as contrasted to inhibiting vegetative cell growth). This indicates that germination itself is an effective target in developing antifungal drugs for prophylactic use in at-risk patients.

Thus, disclosed herein is a method of testing compounds for activity to inhibit germination of spores. The method comprises providing bacterial, fungal, or plant spores transformed to contain and express a detectable marker, wherein the marker is operationally linked to a spore-specific or yeast-specific protein, in a medium and under environmental conditions in which the spores will germinate, and measuring a first signal output generated by the marker prior to the spores initiating germination. The spores are then contacted with a compound whose activity to inhibit germination of spores is to be measured. The spores are then incubated under environmental conditions and for a time wherein spores not treated with the compound will germinate. The extent of germination of the spores is determined by measuring a second signal output generated by the marker, wherein a difference between the first signal output and the second signal output is proportional to the extent of germination of the spores.

In certain versions of the method, the marker is operationally linked to a spore-specific protein selected from the group consisting of XP_567740.1 (SEQ. ID. NO: 2), XP_566791.1 (SEQ. ID. NO: 4), XP_570303.1 (SEQ. ID. NO: 6), XP_571089.1 (SEQ. ID. NO: 8), XP_571997.1 (SEQ. ID. NO: 10), XP_569295.1 (SEQ. ID. NO: 12), XP_569173.1 (SEQ. ID. NO: 14), XP_569068.1 (SEQ. ID. NO: 16), XP_569336.1 (SEQ. ID. NO: 18), XP_567136.1 (SEQ. ID. NO: 20), XP_568990.1 (SEQ. ID. NO: 22), XP_570610.1 (SEQ. ID. NO: 24), XP_571921.1 (SEQ. ID. NO: 26), XP_572925.1 (SEQ. ID. NO: 28), XP_570796.1 (SEQ. ID. NO: 30), XP_571548.1 (SEQ. ID. NO: 32), XP_570447.1 (SEQ. ID. NO: 34), and XP_571343.1 (SEQ. ID. NO: 36).

Another version of the method comprises the steps described previously, and further comprising plotting the area and aspect ratio of the spores and any germinated cells after the incubation of step (c). Because spores tend to be smaller and have a more oblong aspect ratio than do germinated, vegetative cells, the extent of germination can be determined by measuring the distribution of the cells' area versus aspect ratio. Again, in this version of the method, the marker, if present, is operationally linked to a spore-specific protein selected from the group consisting of XP_567740.1 (SEQ. ID. NO: 2), XP_566791.1 (SEQ. ID. NO: 4), XP_570303.1 (SEQ. ID. NO: 6), XP_571089.1 (SEQ. ID. NO: 8), XP_571997.1 (SEQ. ID. NO: 10), XP_569295.1 (SEQ. ID. NO: 12), XP_569173.1 (SEQ. ID. NO: 14), XP_569068.1 (SEQ. ID. NO: 16), XP_569336.1 (SEQ. ID. NO: 18), XP_567136.1 (SEQ. ID. NO: 20), XP_568990.1 (SEQ. ID. NO: 22), XP_570610.1 (SEQ. ID. NO: 24), XP_571921.1 (SEQ. ID. NO: 26), XP_572925.1 (SEQ. ID. NO: 28), XP_570796.1 (SEQ. ID. NO: 30), XP_571548.1 (SEQ. ID. NO: 32), XP_570447.1 (SEQ. ID. NO: 34), and XP_571343.1 (SEQ. ID. NO: 36), Also disclosed herein are antifungal compositions and method of using them as topical and systemic fungicides for industrial, agricultural, and pharmaceutical uses. Disclosed herein is a composition of matter for inhibiting germination of fungal spores, the composition comprising a spore germination-inhibiting concentration of a compound selected from the group consisting of

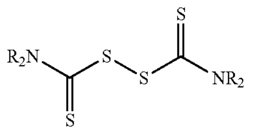

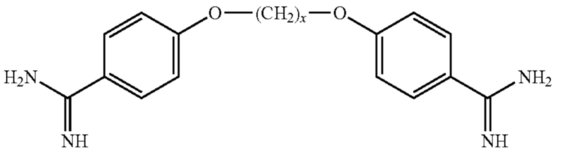

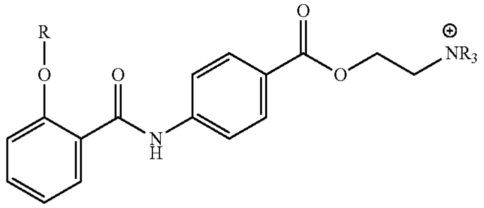

and

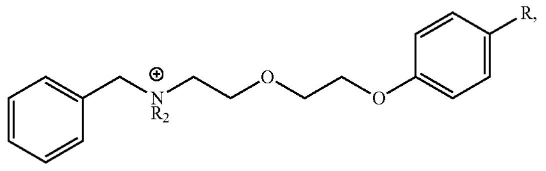

and salts thereof, in combination with a vehicle.

Also disclosed herein is a pharmaceutical composition for inhibiting fungal infection in mammals (as well as the corresponding method of inhibiting topical or systemic fungal infections in mammals, including humans), the composition comprising a spore germination-inhibiting amount of a compound selected from the group consisting of:

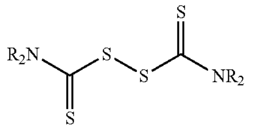

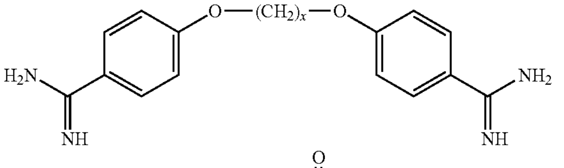

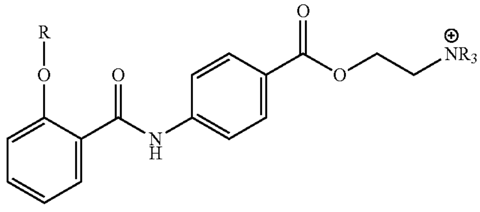

and

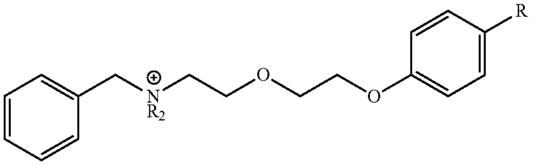

wherein R is linear or branched $C_{1-12}$ alkyl and "x" is an integer of from 1 to 12, and salts thereof, in combination with a pharmaceutically suitable vehicle.

BRIEF DESCRIPTION OF THE DRAWINGS

FIG. 8A is a graph showing lung colony-forming units quantified for each mouse infected with JEC20×JEC21 yeast. The test group of mice were treated with 4 mg/kg/day pentamidine; the control group of mice were treated with 1×PBS; * $p<0.05$ for two-tailed paired t-test.

FIG. 8B is a graph depicting lung colony-forming units quantified for each mouse infected with JEC20×JEC21. Again, the test mice were treated with 4 mg/kg/day pentamidine; the control mice were given 1×PBS; ** $p<0.01$ for two-tailed paired t-test.

FIG. 9 depicts lung colony-forming units quantified for each mouse infected with JEC20×JEC21 spores. The test group of mice were treated with 4 mg/kg/day pentamidine; the control group of mice were treated with 1×PBS. ** $p<0.01$ for two-tailed paired t-test. See Examples for complete details.

DETAILED DESCRIPTION

Abbreviations and Definitions

Figure 1:
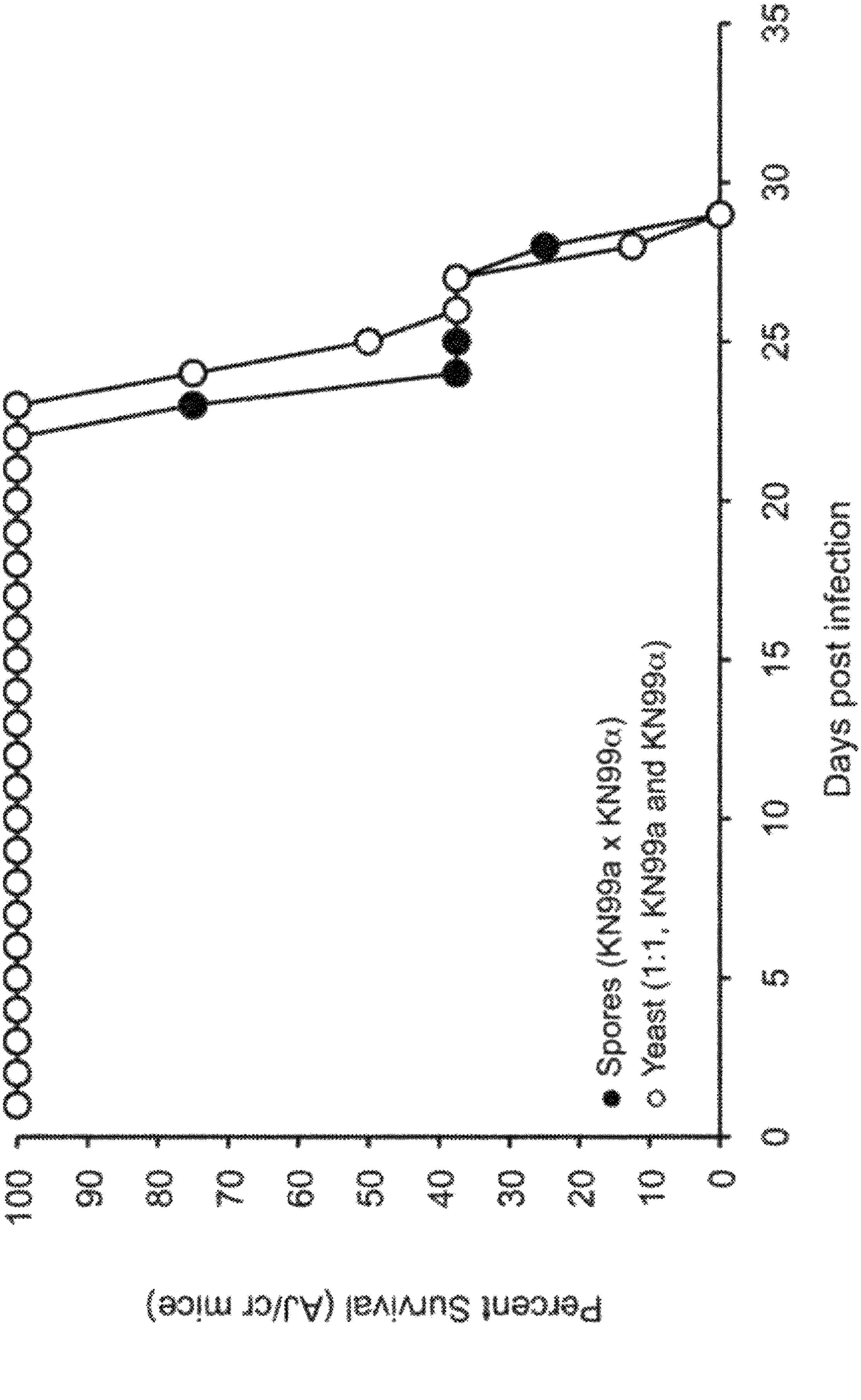
FIG. 1 is a graph showing that *C. neoformans* var. *grubii* spores are pathogenic in a murine model of cryptococcosis. Groups of eight AJ/Cr mice were infected with *C. neoformans* var. *grubii* spores ($10^5$) or yeast ($10^5$) via intranasal inhalation. See Giles et al. *Infect. Immun.* 2009, 77(8):3491. Time post-infection (in days) is shown in the X-axis; percent of surviving mice is shown on the Y-axis.

The term "pharmaceutically-suitable salt" refers to any acid or base addition salt whose counter-ions are non-toxic to the patient in pharmaceutical doses of the salts, so that the beneficial inhibitory effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, gentisates, isethionates, di-p-toluoyltartrates, methane sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like. See, for example, "Handbook of Pharmaceutical Salts, Properties, Selection, and Use," P. H. Stahl and C. G. Wermuch, Eds., ©2008, Wiley-VCH (Zurich, Switzerland), ISBN: 978-3-90639-058-1.

"Spore-specific molecule" refers to any molecule, moiety, or protein that is highly overrepresented in abundance in spores relative to yeast. Conversely, "Yeast-specific molecule" refers to any molecule, moiety, or protein that is highly overrepresented in abundance in yeast relative to yeast. Specifically included in the terms are the proteins identified in Huang M, Hebert A S, Coon J J, Hull C M (2015) "Protein Composition of Infectious Spores Reveals Novel Sexual Development and Germination Factors in *Cryptococcus*, PLoS Genet 11(8): e1005490 (https://doi.org/10.1371/journal.pgen.1005490). These spore-specific proteins were repeatedly identified by mass spectrometry in spore samples and never in yeast samples and are encoded by the following genes:

TABLE 1

Genes encoding spore-specific proteins.

| Gene | JEC21 ID | Predicted functions/domains | Deletion phenotype(s) |
|---|---|---|---|
| | | Group 1: Replication and Chromosome Biology | |
| TOP1 | CNI03280 | topoisomerase1 | sporulation defects |
| IRR1 | CNA07890 | nuclear cohesion complex component | inviable |
| | | Group 2: Transcription and Splicing | |
| RSC9 | CNB00580 | chromatin remodeling complex component | cell fusion defect |
| DST1 | CNF01160 | general transcription elongation factor TFIIS | sporulation defect |
| PRP31 | CNB05520 | U4/U6-U5 snRNP complex component | inviable |
| PRP11 | CND02290 | SF3a splicing factor complex component | inviable |
| | | Group 3: Cellular Transport | |
| BCH1 | CNG02530 | specialized cargo export from Golgi | filamentation defect |
| SFH5 | CNE04320 | non-classical phosphatidylinositol transfer protein | no phenotype |

TABLE 1-continued

| Genes encoding spore-specific proteins. | | | |
|---|---|---|---|
| Gene | JEC21 ID | Predicted functions/domains | Deletion phenotype(s) |
| DDI1 | CNC00460 | vSNARE binding protein | sporulation defect |
| EMC3 | CNF02470 | protein folding in the ER | decreased spore yield |
| | | Group 4: Carbohydrate Metabolism | |
| GRE202 | CNG01830 | D-lactaldehyde dehydrogenase | decreased spore yield |
| ISP1[a] | CNB02490 | conserved in fungi/short chain dehydrogenase | filamentation defect |
| ISP3 | CND04560 | conserved in fungi/mannose-6-phosphate isomerase | no phenotype |
| ISP4 | CNK01510 | conserved in fungi/glycosyl hydrolase | no phenotype |
| | | Group 5: Proteins of Unknown Function | |
| ISP2 | CNE01730 | *Cryptococcus*-specific/no conserved domains | increased sporulation; slow germination |
| ISP5 | CNB04980 | conserved in fungi/ferritin-like superfamily domain | no phenotype |
| ISP6 | CNA04360 | *Cryptococcus*-specific/transmembrane domain | no phenotype |
| ISP7 | CND00650 | *Cryptococcus*-specific/no conserved domains | no phenotype |

[a]Genes encoding proteins with no obvious homologs were named ISP for identified Spore Protein.
dDoi: 10.1371/journal.pgen. 1005490.t003

The spore-specific genes and proteins identified in the above table have the nucleotide and amino acid sequences and protein ID's shown in the Sequence Listing at SEQ. ID. NOS 1-36.

Yeast-specific proteins include, but are not limited to, CND06170, XP_570090.1 (SEQ. ID. NOS. 37 and 38); CND01050, XP_570422.1 (SEQ. ID. NOS. 39 and 40); CNH01340, XP_572322.1 (SEQ. ID. NOS. 41 and 42); CNN02360, XP_568723.1 (SEQ. ID. NOS. 43 and 44); CNB01440, XP_568816.1 (SEQ. ID. NOS. 45 and 46); CNG00410, XP_571739.1 (SEQ. ID. NOS. 47 and 48); CNH02740, XP_572447.1 (SEQ. ID. NOS. 49 and 50); CNJ01750, XP_567350.1 (SEQ. ID. NOS. 51 and 52); CNI02030, XP_572658.1 (SEQ. ID. NOS. 53 and 54); CNB05750, XP_569316.1 (SEQ. ID. NOS. 55 and 56); CNI03560, XP_572607.1 (SEQ. ID. NOS. 57 and 58); CNK01820, XP_567661.1 (SEQ. ID. NOS. 59 and 60); CNI00900, XP_572819.1 (SEQ. ID. NOS. 61 and 62); CNK02880, XP_567883.1 (SEQ. ID. NOS. 63 and 64); CNF00610, XP_571239.1 (SEQ. ID. NOS. 65 and 66); and CNI00870, XP_572850.1 (SEQ. ID. NOS. 66 and 67). These yeast-specific proteins, which are shown in the Sequence Listing, can be utilized as markers of germination.

The gene and encoded protein encoded by CNK01510 (SEQ. ID. NOS. 1 and 2, respectively) is the preferred spore-specific molecule to be labeled in accordance with the assay disclosed herein.

The terms "label," "marker," "probe," "reporter," and "tag" are used interchangeable and mean a molecular moiety or probe of any structure or configuration, that can be detected by any means, now known or developed in the future, by which a vegetative cell, spore, or molecule bearing such a "label," "marker," "probe," "reporter," or "tag" can be distinguished from cells, spores, or molecules not bearing such a "label," "marker," "probe," "reporter," or "tag." The terms include, without limitation, radioactive labels, fluorescent labels, chromophoric labels, affinity-based labels (such as antibody-type markers), chemiluminescent labels, and the like. Conventional radioactive isotopes used for detection include, without limitation, $^{32}P$, $^{2}H$ and many others. A huge number of fluorescent and chromophoric probes are known in the art and commercially available from numerous worldwide suppliers, including Life Technologies (Carlsbad, CA, USA), Enzo Life Sciences (Farmingdale, NY, USA), and Sigma-Aldrich (St. Louis, MO, USA). Luciferase is the preferred marker. Complete kits for accomplishing luciferase labeling to a desired substrate are commercially available from several suppliers, including Promega Corporation, Madison, WI (e.g., Promega's NanoLuc®-brand vectors and NanoGlo®-brand luciferase assay systems).

The term "operationally linked" or "operationally connected" when referring to joined polynucleotide sequences denotes that the sequences are in the same reading frame and upstream regulatory sequences will perform as such in relation to downstream structural sequences. Polynucleotide sequences which are operationally linked are not necessarily physically linked directly to one another but may be separated by intervening nucleotides which do not interfere with the operational relationship of the linked sequences. Similarly, when referring to joined polypeptide sequences, operationally linked means that the functionality of the individual joined segments are substantially identical as compared to their functionality prior to being operationally linked. For example, a fluorescent protein or chemiluminescent protein can be fused to a polypeptide of interest and in the fused state retain its fluorescence or chemiluminescence, while the fused polypeptide of interest also retains its original biological activity.

All strains used in the working examples were of the serotype D background (*Cryptococcus neoformans* var. *neoformans* strains JEC20 (ATCC 96909) and JEC21 (ATCC 96910 and ATCC MYA-565). Sec Kwon-Chung K J, Edman J C, Wickes B L (1992) "Genetic association of mating types and virulence in *Cryptococcus neoformans*," *Infect Immun.* 60:602-605 (pmid: 1730495) and Moore T D, Edman J C (1993) "The alpha-mating type locus of *Cryptococcus neoformans* contains a peptide pheromone gene," *Mol Cell Biol.* 13:1962-1970 (pmid: 8441425). All were handled using standard techniques and media as described in Sherman F. (2002) "Getting started with yeast," *Methods Enzymol.* 350:3-41(pmid: 12073320) and Alspaugh J A, Perfect J R, Heitman J. (1998) "Signal transduction pathways regulating differentiation and pathogenicity of *Cryptococcus neoformans*," *Fungal Genet Biol.* 25:1-14 (pmid: 9806801).

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made. The indefinite articles "a" and "an" mean "one or more" unless explicitly stated otherwise.

All combinations of method or process steps as used herein can be performed in any order, unless otherwise specified or clearly implied to the contrary by the context in which the referenced combination is made.

The methods disclosed herein can comprise, consist of, or consist essentially of the essential elements and limitations of the method described, as well as any additional or optional ingredients, components, or limitations described herein or otherwise useful in microbiology, biochemistry, and/or mycology.

The Method:

At the core of the present invention is the realization that targeting a cellular process that is specific to organisms that sporulate—namely, spore germination—is likely to yield highly effective antifungal compositions that exhibit fewer side-effects than conventional antifungal drugs when used in humans. (Organisms that produce spores include fungi, bacteria, protists, plant seeds, ferns, and the like.) What then is needed then is a high-throughput assay that can evaluate compounds for their ability to inhibit fungal spore germination. As shown in FIG. 1, it is known that spores are infectious agents. FIG. 1 is a graph showing survivability in a widely accepted mouse model of cryptococcosis. See Giles et al. *Infect. Immun.* 2009, 77(8):3491. Here, mice were infected with spores or yeast of *C. neoformans* var. *grubii*. Spores ($10^5$) or yeast ($10^5$) were administered to the test animals via intranasal inhalation. Mice infected with spores are shown in black circles; mice infected with yeast are shown in white circles. As can be seen in FIG. 1, the mice died at virtually identical rates. In other words, *Cryptococcus* spores are just as virulent as the yeast form.

Figure 2A:
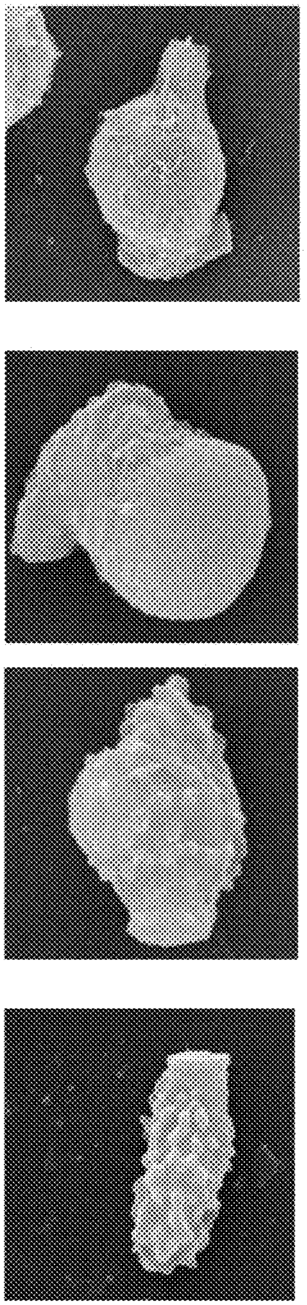
FIG. 2A is a series of scanning electron micrographs showing morphological transitions during germination. The germinating spore is false-colored green; the emerging yeast wall is false-colored yellow, and the resulting daughter cell is false-colored orange. Bar=1 μm for 0, 4, and 8 Hr; bar=2 μm for 12 Hr.
Figure 2B:
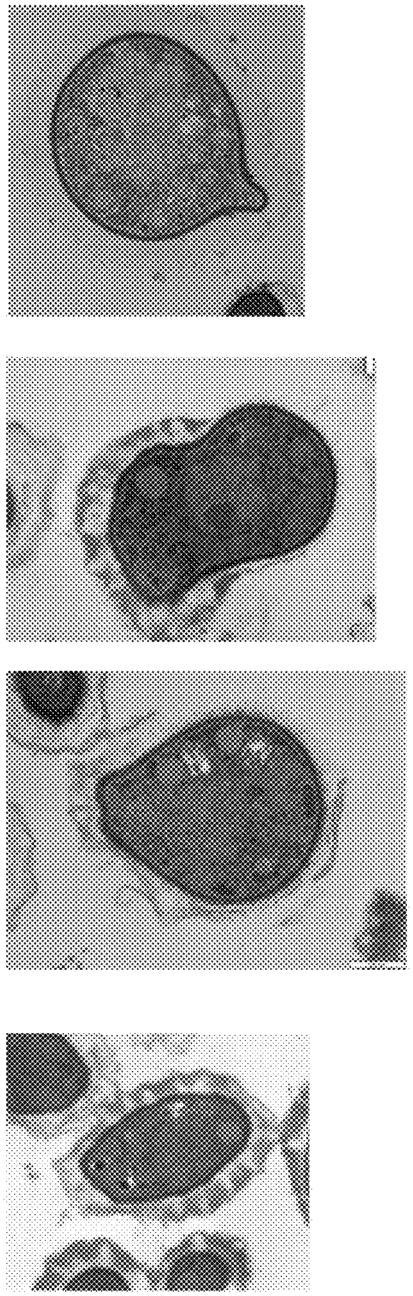
FIG. 2B is a series of micrographs analogous to those in FIG. 2A using transmission electron microscopy rather than scanning electron microscopy. Bars=500 nm.

The method functions on two principles. The first principle is that the vegetative form of organisms, especially fungi, are very different, morphologically than their corresponding spores. This is shown quite convincingly in FIGS. 2A and 2B. FIG. 2A is a series of scanning electron micrographs showing the morphological transitions that take place during germination of *C. neoformans* spores. A *C. neoformans* spore is shown in the far left photo. The germinating spore is false-colored green. The emerging yeast wall is false-colored yellow. This can been seen initially in the photo second from the left and then in a much more pronounced fashion in the third photo of the series. The daughter cell is false-colored orange and is seen clearly in the far right photo. A simple visual comparison between the far left and far right photos in FIG. 2A illustrates the significant morphological differences between a spore of *C. neoformans* (on the left) and a yeast (vegetative form, on the right). As can be seen from FIG. 2A, the spore is roughly cylindrical and clearly has a major axis that is much longer than its minor axis. The vegetative yeast form, in contrast is more nearly spherical or globular. Its major and minor axes are much closer in physical length. FIG. 2B shows the same phenomenon using transmission electron microscopy rather than scanning electron microscopy. Spores are quantitatively smaller and more oblong than yeast.

The second principle is that the inventors have identified 18 proteins that are expressed at far greater levels in the spore form as contrasted to the yeast form. Thus, by affixing a marker to one or more of these spore-specific proteins, the extent of germination can be tracked by following changes in the signal generated by the marker as the spore-specific protein is degraded during the germination process.

The first step of the method is to provide bacterial, fungal, or plant spores transformed to contain and express a detectable marker, wherein the marker is operationally linked to a spore-specific or a yeast-specific protein. The marker is preferably a protein fluorophore or protein chemiluminescent marker, such as luciferase, fluorescent protein A, green fluorescent protein, etc. The marker protein is incorporated into spores or yeast by fusing the gene encoding the marker protein to a spore-specific or yeast-specific target gene. The spore then produces the spore-specific protein with the marker attached. (Or the yeast then produces the yeast-specific protein with the marker attached.) The marker will thus generate a first signal associated with the spores. That first signal remains unchanged for as long as the spores remain intact. However, when the spore germinates, the spore-specific protein and its attached marker are degraded, which then alters the signal generated by the attached marker (or the yeast-specific marker is increased). A second signal measurement taken after germination is thus proportional to the extent of germination.

Figure 3A:
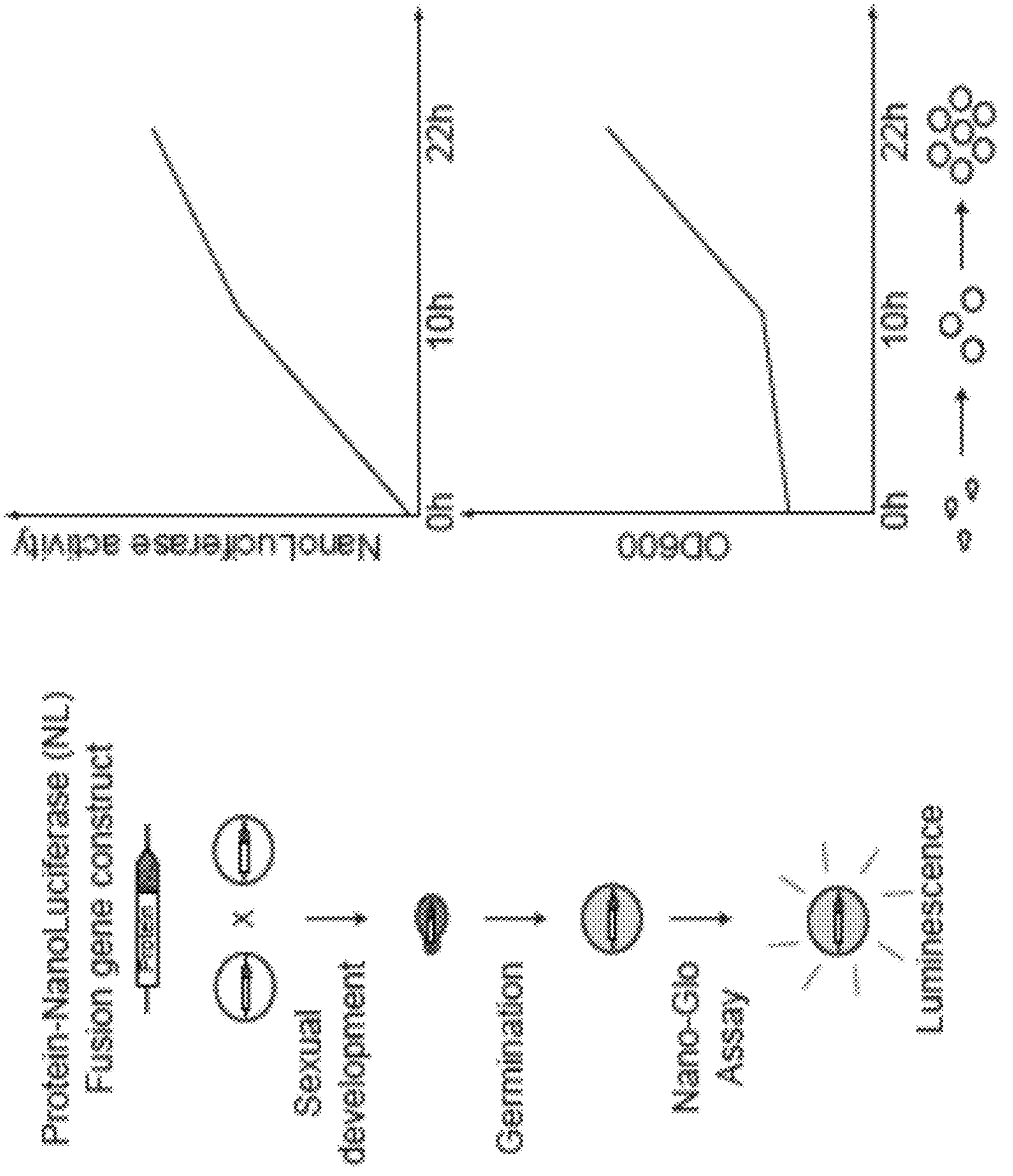
FIG. 3A is a schematic diagram of a screening assay for an uninhibited germination reporter strain as it undergoes germination (left-hand panel) and graphs depicting germination as reported by NanoLuciferase (NL) activity (top right, NanoLuc®-brand luciferase, Promega Corporation, Madison, WI), and as measured by optical density (OD) (bottom right). The schematic pictures below show the morphology and number of cells over time. This example depicts a yeast-specific protein.

This process is shown schematically in FIG. 3A. As shown in the left-hand side of the figure, the yeast form of the organism (in this case *C. neoformans*) was transformed to contain a fusion construct comprising a spore-specific protein fused to a luciferase gene. The transformed yeast were cultured to yield a population of propagating yeast that include the fusion construct. The yeast were then induced to sporulate. A first measure of the signal generated by the luciferase marker generated by the fusion construct is taken. This is shown at Time=0 in the two right-hand graphs depicted in FIG. 3A. The upper graph show the signal generated by the reporter as the spore germinate. The lower graph shows the optical density of the culture solution at 600 nm ($OD_{600}$) over the same time period. As can be seen from the two graphs, as the spore germinate and multiply, the optical density increases (as the number of cells increases). In a corresponding fashion, the signal generated by the marker displays a proportional rise. The schematic pictures below show the morphology and number of cells over time.

Figure 3B:
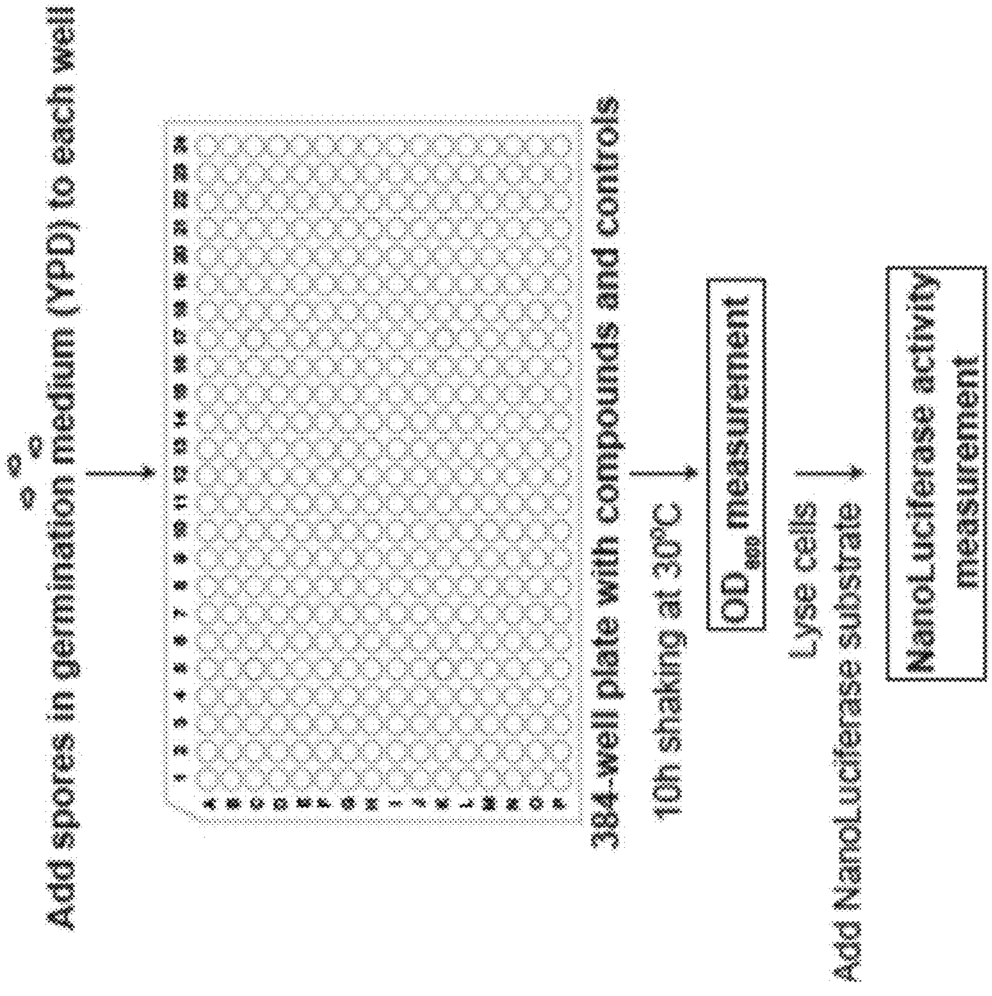
FIG. 3B is a schematic diagram showing the workflow for the screening assay.

The assay can be implemented in a massively redundant, massively high-throughput format that is easily automated using conventional multiwall plates and robotic equipment. (Laboratory robotics for handling multiwall culture plates are available from a host of international commercial suppliers, including Agilent Technologies (Santa Clara, California), Beckman Coulter (Grants Pass, Oregon), Hudson Robotics (Springfield, New Jersey), and many others.) For a non-limiting example, see FIG. 3B, which is a schematic diagram showing the workflow for a high-throughput screening assay according to the present disclosure. As shown in FIG. 3B, the method can be implemented using conventional 384-well incubation plates. Spores to be studied are modified to contain a suitable marker, as described earlier. The spores are then incubated in a multiwall plate in a suitable germination medium. For many fungi, yeast extract-peptone-dextrose growth medium (YPD or YEPD) is suitable. (YPD is a well known medium for fungal germination and contains roughly 2% w/v bacto-peptone, 1% w/v yeast extract, and 2% w/v dextrose. A 1 L batch is made by combining 20 g bacto-peptone, 10 g yeast extract, and 20 g dextrose, adding water to 1 L and then autoclaving before use.)

A first signal from each well of the multiwall plate is then taken at the start of the incubation period. The contents of each well can be arranged in any suitably logical fashion, with positive and negative control wells, and wells containing compounds to be tested for their ability to inhibit germination of the spores, perhaps in appropriate serial dilutions of the compounds. The entire multiwall plate is then cultured for a time, temperature, humidity, etc. that is conducive to germination of the spores. After a set time, and OD600 measurement may optionally be taken to confirm that in the control wells the spores responded appropriately. The cells are then lysed, luciferase substrate is added, and a second measurement of the signal generated by the marker is taken. The extent of germination can then be determined by comparing the first signal to the second.

Figure 3C:
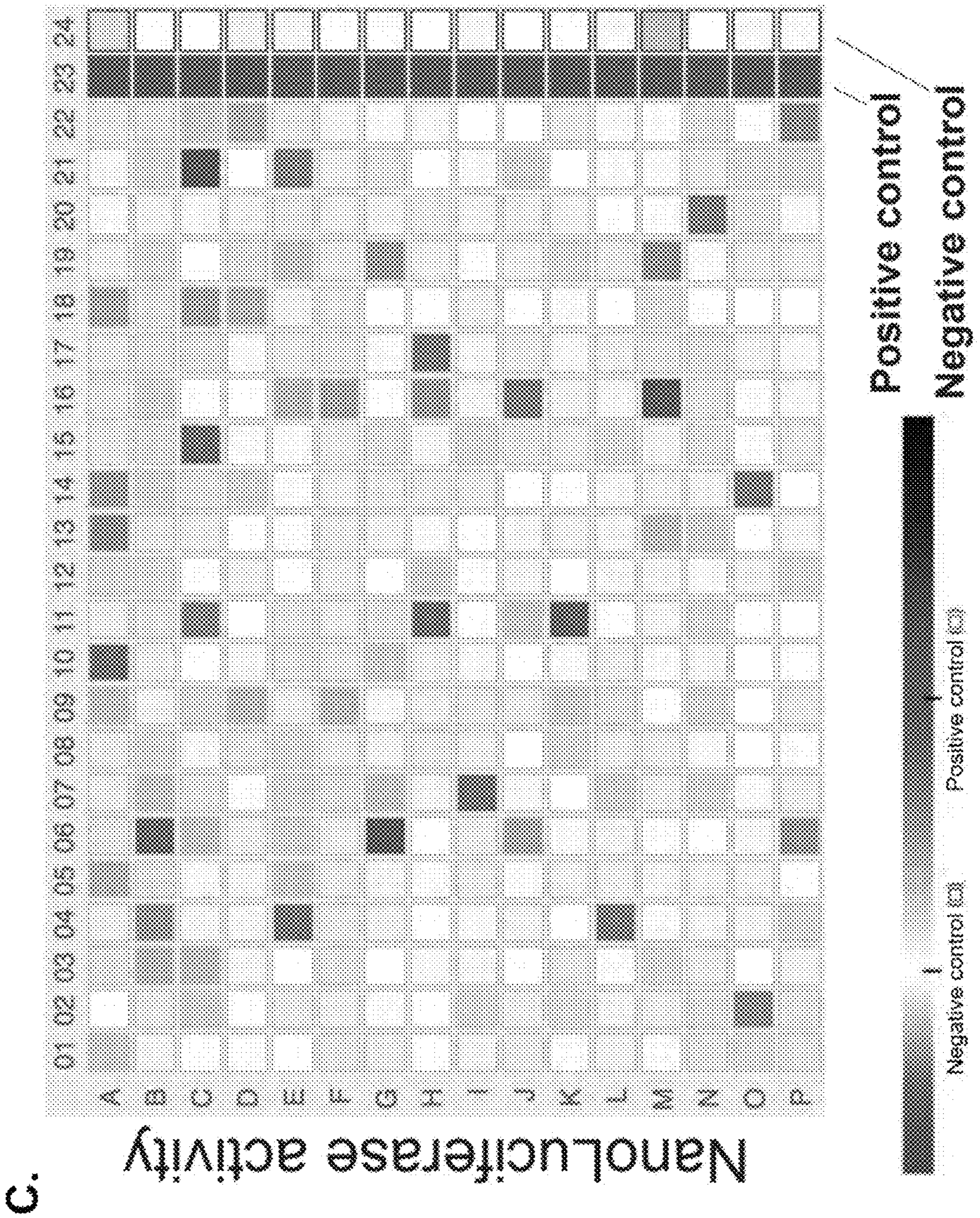
FIG. 3C shows representative plates from the screening assay described in FIGS. 3A and 3B, showing wells that contain germination-inhibiting compounds in red.

FIG. 3C shows a representative multiwall plate from the resulting from the method just described. Positive and negative control wells are in columns 23 and 24, respectively. Wells that contain germination-inhibiting compounds in various shades of pink/red, with the darker red hues indicating great inhibitory activity. The signals can be gathered, digitized, recorded, and compared using a photomultiplier tube, in conventional fashion. Thus, wells H11, K11, C15, M16, and C21 all appear to contain very effective germination-inhibiting compounds.

Figure 3D:
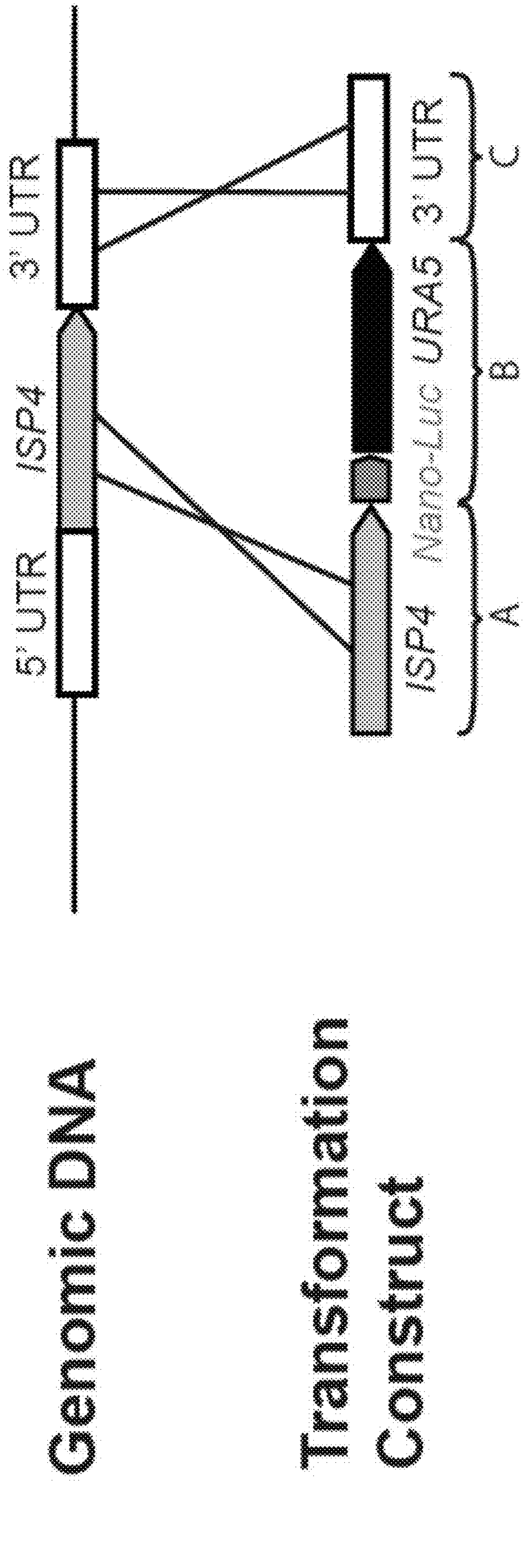
FIG. 3D is a schematic diagram of the transformation construct containing a marker, in this case a gene encoding luciferase ("Nano-Luc").

FIG. 3D shows a schematic diagram of a vector used to transform a spore so that it includes a marker responsive to germination An exemplary protocol, using luciferase as the marker, can be accomplished using commercial kits and largely following the manufacture's instructions on how to use the kit. A preferred kit for is Promega's Nano-Luc®-brand vectors and Nano-Glo®-brand luciferase assay system.

Briefly, homologous recombination is utilized to tag spore proteins with luciferase under their endogenous promoters. See FIG. 3D. In this fashion, their expression levels in the spores will remain undisturbed by tagging. As illustrated in FIG. 3D, the transformation construct contains three parts (A, B, and, C). Part A includes the sequence that encodes ISP4 but without a stop codon. Part B includes NanoLuc sequence (GeneBank sequence number KM359770) and *C. neoformans* URA5 gene (GenBank sequence number AE017347.1), the latter of which serves as a selection marker for cell transformation. Part C includes the 3' UTR of ISP4, so that together with Part A, the transformation construct will be more favorably integrated into the genome through homologous recombination. Individual parts were generated by regular PCR and the full-length transformation construct was created using fusion PCR. See Davidson R C, Blankenship J R, Kraus P R, de J Berrios M, Hull C M, D'Souza C, et al. A PCR-based strategy to generate integrative targeting alleles with large regions of homology. *Microbiology.* 2002; 148: 2607-2615. PMID: 12177355. The construct was transformed into cells by biolistic transformation before selection. See Toffaletti D L, Rude T H, Johnston S A, Durack D T, Perfect J R. Gene transfer in *Cryptococcus neoformans* by use of biolistic delivery of DNA. *J Bacteriol.* 1993; 175: 1405-1411. PMID: 8444802.

The present inventors have identified a significant number of proteins in *C. neoformans* that were detected in spores only. Thus, these proteins are all candidates for labelling in the present invention. In *C. neoformans* and in other fungi where the corresponding genes are conserved, one or more of the following proteins can be labelled with the marker: XP_567740.1 (SEQ. ID. NO: 2), XP_566791.1 (SEQ. ID. NO: 4), XP_570303.1 (SEQ. ID. NO: 6), XP_571089.1 (SEQ. ID. NO: 8), XP_571997.1 (SEQ. ID. NO: 10), XP_569295.1 (SEQ. ID. NO: 12), XP_569173.1 (SEQ. ID. NO: 14), XP_569068.1 (SEQ. ID. NO: 16), XP_569336.1 (SEQ. ID. NO: 18), XP_567136.1 (SEQ. ID. NO: 20), XP_568990.1 (SEQ. ID. NO: 22), XP_570610.1 (SEQ. ID. NO: 24), XP_571921.1 (SEQ. ID. NO: 26), XP_572925.1 (SEQ. ID. NO: 28), XP_570796.1 (SEQ. ID. NO: 30), XP_571548.1 (SEQ. ID. NO: 32), XP_570447.1 (SEQ. ID. NO: 34), XP_571343.1 (SEQ. ID. NO: 36).

Figure 4:
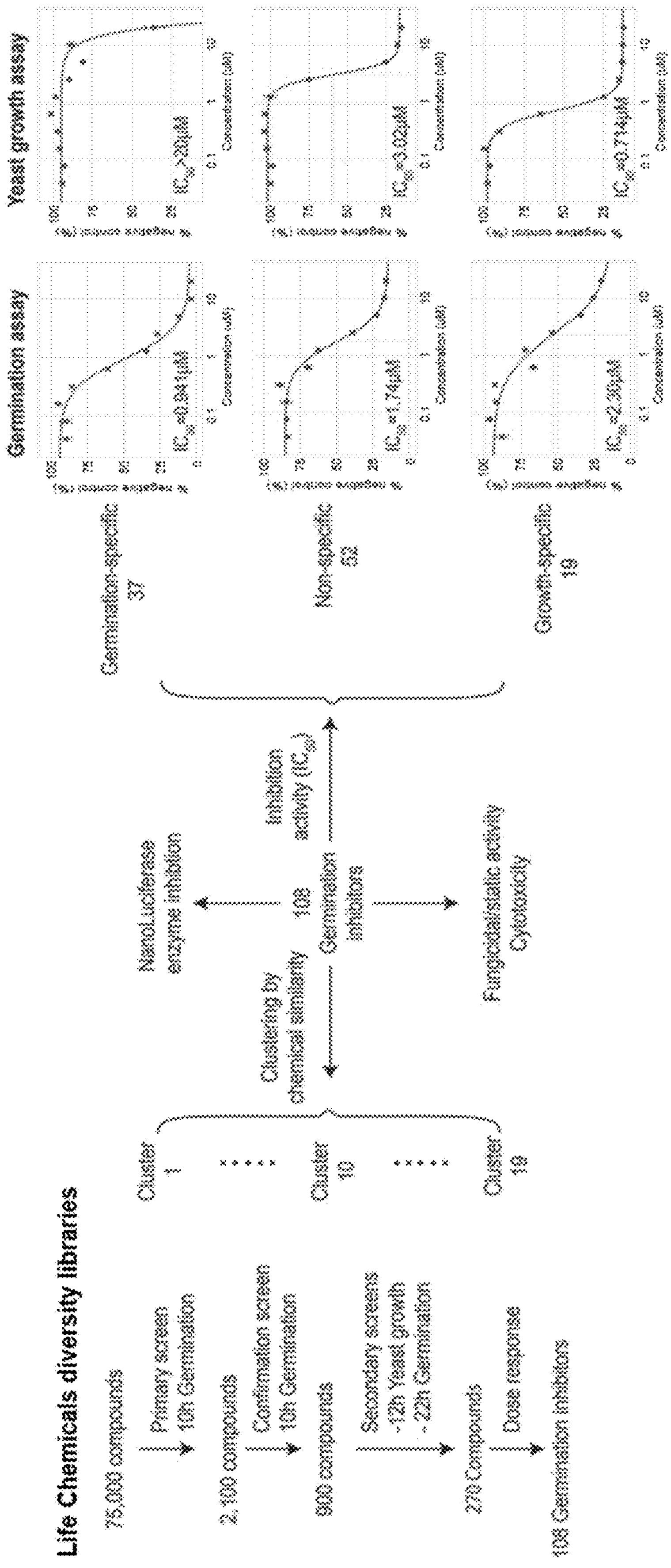
FIG. 4 is a flow chart showing the workflow of a high-throughput screening assay according to the present disclosure.

FIG. 4 is a flow chart showing the workflow of a high-throughput screening assay according to the present disclosure. Here, the figure shows how a large library of 75,000 compounds was screened using the present method set up in high-throughput format. As shown on the left-hand side of the figure, the full library was first subjected to a primary screening comprising a 10-hour germination, followed by evaluating which compounds showed initial interested as germination inhibitors. This yielded 2,100 putative "hits," i.e., compounds that at least initially showed promise as germination inhibitors. These 2,100 hits were then re-screened and the upper 900 best performing inhibitors were tested further. These 900 compounds were then re-screened using longer germination and yeast growth incubation times. This resulted in 270 compounds being advanced for further study. This group of 270 compounds was then studied using the method described herein to determine if any of the compounds inhibited spore germination and/or fungal growth in a dose-dependent fashion. This final screen yielded 108 compounds from the original 75,000 compounds that inhibited fungal spore germination and/or yeast grown in a dose-dependent fashion.

As shown in the middle panel of FIG. 4, the 108 compounds that were "hits" were then clustered by structural similarity and further tested to see if their anti-fungal properties were germination specific (i.e., primarily germination inhibitory), non-specific, or primarily growth specific. As shown in the right-hand graphs of FIG. 4, 37 of the compounds specifically inhibited germination in a dose-dependent manner; 52 of the compounds were non-specific, dose-dependent inhibitors; and 19 of the compounds specifically inhibited vegetative fungal growth in a dose-dependent manner.

Figure 5B:
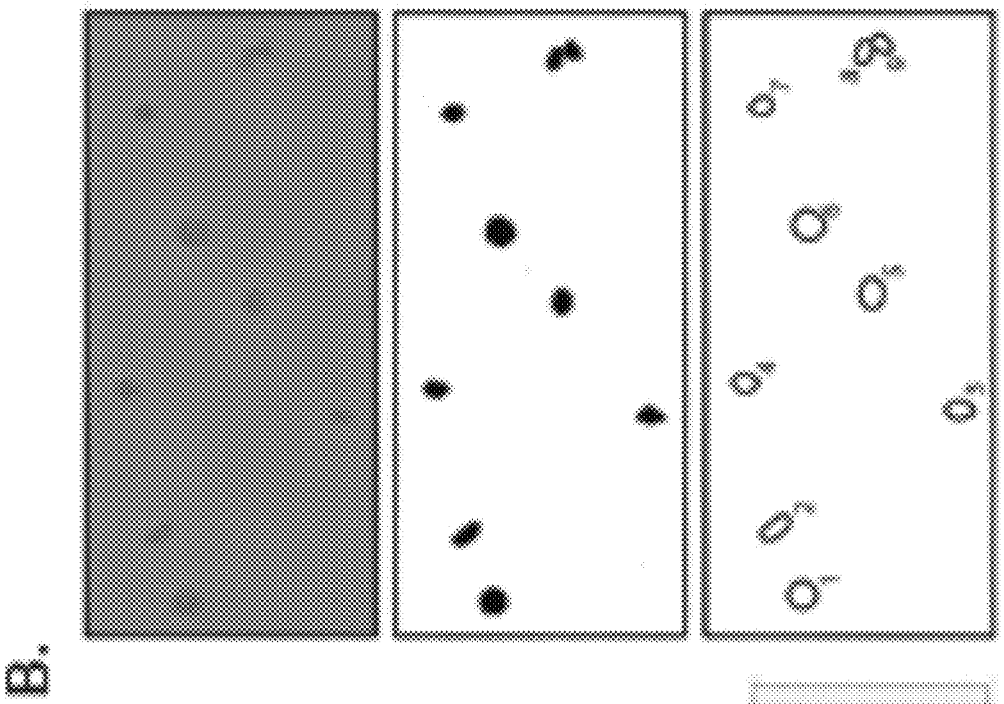
FIG. 5B depicts representative raw images of the fungal cells (spores and germinated cells) in the device shown in FIG. 5A. Image processing steps are then applied to the raw images to discriminate between spores and germinated cells. These process steps may include, without limitation, applying a density threshold to the raw images and then automatically detecting and measuring the cells 2-D area and aspect ratio.
Figure 5A:
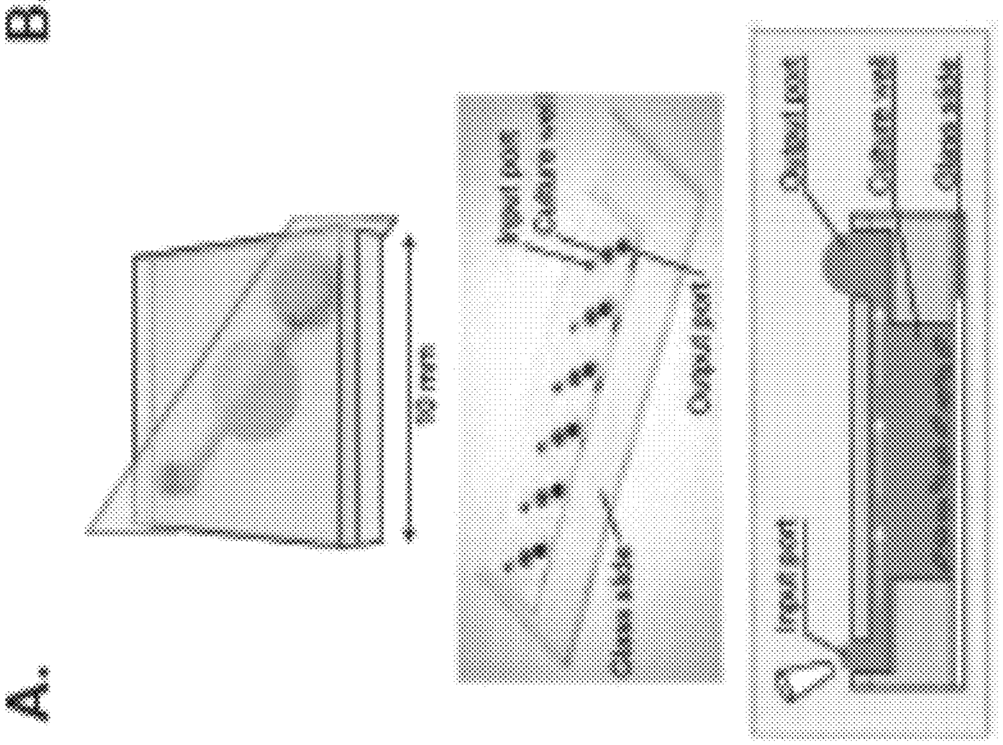
FIG. 5A shows schematic views of a microliter-scale well device and how it operates. The microfluidic device includes an input port connected to a culture well connected to an output port. Each microfluidic chamber is built upon a transparent support, such as a glass microscope slide. The microfluidic device is dimensioned and configured to culture and image non-adherent cells, such as spores and germinated fungi, yeast, and the like. The top panel of FIG. 5A shows a perspective view of a single microfluidic culturing device. The middle panel of FIG. 5A shows six (6) such devices disposed on a glass slide. Each of the six devices shown is filled with 10 μL of blue dye. The bottom panel of FIG. 5A shows a front elevation cutaway of the device shown in the top panel.

As shown in FIGS. 5A and 5B, the method described herein can also be formatted for continuous studies using a microfluidic test bed. The test bed, depicted schematically in FIG. 5A, comprises a microliter-scale culture well having an input port and an output port. That is, the device includes an input port operationally linked in fluid connection to to a culture well which is operationally linked in fluid connection to an output port. Each microfluidic chamber is built upon a transparent support, such as a glass microscope slide. The microfluidic device is dimensioned and configured to culture and image non-adherent cells, such as spores and germinated fungi, yeast, and the like. The top panel of FIG. 5A shows a perspective view of a single microfluidic culturing device. The middle panel of FIG. 5A shows six (6) such devices disposed on a glass slide. These six devices held 10 μL blue dye. The bottom panel of FIG. 5A shows a front elevation cutaway of the device shown in the top panel. In this bottom panel, fluid flow is depicted as moving from left-to-right. Non-adherent cells are retained within the culture well, while the medium gently flows above them. Compounds to be tested are introduced through the input port, where they then flow to the culture well to interact with the cells therein. When built on an optically transparent substrate, the cells can be visualized and photographed in real time, as shown in the photos in FIG. 5B.

FIG. 5B depicts representative raw images of the fungal cells (spores, germinating cells, and yeast) in the device shown in FIG. 5A. Various imaging processing steps, described in detail below, are then applied to the raw images to discriminate among spores, germinating cells, and yeast. These process steps may include, without limitation, applying a density threshold to the raw images and then automatically detecting and measuring the cells' 2-D area and aspect ratio.

Figure 6:
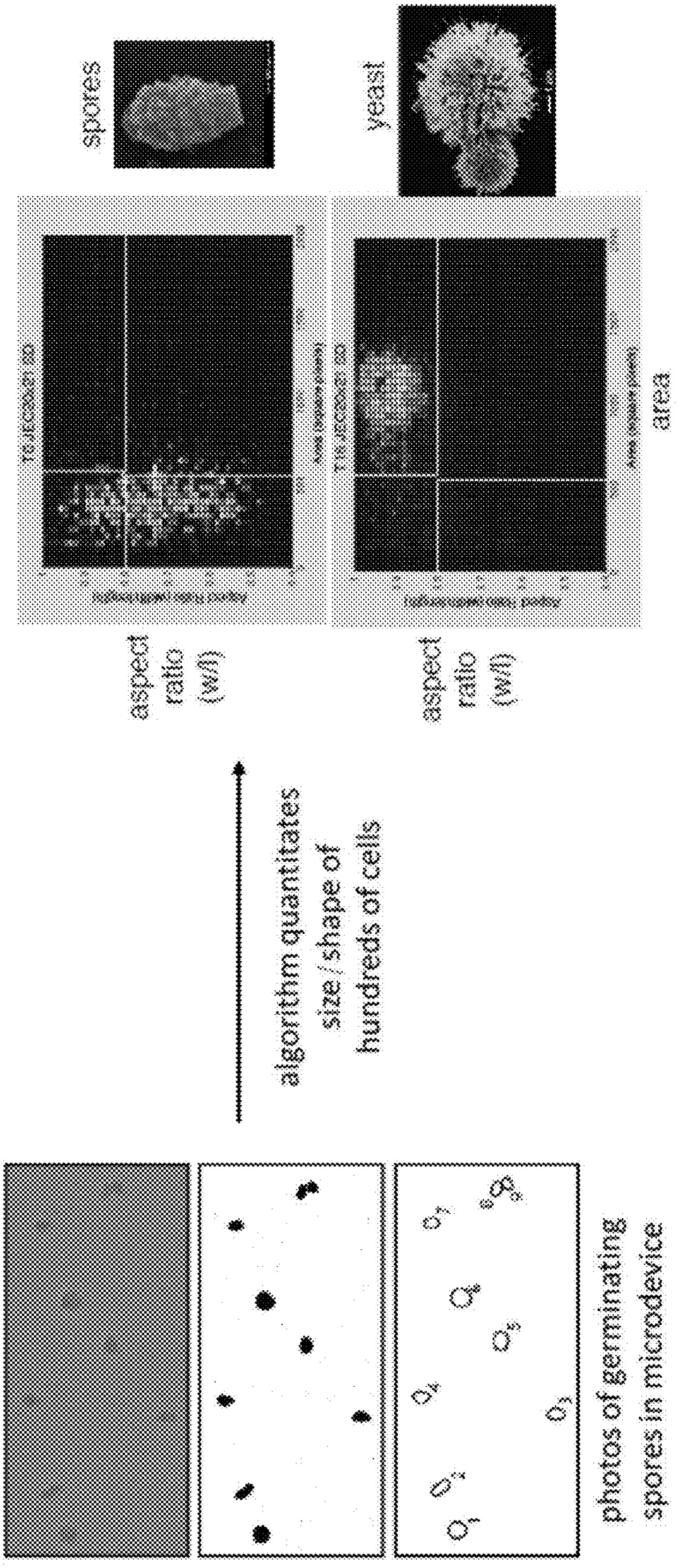
FIG. 6 depicts how photos of germinating spores in the micro-device depicted in FIG. 5A were analyzed for the size and shape of the cells and the aspect ratio calculated. This was done using modified algorithms of ImageJ, a public domain, open-source, Java-based image processing program, which was developed originally by Wayne Rasband at the Research Services Branch of the National Institutes of Health. ImageJ can be downloaded free of charge at https://imagej.nih.gov/ij/download.html. The images of the cells are then plotted based on their 2-D area (X-axis) versus their aspect ratio (Y-axis) as shown in the right-hand panels of FIG. 6. Spores, because they are more oblong and smaller in area, plot to the bottom left-hand side of the histogram; germinated cells, because they are more spherical and larger in area, plot to the upper right quadrant of the plots.

FIG. 6 shows how computer processing can be brought to bear to automatically discriminate between ungerminated spores and vegetative yeast after a culture period has been completed. The left-hand side of FIG. 6 shows the three raw photographs from FIG. 5B. These are raw photographs of the germinating spores in the microfluidic device shown in FIG. 5A. The photos are digitized from the outset. The digitized images were analyzed for the size and shape of each cell in each image. The area of each cell, as well as its aspect ratio can be determined using a public domain, open-source, Java-based image processing program called ImageJ. Several other commercial image processing software packages can also accomplish this task. For example, Stream-brand image analysis software from Olympus Corporation (Waltham, MA) and PAX-it brand image analysis software from MIS, Inc. (Villa Park, IL). The images of the cells are then plotted based on their 2-D area (X-axis) versus their aspect ratio (Y-axis) as shown in the right-hand panels of FIG. 6. As can be seen from the plots in FIG. 6, the spores (upper plot) cluster in a distinctly different location and with a distinctly different distribution as compared to the vegetative yeast (lower plot). This is because spores, being more oblong and smaller in area, plot to the left-hand side of the histogram—indicating smaller average area and ovoid nature in the photographs. Spores tend to toward a wider distribution of their aspect ratios and areas. This may be due to the fact that the spores settle in the device at many angles. When photographed, spore aspect ratios and sizes are are more variable than in reality. Yeast, because they are more spherical and larger in area regardless of the position from which they are photographed, plot in a tight cluster in the upper right quadrant of the histograms.

Figure 7A:
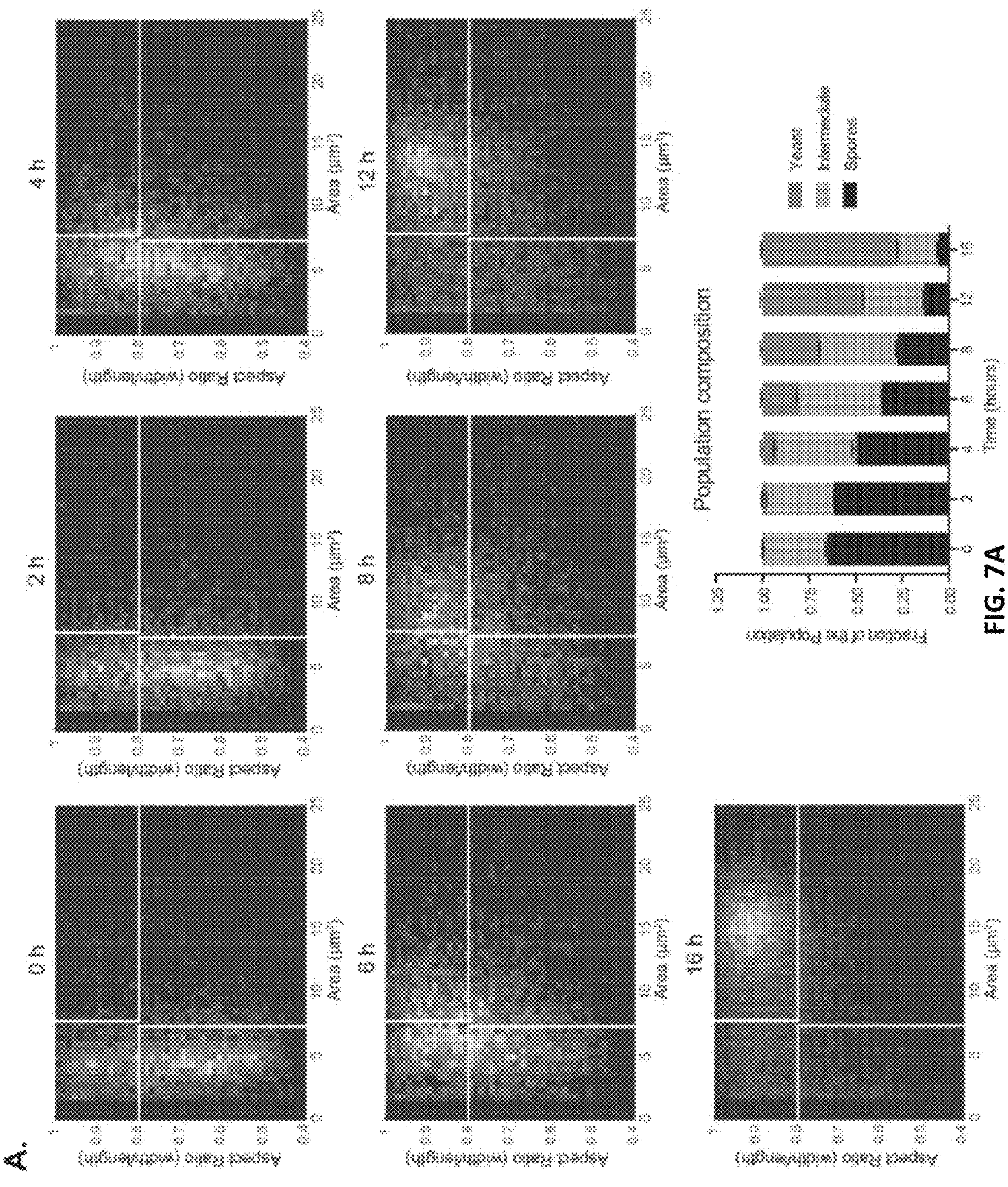
FIG. 7A depicts a series of photographic analyses showing that germination in microscale devices as described herein can be determined by cell area versus aspect ratio. Thus, each panel in FIG. 7A depicts the germination dynamics of spores visualized by 2D histograms of cell area vs. aspect ratio. Data are also shown as a stacked bar plot of the population composition over time (at lower right). Colors are normalized on each plot such that yellow represents the area and aspect ratio combination with the most cells observed and dark blue represents area and aspect ratio combinations that were not observed. Cells in the lower left quadrant are defined as spores; cells in the upper right quadrant as yeast; all remaining cells are classified as intermediates.
Figure 7B:
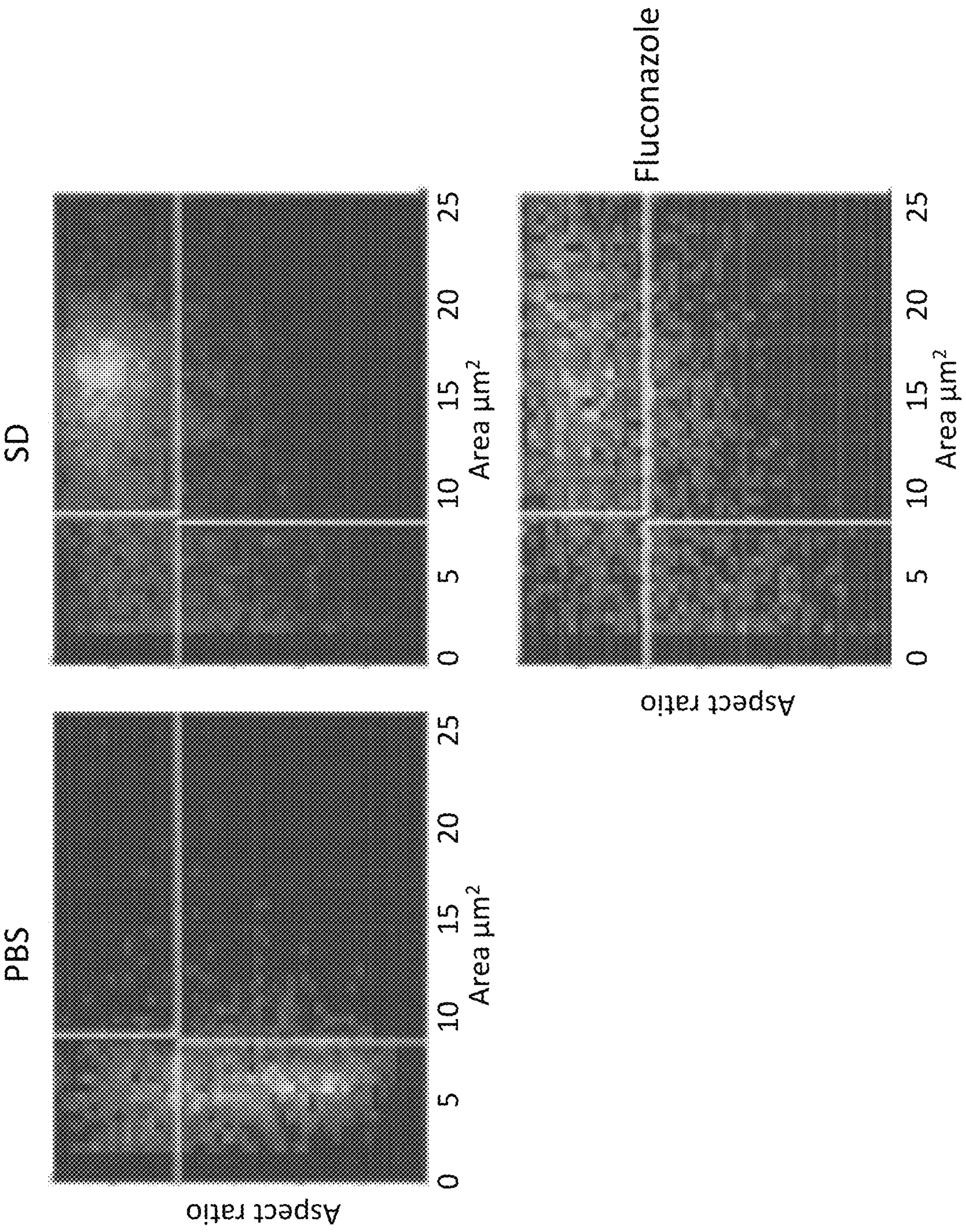
FIG. 7B shows 2D histograms as in FIG. 7A, but for a 16-hour germination of *Cryptococcus* spores using PBS as a control (no germination), synthetic dextrose growth medium (SD) alone (full germination in the absence of compounds), and fluconazole (16 mg/mL) in the presence of growth medium.

Further examples of how spores, germinating cells, and yeast can be compared is shown in FIGS. 7A and 7B. FIG. 7A depicts a series of photographic analyses further demonstrating that germination in microscale devices as described herein can be determined by cell area versus aspect ratio. Each panel in FIG. 7A depicts the germination dynamics of spores visualized by 2D histograms of cell area vs aspect ratio, as well as a stacked bar plot of the population composition over time (at lower right). Colors are normalized on each plot such that yellow represents the area and aspect ratio combination with the most cells observed and dark blue represents area and aspect ratio combinations that were not observed. Cells in the lower left quadrant are defined as spores; cells in the upper right quadrant as yeast; all remaining cells are classified as intermediates undergoing germination. FIG. 7B shows 2D histograms as in FIG. 7A, but for a 16-hour germination of *Cryptococcus* spores using PBS as a control (no germination), synthetic dextrose growth medium (SD) alone (full germination in the absence of compounds), and the antifungal compound fluconazole (16 mg/mL) in the presence of growth medium. In this study, we demonstrate that spore germination is a viable target for antifungal development by identifying and characterizing FDA approved drugs able to inhibit both spore germination and yeast replication. These inhibitors have the potential of becoming tools to probe the essential fungal process of spore germination, or repurposed into antifungal therapies. Importantly, we determined that one of the drugs, Pentamidine, was effective at lowering fungal burden in vivo and could be repurposed as a prophylactic treatment against *Cryptococcus* pathogens.

Germination Provides a Suitable Target for the Development of Novel Antifungals:

Limited therapies exist to combat fungal disease. Humans and fungi share many biological processes due to their eukaryotic nature. Because fungi-specific drug targets are difficult to find, potent antifungal agents often have toxic side-effects in humans. In the quest to find novel fungal-specific targets, the field has mainly focused on the cell membrane processes (ergosterol biosynthesis), and the fungal cell wall (β(1,3)-glucan synthesis). While these targets have been effective in the discovery of antifungals in the past; the lack of novel antifungal therapies is an indication that these targets currently have limited success. It is critical that novel fungi-specific targets are identified for the development of new antifungals. This requires identifying new cell processes to probe that are unique to fungi. Fungal spore germination provides one of these novel targets.

Fungal spore germination has been previously suggested to be a modified cell cycle. Recently discovered evidence suggests otherwise. In previous studies we identified and characterized spore-enriched proteins. One of these proteins (Isp2) was found to stall germination for two hours prior to initiating vegetative growth. Isp2 showed no apparent phenotype in vegetatively growing yeast. Isp2, along with other spore germination-specific results, indicate that it is unlikely that germination is simply a modified cell cycle. Spore germination in not only a unique fungal process but is also unlike any process defined in humans. The uniqueness of fungal spore germination makes it a prime process to probe in the effort to develop novel antifungals. The examples below show that using germination inhibition as a signal can identify drugs that could be repurposed in the treatment of invasive fungal diseases.

Targeting Germination Provides a Mechanism for Prevention:

In addition to providing a fungal-specific drug targets, targeting germination provides a unique opportunity for preventing fungal disease. Spores are stress-resistant cell types that are known infectious particles of many fungal pathogens, and have distinct phenotypes compared to yeast when interacting with hosts. Developing antifungals that target all potential infectious particles could be used to protect against fungal pathogens through prophylaxis treatment. If a low toxicity antifungal is found, prophylactic treatment could be administered to immunocompromised individuals, the population most at risk of developing invasive fungal infections.

Screening Characterized Drugs Allows for the Potential Development of Tools:

The screening of already approved FDA drugs provides a unique opportunity to screen drugs that often have known targets. By screening compounds with known inhibition targets, pathways can be identified that could be potentially important to fungal spore germination. These compounds can be used to probe fungal spore germination to help understand this critical fungal differentiation process. One of the clearest examples of a potential tool in this study was alexidine hydrochloride, which had strong antifungal activity and was a potent inhibitor of fungal spore germination. See the Examples section. This drug has previously been reported to inhibit phospholipases of *Cryptococcus* (Ganendren et al., 2004). This may suggest that phospholipases are important for viability of fungal spores. The ability of alexidine to inhibit other fungal processes, however, is unclear. In the future, we will use alexidine as a tool to probe the molecular events of phospholipid biosynthesis in fungal spore germination.

Pentamidine, a Potential Antifungal Prophylactic Against *Cryptococcus* Infection:

Screening FDA-approved drugs has the benefit of potential repurposing as these drugs could reach patients in need sooner than novel compounds. The Examples section shows that pentamidine has huge promise in repurposing for a variety of reasons. Pentamidine, an antiparasitic, is only approved for use against one fungal pathogen, *Pneumocystis*. Pentamidine is approved for use in immunocompromised individuals, which is the primary group of individuals infected by *Cryptococcus* pathogens. Pentamidine already exists in an aerosolized formulation which allows for the drug to build up in the lung, which is the main site where *Cryptococcus* pathogens establish infections. Finally, this drug is already approved for use prophylactically against *Pneumocystis*, which would suggest that pentamidine could be used to protect immunocompromised individuals from cryptococcosis.

The Examples section shows that pentamidine was able to inhibit *Cryptococcus* infectious particles in vitro, was effective at lowering fungal burden in a mouse model of infection and, when used prophylactically, was able to inhibit spore germination in vivo, suggesting that pentamidine can build up in the lung sufficiently to inhibit this stress resistant cell type. The ability to inhibit both cell types, and the nature of this drug, suggest that it could make an ideal prophylactic against *Cryptococcus* pathogens which cause hundreds of thousands of deaths per year in immunocompromised individuals. While pentamidine is often not the first choice for prophylaxis against *Pneumocystis*, the data presented herein shows that pentamidine can be used to protect patients against other fungal pathogens generally and *Cryptococcus*. spp. specifically.

Pharmaceutical Compositions:

Using the method disclosed herein, the inventors identified four (4) FDA-approved compounds with germination-inhibiting properties that are effective antifungal therapeutics. These four compounds are disulfiram, pentamidine, otilonium bromide, and benzethonium chloride.

Thus, also disclosed herein are pharmaceutical compositions for inhibiting topical and systemic fungal infection in mammals. The compositions comprise a spore germination-inhibiting amount of a compound selected from the group consisting of:

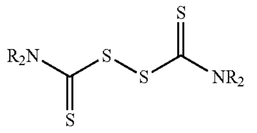

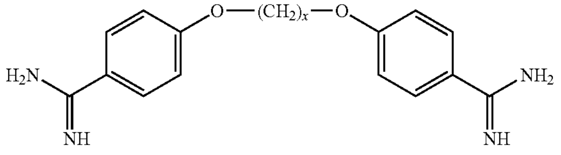

-continued

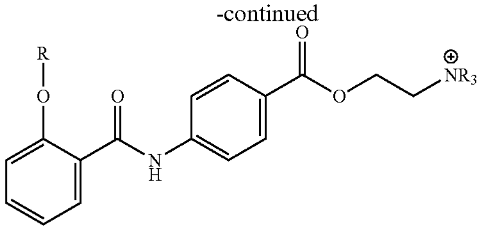

and

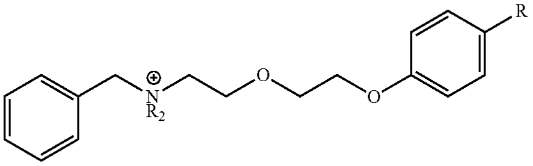

wherein R is linear or branched $C_{1-12}$ alkyl and "x" is an integer of from 1 to 12, and pharmaceutically suitable salts thereof, in combination with a pharmaceutically suitable vehicle.

The active ingredients may be used in combination with a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectable, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, compounds as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant active agent.

For intravenous administration, the compounds may be incorporated into commercial formulations such as Intralipid©-brand fat emulsions for intravenous injection. ("Intralipid" is a registered trademark of Fresenius Kabi AB, Uppsalla, Sweden.) Where desired, the individual components of the formulations may be provided individually, in kit form, for single or multiple use. A typical intravenous dosage of a representative compound as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical state of the subject being treated. The dosage of the composition to be administered to the patient may be determined by one of ordinary skill in the art and depends upon various factors such as weight of the patient, age of the patient, immune status of the patient, etc., and is ultimately at the discretion of the medical professional administering the treatment.

With respect to form, the composition may be, for example, a solution, a dispersion, a suspension, an emulsion or a sterile powder which is then reconstituted. The composition may be administered in a single daily dose or multiple doses.

The present disclosure also includes treating fungal infections (topical and systemic) in mammals, including humans, by administering a spore germination-inhibiting amount of one or more compounds described herein. In particular, the compositions of the present invention may be used to treat fungal infections of any and all description.

The above-described pharmaceutical compositions may be utilized in connection with non-human animals, both domestic and non-domestic, as well as humans.

EXAMPLES

The following examples are included to provide a more complete description of the methods and compositions disclosed and claimed herein. The examples are not intended to limit the scope of the claims in any fashion.

Strain Manipulation, Media and Spore Isolation:

The following strains were used and handled using standard techniques and media as previously described. (Sherman et al., 1987). *Cryptococcus neoformans* serotype D: JEC20, JEC21, JEC20-GFP, JEC21-GFP (Walsh et al. 2018), serotype A: H99, *Candida albicans*: SC5314 and *Aspergillus fumigatus*: AF293. Spores were isolated from cultures as previously described. (Botts et al., 2009). Briefly, yeast of both mating types (JEC20 and JEC21) were grown on YPD for 2 days at 30° C. combined in phosphate buffered saline (PBS) mixed to a 1:1 ratio and spotted onto V8 pH 7 agar plates. Plates were incubated for 5 days at 25° C. and spots were resuspended in 70% Percoll in 1×PBS. Spores were counted using a hemocytometer.

MIC/MFC Experiments:

All minimum inhibitory concentration (MIC) experiments were based on EUCAST methodology. (European Committee on Antimicrobial Susceptibility Testing, a standards-setting committee of the European Society of Clinical Microbiology and Infectious Diseases; EUCAST Development Laboratory for fungi, Statens Serum Institut, Building 211, Artillerivej 5, DK-2300 Copenhagen, Denmark; www.eucast.org.) Yeast cells were grown overnight in liquid YPD and used to inoculate fresh YPD. After 6-hour incubation, yeast cells were washed in 1×PBS and quantified using a hemocytometer. For each drug, $1.25\times10^5$ yeast cells were incubated in RPMI, and 0.33M MOPS, pH 7 at varying concentrations of inhibitors, with a final volume of 200 μL. *Cryptococcus neoformans* cells were incubated for 2 days at 30° C. while *Candida albicans* strains were incubated for 2 days at 35° C. $OD_{600}$ readings were used to assess the MIC values for each drug. To determine minimum fungicidal concentrations (MFC) values, 3 μL per well were plated on YPD and allowed to grow for 2 days. Spinning down of 96-well plates and washing did not alter the read outs of the MFC experiment.

For *Aspergillus fumigatus* MIC, conidia were collected using 0.01% Tween 80 in PBS after 3 days of growth on glucose medium media plates. Conidia at a final concentration of $2\times10^4$ cells were incubated in RPMI, 0.33 M MOPS, and 2% glucose at pH 7 at varying concentrations of inhibitors, with a final volume of 200 μL. MIC values were assessed based on the lowest concentration of drug that had complete absence of germ tubes or hyphae.

Quantitative Germination Assay:

All germination assays are based on Barkal et al., 2016. Briefly, microfluidic devices were loaded with $1\times10^5$ spores, and at 0 hours, SD media with drug of interest, were added to the sample. Spores were allowed to germinated at 30° C. in a humidified chamber and cells were monitored every two (2) hours for 16 hours. Each assay was performed in two (2) individual wells with three (3) field of views acquired from each well. All images were analyzed as previously described based on cell shape and size. Population ratio of spores, intermediate, and yeast cells were determined. Error bars in plots are based on variation between all fields of view acquired. All experiments were able to be reproduced independently. After the 16-hour experiment, samples were plated on YPD and allowed to grow at 30° C. to determine if drugs were completely germicidal or not based on lack of growth. If assays were unable to be performed in microfluidic devices, the $2\times10^5$ spores were incubated in identical conditions outside of PDMS devices and only loaded into devices for image acquisition.

Fungal Burden Animal Studies:

All yeast cells were cultured overnight in YPD, washed and diluted to $5\times10^6$ cells. For JEC20 and JEC21, $2.5\times10^6$ cells of each were combined. Spores were cultured as previously described and diluted to $2\times10^6$ cells. All experiments were performed on 8- to 10-week old C57BL/6J (Jackson Laboratory, Bar Harbor, Maine, USA) female mice (5 mice per group). All mice were infected intranasally with a total of 50 μL. All dosing was performed with 4 mg/kg/day or 1×PBS for three (3) days either prior to infection or 1-day post-infection. Mice were sacked day-4 post-infection and lungs were collected, processed, and fungal burden was assessed.

In Vivo Germination:

Female mice, 8- to 10-week-old C57BL/6J (Jackson Laboratory) female mice (3 mice per group) were used. Mice were dosed with either 4 mg/kg/day or 1×PBS (50 μL) for three (3) consecutive days. Mice were intranasally infected with $2\times10^6$ JEC20-GFP×JEC21-GFP spores, strains described in Walsh et al., 2018. After 8 hours post-infection, mice were sacked and lavaged with 0.05% TirtonX in 1×PBS. Lavage suspension underwent a series of treatments and washes, in order: red blood cell lysis (ACK lysing buffer, 2 mL, 5 minutes), formaldehyde fixation (4%, 500 μL, 30 minutes) and calcofluor white staining (25 μg/mL, 20 μL for 1 minute). Cells (50-100 per mouse) were imaged, and identified as *Cryptococcus neoformans* cells based on green fluorescent signal or cyan staining from calcofluor staining. Cells surface area and aspect ratio were measured in ImageJ and cells were classified as spores, intermediates, or yeast based on size and shapes parameters used in the quantitative germination assay.

Identifying Inhibitors of Germination and Growth

To identify inhibitors of *Cryptococcus neoformans* spore germination, a high throughput screen was developed that utilizes a nanoluciferase construct to monitor whether spores germinate in the presence of inhibitor. Briefly a protein luciferase construct was created resulting in a low luciferase signal for non-germinated spores and a high signal from germinated and replicating cells. The screen was coupled with $OD_{600}$ readings to monitor the ability of compounds to inhibit yeast replication.

The examples focused on FDA-approved drugs, as these drugs have the potential of being repurposed into antifungal therapeutics. To determine whether any FDA-approved drugs were able to inhibit *Cryptococcus neoformans* spore germination and yeast replication, the aforementioned high throughput screen was performed on the L1300 Selleck FDA-Approved Drug Library containing an array of 1108 compounds. This library of compounds is available commercially from Selleck Chemicals, 14408 W Sylvanfield Drive, Houston, TX 77014, USA.

The screening was successful at identifying known antifungal drugs as inhibitors of yeast replication as indicated by an $OD_{600}$ signal of less than 75% of the negative control (Table 2). For the purpose of these examples, antifungal drugs were defined as any FDA-approved drug used in the treatment of fungal infections. Of these 23 known antifungal drugs, only six (6) were identified as inhibitors of spore germination, indicated by a luciferase signal of less than 30% of the negative control. These germination inhibitors demonstrated normal nanoluciferase signal dose response curves (data not shown).

TABLE 2

Antifungal drugs used to treat fungal infections and their ability to inhibit *Cryptococcus neoformans* spore germination (based on luciferase signal) and yeast replication (based on $OD_{600}$).

| | Drugs | Germination Percent Luciferase Signal | Replication Percent $OD_{600}$ |
|---|---|---|---|
| Inhibitors of Germination (6) Less than 30% Luciferase Signal | Pentamidine HCl | 6.5 | 38.3 |
| | Bifonazole | 13.6 | 33.4 |
| | Econazole nitrate | 16.1 | 33.1 |
| | Isoconazole nitrate | 16.8 | 37.0 |
| | Tioconazoie | 25.0 | 36.8 |
| | Miconazole nitrate | 25.5 | 38.2 |

TABLE 2-continued

Antifungal drugs used to treat fungal infections and their ability to inhibit *Cryptococcus neoformans* spore germination (based on luciferase signal) and yeast replication (based on $OD_{600}$).

| | Drugs | Germination Percent Luciferase Signal | Replication Percent $OD_{600}$ |
|---|---|---|---|
| Non-inhibitors of Germination (17) | Butoconazole nitrate | 41.5 | 33.4 |
| | Fenticonazole nitrate | 49.1 | 36.4 |
| | Naftifine HCl | 55.5 | 34.5 |
| | Sulconazole nitrate | 57.8 | 40.9 |
| | Butenafine HCl | 57.5 | 32.9 |
| | Tolnaftate | 60.2 | 47.3 |
| | Liranaftate | 64.8 | 37.6 |
| | Clotrimazole | 65.9 | 34.1 |
| | Fluconazole | 84.0 | 72.2 |
| | Amphotericin B | 84.6 | 45.7 |
| | Amorolfine HCl | 88.6 | 41.4 |
| | Caspofungin acetate | 89.7 | 48.5 |
| | Climbazole | 151.5 | 38.9 |
| | Ketoconazole | 154.8 | 35.4 |
| | Itraconazole | 159.6 | 58.9 |
| | Posaconazole | 167.2 | 46.7 |
| | Voriconazole | 173.9 | 35.8 |

In addition to the antifungal drugs from the screen, 60 other inhibitors of yeast replication were identified, 16 of which were also inhibitors of spore germination (Table 3). These inhibitors have a wide range of clinical functions, including quaternary ammonium compounds ("QACs") and mammalian target of rapamycin ("mTOR" inhibitors (i.e.,) which are known to have broad effects on eukaryotic processes. Some drugs used in treating neurological diseases were also identified. Finally, antimicrobial and antihelminth drugs were also identified to inhibit germination. All compounds, with the exception of doxercalciferol, demonstrated appropriate nanoluciferase dose response curves (data not shown). Only a handful of compounds were pursued further in the examples due to limited availability of certain drugs. Representatives from each group, however, were selected for further characterization. Finally, five inhibitors of only germination were identified (see below).

TABLE 3

FDA-approved drugs able to inhibit spore germination and yeast replication. List of drugs, their ability to inhibit *Cryptococcus neoformans* spore germination (based on luciferase signal) and yeast replication (based on OD600), as well as their function as listed by L1300 Selleck FDA Approved Drug Library.

| | | Germination Percent Luciferase Signal | Replication Percent $OD_{600}$ | Function |
|---|---|---|---|---|
| Germination and Growth Inhibitors | Cetylpyridinium chloride | 4.2 | 31.9 | Infection |
| | Domiphen bromide | 4.4 | 63.9 | Infection |
| | Cetrimonium bromide | 4.4 | 63.2 | Infection |
| | Alexidine Hc1 | 4.6 | 29.6 | |
| | Otilonium bromide | 6.9 | 29.0 | Cardiovascular Disease |
| | Benzethonium chloride | 6.9 | 30.3 | Neurological Disease |
| | Niclosamide | 7.8 | 43.4 | |
| | PCl-32765 | 10.6 | 70.3 | Neurological Disease |
| | Everolimus | 15.7 | 67.7 | Cancer |
| | Doxercalciferol | 17.1 | 55.2 | Endocrinology |
| | Rapamycin | 18.5 | 61.8 | Immunology |

TABLE 3-continued

FDA-approved drugs able to inhibit spore germination and yeast replication. List of drugs, their ability to inhibit *Cryptococcus neoformans* spore germination (based on luciferase signal) and yeast replication (based on OD600), as well as their function as listed by L1300 Selleck FDA Approved Drug Library.

| | Germination Percent Luciferase Signal | Replication Percent $OD_{600}$ | Function |
|---|---|---|---|
| Temsirolimus | 21.3 | 59.2 | Cancer |
| Ezetimibe | 22.0 | 51.3 | Cardiovascular Disease |
| Dequalinium chloride | 22.3 | 47.9 | |
| Disulfiram | 22.7 | 65.6 | Neurological Disease |
| Biperiden HCl | 23.4 | 56.6 | Neurological Disease |

Together these results give a set of compounds that are germination inhibitors and replication inhibitors that can be further investigated as potential targets for repurposing or to elucidate germination processes. Inhibitors of both germination and yeast replication were prioritized for further study.

Antifungal Drugs are Inhibitors of Fungal Pathogen Vegetative Growth:

To confirm the ability of the known antifungals to inhibit yeast replication, minimum inhibitory concentration (MIC) and minimum fungicidal concentration (MFC) testing was performed on the top three germination inhibition hits. All three antifungal compounds inhibited replication of *Cryptococcus neoformans* yeast of both serotype A and D, while being less potent against *Candida albicans* (Table 4). All of the antifungal drugs were fungicidal with the exception of bifonazole against H99.

TABLE 4

Ability to inhibit fungal pathogens of antifungal drug germination-inhibitor hits. MIC/MFC values of top three germination inhibitors against prominent human fungal pathogens.

| | *Cryptococcus neoformans* (JEC21) | | *Cryptococcus neoformans* (H99) | |
|---|---|---|---|---|
| | MIC (μg/mL) | MFC (μg/mL) | MIC (μg/mL) | MFC (μg/mL) |
| Pentamidine isethionate | 1.56 | 3.13 | 6.25 | 6.25 |
| Bifonazole | 6.25 | 6.25 | 6.25 | >100 |
| Econazole nitrate | <0.78 | 6.25 | <0.78 | 6.25 |

| | *Candida albicans* (SC5314) | | *Aspergillus Fumigatus* (AF293) |
|---|---|---|---|
| | MIC (μg/mL) | MFC (μg/mL) | MIC (μg/mL) |
| Pentamidine isethionate | 50 | 50 | >100 |
| Bifonazole | >100 | >100 | >100 |
| Econazole nitrate | 6.25 | 12.5 | 3.13 |

Pentamidine and bifonazole were unable to inhibit *Aspergillus fumigatus* while econazole nitrate was able to inhibit its growth. It is important to note the *Aspergillus fumigatus* inhibition testing is performed on conidia, their asexual spore (Table 4). Together these results confirm the ability of these antifungals to inhibit fungal growth in a fungicidal manner.

Antifungal Drugs are Inhibitors of Fungal Spore Germination:

Once yeast replication inhibition was confirmed, the ability of the drugs to inhibit spore germination was characterized using a quantified microfluidics-based germination assay where the changes in size and morphology are monitored as small ovoid spores germinate into large circular yeast.

Pentamidine isethionate was able to successfully inhibit spore germination as seen by a decrease in morphology transition (data not shown). While germination is not completely halted, the spores were only able to circularize partially and unable to transition into the yeast state. It is important to note that all of the spores were inhibited, indicating that none of the ~10,000 spores showed inherent resistance and escape from inhibition. Due to the hydrophobic nature of bifonazole and econazole nitrate, the PDMS devices resulted in sequestration of the compounds and the assays could not be performed in the microfluidic devices. To determine if these compounds had an effect on spore germination, the assay was performed outside of the microfluidic device and imaged at 0 and 16 hours. Both econazole nitrate and bifonazole were able to inhibit spore germination effectively with spore escape apparent in bifonazole-treated spores as determined by a yeast population increase. None of these drugs were fully germicidal at these concentrations. These assays confirm that the high throughput screen identified antifungal drugs that are potent inhibitors of spore germination.

FDA Drug Hits are Inhibitors of Fungal Pathogen Vegetative Growth:

To determine the ability of the 16 non-antifungal drugs to inhibit yeast growth, MIC and MFC testing was performed on nine of the 16 drugs. The nine drugs were selected based on dose response curves, drug availability and ensuring that all classes of inhibitors were tested. Seven inhibitors were able to inhibit yeast replication to varying degrees (Table 5) while biperiden HCl and ezetimibe, were unable to inhibit yeast growth (data not shown). All drugs were tested against *Aspergillus fumigatus* with varying degrees of success. Notably alexidine was extremely potent against *A. fumigatus*. Additionally, cetylpyridinium bromide, otilonium bromide, benzethonium chloride and disulfiram were all able to inhibit *A. fumigatus*. (Table 5)

TABLE 5

Ability to inhibit fungal pathogens of FDA drugs germination-inhibitor hits. MIC/MFC values of germination inhibitors against prominent human fungal pathogens.

| | *Cryptococcus neoformans* (JEC21) | | *Cryptococcus neoformans* (H99) | |
|---|---|---|---|---|
| | MIC (μg/mL) | MFC (μg/mL) | MIC (μg/mL) | MFC (μg/mL) |
| Cetylpyridinium chloride | <0.78 | <0.78 | <0.78 | <0.78 |
| Alexidine HCl | <0.78 | <0.78 | <0.78 | <0.78 |
| Otilonium bromide | 3.13 | 3.13 | 3.13 | 3.13 |
| Benzelthonium chloride | 3.13 | 3.13 | 3.13 | 3.13 |
| Niclosamide | <0.78 | 1.56 | 1.56 | >100 |
| Temsirolimus | 6.25 | 6.25 | 6.25 | 6.25 |
| Disulfiram | 3.13 | 3.13 | 6.25 | 6.25 |

| | *Candida albicans* (SC5314) | | *Aspergillus Fumigatus* (AF293) |
|---|---|---|---|
| | MIC (μg/mL) | MFC (μg/mL) | MIC (μg/mL) |
| Cetylpyridinium chloride | 1.56 | 3.13 | 1.56 |
| Alexidine HCl | <0.78 | <0.78 | <0.78 |
| Otilonium bromide | 3.13 | 3.13 | 6.25 |
| Benzelthonium chloride | 6.25 | 12.5 | 12.5 |
| Niclosamide | >100 | >100 | >100 |
| Temsirolimus | 1.56 | 1.56 | >100 |
| Disulfiram | 6.25 | 12.5 | 25 |

These results indicate that these FDA-approved drugs have the ability to inhibit fungal pathogen vegetative growth and kill fungal cells. While some of these drugs have previously been shown to have antifungal activities, some have not.

FDA Drug Hits are Inhibitors of Fungal Spore Germination:

To determine the ability of these seven drugs, which inhibit fungal vegetative growth, to inhibit spore germination; germination assays were performed on the drugs at a concentration of 25 μg/mL. All seven of these drugs were able to inhibit germination to different extents (data not shown).

Five of the seven drugs were tested in microfluidic devices. Alexidine hydrochloride, an antimicrobial, and otilonium bromide, an antimuscarinic used to treat irritable bowel syndrome, were both able to completely inhibit spore germination, as seen by the lack of change in morphology. Both of these drugs were fully germicidal. Niclosamide, an antihelminth that inhibits oxidative phosphorylation, was also able to completely inhibit germination, but was not fully germicidal. Temsirolimus, an mTOR inhibitor used in some cancer treatments, was able to partially inhibit germination and appeared to stall germination strongly between 6 and 8 hours. When spores were exposed to temsirolimus they were able to circularize but appeared to have difficulty growing in size. Finally, disulfiram, an alcohol dehydrogenase inhibitor used in the treatment of alcoholism, was a weak inhibitor of germination leading to about a 2-hour stall in germination overall at this concentration. At higher concentrations, a similar stall to that observed with temsirolimus was observed (data not shown). Neither temsirolimus nor disulfiram were germicidal.

Cetylpyridinium chloride and benzethonium chloride, both quaternary ammonium salts, were unable to be tested in the microfluidic devices due to their viscosity and were therefore tested in outside the devices and imaged at 0 and 16 hours. Both drugs were able to inhibit spore germination completely and were fully germicidal at this concentration. These assays confirm that the method disclosed herein has utility to identify a variety of non-antifungal, FDA-approved drugs that are able to inhibit fungal spore germination to varying degrees. These results also start to elucidate potential molecular processes crucial for fungal spore germination.

Pentamidine Ubiquitously Slows Germination:

Pentamidine was selected for further study due to many factors that make it a good candidate for repurposing. A range of concentrations of pentamidine isethionate was tested in a germination assay. As concentrations of pentamidine increased, spore germination became slower. However, no individual spores were able to escape inhibition, as seen by the lack of spores in the yeast state at higher concentrations. While pentamidine was not germicidal at lower concentration, at 50 μg/mL pentamidine showed germicidal activity. These results suggest that pentamidine slows the germination of spores ubiquitously and at high enough concentrations is sporicidal.

Figure 8B:
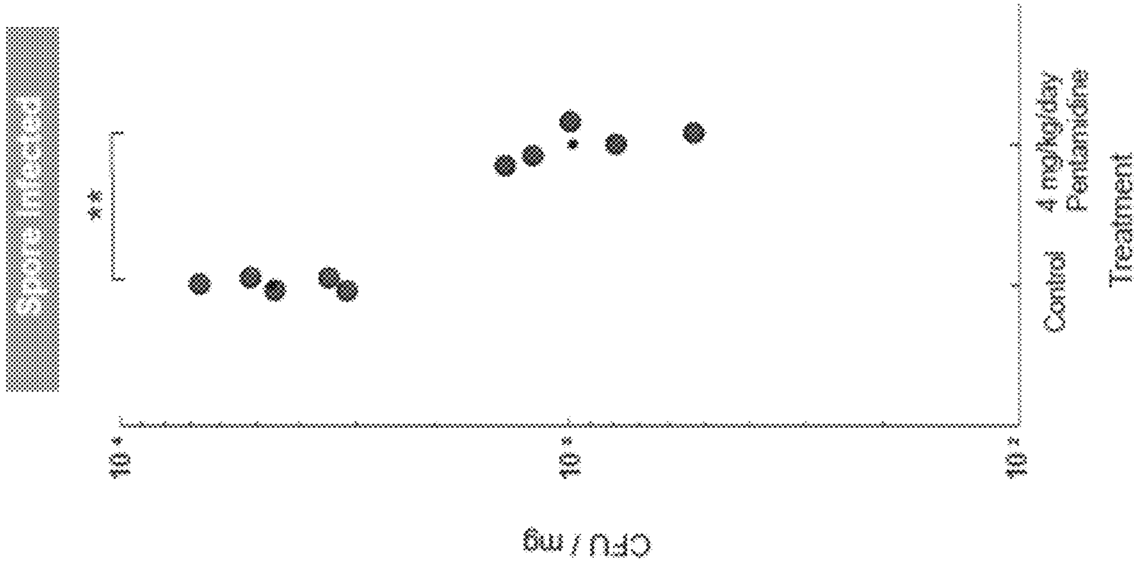
FIGS. 8A and 8B show that pentamidine treatment lowers fungal burden in mouse lung.
Figure 8A:
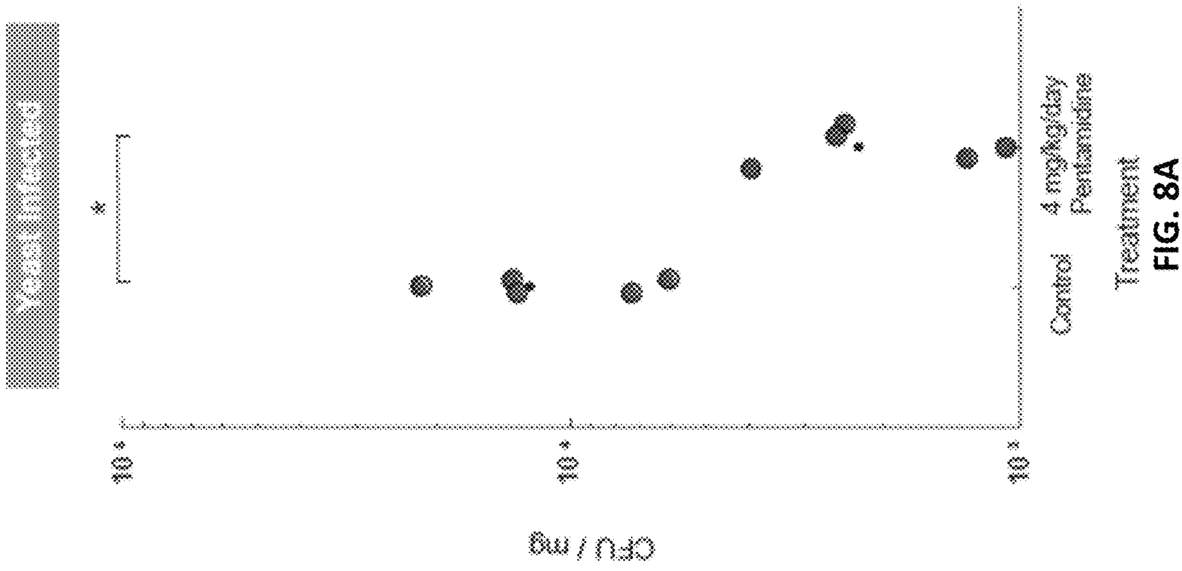

Pentamidine Treatment Lowers Fungal Burden in Mouse Lung:

Pentamidine is a successful inhibitor of *Cryptococcus neoformans* yeast replication in vitro. For repurposing potential, it is important to determine drug efficacy in vivo. For this purpose, the ability of pentamidine to lower the fungal burden in mouse lungs infected by both spores and yeast was determined. One-day post-infection intranasal dosing was begun at 4 mg/kg/day and the mice were treated for three consecutive days. On the fourth day post-infection, lungs were collected and fungal burden was determined. Pentamidine-treated mice had significantly lower fungal burdens in the lung than PBS-treated mice, in both yeast- and spore-infected mice. See FIG. 8A and FIG. 8B, respectively. These results indicate that pentamidine is able to inhibit yeast replication in vivo.

Figure 9:
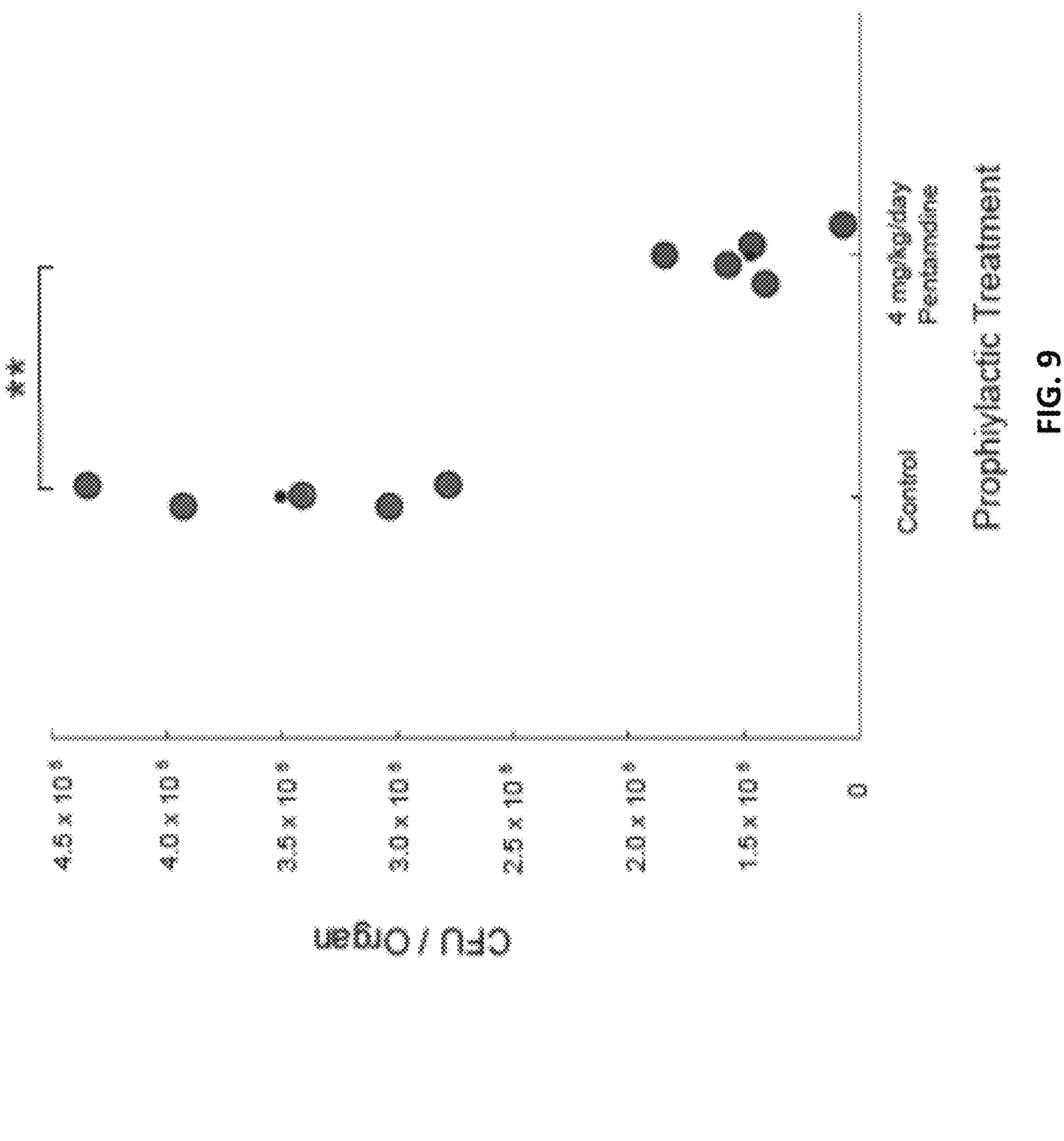
FIG. 9 is a graph showing that pentamidine prophylactically inhibits fungal spore germination in vivo.

Prophylactic Pentamidine Inhibits Spore Germination In Vivo:

Pentamidine is a successful inhibitor of spore germination in vitro. It is important, though, to determine drug efficacy in vivo. Therefore, the ability of pentamidine to inhibit germination of spores in mouse lungs was determined. To determine if prophylactic pentamidine had an effect on fungal lung burden, mice were treated with 4 mg/kg/day of pentamidine or 1×PBS for three consecutive days. After three days of infection, mice were infected with JEC20×JEC21 spores and 4-days post infection, mouse lungs were collected and lung fungal burden was determined. The results are shown in FIG. 9. As evidenced by data in FIG. 9, pentamidine prophylaxis was successful in decreasing spore-mediated lung burden. These results indicate that spore germination was inhibited in vivo.

In vivo spore germination has never been characterized mainly due to technical hurdles. Using a novel assay, *Cryptococcus neoformans* cells were recovered from prophylactically treated, spore-infected mouse lungs 8 hours post infection. This was an early enough time point where no budding yeast were recovered from mouse lungs, ensuring that all cells were spore derived and not budding derived. Based on size and shape of the cells, the level of in vivo spore germination was quantified. Prophylactic pentamidine was able to inhibit spore germination as indicated by a higher spore percent and a lower yeast percent in pentamidine-treated mice. Together these results demonstrate that prophylactic pentamidine has in vivo activity against *Cryptococcus neoformans* spores, indicating it is useful to prophylactically treat (i.e., prevent) fungal infection.

SEQUENCE LISTING

```
Sequence total quantity: 68
SEQ ID NO: 1            moltype = DNA  length = 804
FEATURE                 Location/Qualifiers
source                  1..804
                        mol_type = genomic DNA
                        organism = Cryptococcus neoformans
CDS                     1..804
SEQUENCE: 1
atgtctgacg acggacaagt acaaagggga aaggccggca ttagctggcc ggctcaagaa  60
ctaacctcgg atcccattgc caaattcttc cagtacggct ctaaactctc atggcactgg  120
aactggacca agcattggaa gggccctctg gtgccggaga cctctgacga ccttgagatt  180
gacgcagaat ttgtgcccat gatctggtca ccccaatctt tagatgatgg ttgcgacttg  240
caagaaggat ggaatcttct cttgggtttc aacgagcctg acctcgacaa cgaagctgtt  300
gcaagccatc gctctccgca ggaagctgca gacgcgtgga tccagctggc acaactccgt  360
accgatccag acaaccagca cctcgtttcc cccgctgtag catccaacgt ggaatggctt  420
aaagagttcc tctccctgat tccagaagac acttatcccg cctacttggc tgtgcacctc  480
tacacaacca cttttgatga ttttgtcggc aagatggaga tgtaccacaa cgagtttgga  540
ttgcctatta tcttgactga attctgcatg cagagttggg acgaaggtgt tccaggccca  600
gaggaccagc agcaagtcca tgattacatg ggccaaacaa caaaatggct tgatgaaact  660
gactatgtta ttaagtactg ttggtttggc gctgttcgtg atacggcgaa cttgcacgac  720
gtccacccct tcaaccgact catggatgaa aacggcgaga ttaccccatt gggtttccaa  780
tacatgtatg gtgggcatga gtaa                                        804

SEQ ID NO: 2            moltype = AA  length = 267
FEATURE                 Location/Qualifiers
source                  1..267
                        mol_type = protein
                        organism = Cryptococcus neoformans
SEQUENCE: 2
MSDDGQVQRG KAGISWPAQE LTSDPIAKFF QYGSKLSWHW NWTKHWKGPL VPETSDDLEI  60
DAEFVPMIWS PQSLDDGCDL QEGWNLLLGF NEPDLDNEAV ASHRSPQEAA DAWIQLAQLR  120
TDPDNQHLVS PAVASNVEWL KEFLSLIPED TYPAYLAVHL YTTTFDDFVG KMEMYHNEFG  180
LPIILTEFCM QSWDEGVPGP EDQQQVHDYM GQTTKWLDET DYVIKYCWFG AVRDTANLHD  240
VHPFNRLMDE NGEITPLGFQ YMYGGHE                                     267

SEQ ID NO: 3            moltype = DNA  length = 1821
FEATURE                 Location/Qualifiers
source                  1..1821
                        mol_type = genomic DNA
                        organism = Cryptococcus neoformans
CDS                     1..1821
SEQUENCE: 3
atgtcgaccc ttcccattta tcaccccgtt ccaacggacg agaaacaccc aatatctgcc  60
actttggtag acggcgagtt tgaccctcgc tacattcatc ccgccgcaat cggctctcaa  120
tacctttata ttggcggtcc ccgcagcgcc tatcaggccg cgaaggacaa gtacgctggc  180
ttgtccaaag tcaagaaagg tctcctcgct cttgccgttg tttggttcgg tcttgtcgtt  240
ggccatcagg ctgcgcgtct tgctggcggc aaatgccacc aggacgctca tcatgctccc  300
gccgaatttg gcgtgaagca gtggagagac cactcatctc atcgatttgg tggccctatc  360
ttcctcgagg atggtccact tgactgtcat ggtggccgta aagaccgtgc tcctgaggag  420
ctttcttccg ttgccactgt ctacgagtcc atcaacgttg tcgggagcaa cgatgctacc  480
gacattctct ccgccaacgc ctctttccct ctcaaacttg gccgtggcaa gcactttgat  540
ctcaccttcc aaggtgaggg taacgtcatc atctcgaggg ctgaggagga gtctgaagac  600
tctactgtca acgtttttgt tgagtctact tggtccggtg aggaggctga aggggtcaag  660
atgttgtctg gaaaacactc tcacgctctc tctgttgctt cttctcaatc ctcgtctcat  720
attgtccacc ttgttcttcc tgccaacaag aagcgtcttc cttccatctc tatcttttct  780
accaaggacc ttactcttga tatccatcca tctgttcagg acatccacgt gggaaagctc  840
tccctcaagt ctgagagcgg tgatatcaag cttcctaccc tcgctgtcaa caagctcgtg  900
gctgagaccg taaccggtga cgtcggcggt aacttcaacg tcagcaactc tttcgttgtc  960
aagacagtca caggtaacat taacgccatt gttaacgttg ttcctcactc cccacctaag  1020
gacaagctta accttcataa cgttgatgcc aagcacgagc acaagaagtt tgacagccgt  1080
cacggagaac acaatcacga gaagaagcac ttcggagggc gtttccactc tgaagaagag  1140
cgaccttcca agtggtctct caatattttc aagtctaaga aagaggatga gcctgaacac  1200
cctccccccc ctccggtctt tatcggcgct ttctccacct ctggcaacat tcttctcaag  1260
gtcttcggtt ctcccaacgt ctctactgat actaatgtct tctcccatac cggtgacgtc  1320
gacgttaccc atgacaagtc attccacggt ttgtacgagg tcggcagctt aaagggcacc  1380
tatgatgttg tcgtgaggga cggcaaggtg catcgagtcc tggaggaata cgtcactgag  1440
gagggaggca agcagaaggg ccttgccttc gttcccaaga acagaaagac tgagggctcc  1500
cacgagaaga ggcacttccg caatgctgaa agcgttgatg gcgagcttcc ccctccccct  1560
cctggtaagg gccacggtcc tgatggtccc gatggtcctg atggtcctgg aggtcctagt  1620
ggtcctggag gtcctggtgg tcctgatggt cctggtggtc ctggtggtcc tggtggccct  1680
ggaggtcccg gtggtcccgg tggtcccggt ggtcccggcc ccgaccaccc ccgtggtcct  1740
cctccttggg ttgtcttccc ccccggtcac tcagaagtct tcgtccacac tgaagttggc  1800
aacgccaaga ttgtcctcta a                                           1821

SEQ ID NO: 4            moltype = AA  length = 606
FEATURE                 Location/Qualifiers
source                  1..606
                        mol_type = protein
```

```
                         organism = Cryptococcus neoformans
SEQUENCE: 4
MSTLPIYHPV PTDEKHPISA TLVDGEFDPR YIHPAAIGSQ YLYIGGPRSA YQAAKDKYAG  60
LSKVKKGLLA LAVVWFGLVV GHQAARLAGG KCHQDAHHAP AEFGVKQWRD HSSHRFGGPI  120
FLEDGPLDCH GGRKDRAPEE LSSVATVYES INVVGSNDAT DILSANASFP LKLGRGKHFD  180
LTFQGEGNVI ISRAEEESED STVNVFVEST WSGEEAEGVK MLSGKHSHAL SVASSQSSSH  240
IVHLVLPANK KRLPSISIFS TKDLTLDIHP SVQDIHVGKL SLKSESGDIK LPTLAVNKLV  300
AETVTGDVGG NFNVSNSFVV KTVTGNINAI VNVVPHSPPK DKLNLHNVDA KHEHKKFDSR  360
HGEHNHEKKH FGGRFHSEEE RPSKWSLNIF KSKKEDEPEH PPPPPVFIGA FSTSGNILLK  420
VFGSPNVSTD TNVFSHTGDV DVTHDKSFHG LYEVGSLKGT YDVVVRDGKV HRVLEEYVTE  480
EGGKQKGLAF VPKNRKTEGS HEKRHFRNAE SVDGELPPPP PGKGHGPDGP DGPDGPGGPS  540
GPGGPGGPDG PGGPGGPGGP GGPGGPGGPG GPGPDHPRGP PPWVVFPPGH SEVFVHTEVG  600
NAKIVL                                                           606

SEQ ID NO: 5             moltype = DNA  length = 594
FEATURE                  Location/Qualifiers
source                   1..594
                         mol_type = genomic DNA
                         organism = Cryptococcus neoformans
CDS                      1..594
SEQUENCE: 5
atgcgtttta cttctatcat cgttgccgct cttccgcttg tcggctctgt cttcgctgcc  60
cccttcgctg agaaggattc tatcgcttct tccccgact tggtcaagaa ggaggttaac  120
gtcctctctg tcgtcaatga agtccagtct agggttaatg ctgctgccgc catgccccgc  180
cagtctcaag cggatgttga ggcctgtctc aacactgtca ttgatgcctt taactggtgc  240
ggtggccagc tcggtattga cgtttccgcc agcgccagcg ccaatgccgg tgctagcatc  300
cattacttgc gtcgtgagat tattgcccgt gatgacgaca aggaggctgt tgctcaggca  360
ctctctagcg ttgttcagac cgttaatgtc ggcatcgtcc agcagatccc cagccaattc  420
atcaacatcc ctggcgtctc caaccttgtt aaccagcttg acattgctct cagtctcatc  480
cttaagggtg ttgacgctat tctcgccggt gtcctctacc tcgtcaaggc ccttctcatc  540
gatgttggca tcatcctcga ctcgcttctc ggcggtctcc tttccatcct ttaa        594

SEQ ID NO: 6             moltype = AA  length = 197
FEATURE                  Location/Qualifiers
source                   1..197
                         mol_type = protein
                         organism = Cryptococcus neoformans
SEQUENCE: 6
MRFTSIIVAA LPLVGSVFAA PFAEKDSIAS SPDLVKKEVN VLSVVNEVQS RVNAAAAMPR  60
QSQADVEACL NTVIDAFNWC GGQLGIDVSA SASANAGASI HYLRREIIAR DDDKEAVAQA  120
LSSVVQTVNV GIVQQIPSQF INIPGVSNLV NQLDIALSLI LKGVDAILAG VLYLVKALLI  180
DVGIILDSLL GGLLSIL                                               197

SEQ ID NO: 7             moltype = DNA  length = 894
FEATURE                  Location/Qualifiers
source                   1..894
                         mol_type = genomic DNA
                         organism = Cryptococcus neoformans
CDS                      1..894
SEQUENCE: 7
atgtctgccg tcgaagcacc ctccgcctcg caggccatct ggcccgagct cactgaagac  60
caccccettt cgcagctcaa ctctcgcctc cctactatcc tttcagaggc tggtcactcc  120
caaatctggg gcgttactct tacttactcc actccccaa ccttctctag ccttattatt  180
ctgcaaaaat tccttcgttc cgtggataat aacgtggatg aggctgccac ggctctaggc  240
aagacactca agtggcggaa ggactgggga ttggacgcgc gggcggacaa aaaagagaag  300
gaaaactttg ggcccgattt tgaaggctta ggatatgtga ccaagatcaa gaaaaatgat  360
ggcggagatg agatcgtgac ttggaacgtt tatggagctg tgaaggattt gaaatcgacc  420
tttggggatc ttgaccgatt ccttcgatgg cgtgtcaatc ttatggagga ggctatcgcc  480
catcttcatc tcgctaccac ctctactccc atcccagact ttaacgccgg tattgatccc  540
catcgcatgg cacaagtcca tctatatgaa ggtgtctcat tccttcgcat ggatcctcat  600
gtgaaagctg cctccaaggc aaccattgag cttatggcgg ccaactatcc cgaacttctt  660
tctcgcaaat tctttgtggg cgtgcctttg ataatgagct ggatgtttca ggccgtgcga  720
atgttcgttt ccgctgagac tgccaagaag tttgtggtca ttagctacaa ggagaatctg  780
gcgaatgagc tgggagaact tgaaggtgtg cccaaggagt atggtggaaa gggtctcagt  840
ttgggcgaac ttcagaacca gctgcgaggg gaggacgcgg tgacttcttc gtaa        894

SEQ ID NO: 8             moltype = AA  length = 297
FEATURE                  Location/Qualifiers
source                   1..297
                         mol_type = protein
                         organism = Cryptococcus neoformans
SEQUENCE: 8
MSAVEAPSAS QAIWPELTED HPLSQLNSRL PTILSEAGHS QIWGVTLTYS TPPTFSSLII  60
LQKFLRSVDN NVDEAATALG KTLKWRKDWG LDARADKKEK ENFGPDFEGL GYVTKIKKND  120
GGDEIVTWNV YGAVKDLKST FGDLDRFLRW RVNLMEEAIA HLHLATTSTP IPDFNAGIDP  180
HRMAQVHLYE GVSFLRMDPH VKAASKATIE LMAANYPELL SRKFFVGVPL IMSWMFQAVR  240
MFVSAETAKK FVVISYKENL ANELGELEGV PKEYGGKGLS LGELQNQLRG EDAVTSS     297

SEQ ID NO: 9             moltype = DNA  length = 2094
```

-continued

```
FEATURE                Location/Qualifiers
source                 1..2094
                       mol_type = genomic DNA
                       organism = Cryptococcus neoformans
CDS                    1..2094
SEQUENCE: 9
atgtcagagc tattcaagga catcccagag tttgtagaga ccgacatcgg agagagcctt  60
gcagccagaa cggaaaccct tggctccttc agagaactag gccctccaga cctctgccat  120
gttatgaaag tttatgggaa accgccgact caacgagaga tcgggtccta tcactactgc  180
tctggaatag aggcttcgtc ctctgcgtca ctcgctgcct atctcaactc tttgcagttt  240
tcagtggaag attcgtctgc atggtttggc aaggggtcgg catggaaagt tcgaagcggg  300
acgtattgct gcttcaatgc cttttcacgg gtagatatgc gggtggaagc caatattccc  360
ggcggtgtcg acgcttttgt ggttgatctt cacggtcaaa gacaccctgc gacccccgag  420
ctctggcaag agacgtacct gtctgcgatc ctgcgtgcta ttagatatgc ggacgatgcc  480
tcctataggt tggcagggta tagaaagctg gatccgatca caacgccaga agcagaggaa  540
agattcctca aagccgccga agcgctgttc ttcaagggct ggcagcttgg ctcagatccc  600
gaaatacagg tcgccacagt tgtcaccaac cacctgacct ctgccattct taaatacttt  660
tccgactctt tcagacttca tcgagccgcc aacctttttcg aaaggatgat ggacaaggag  720
ccagaggtag ccgctctagt ggcgaagagt tacatcggca tgaacgagga gatcaaagct  780
gtcaagatca tgaacgctgc ccttgccgcc aatcctcaat cctatcccat ccttcatgcc  840
caagtcgatt tcctcctttc caagcacaaa tacgaatggg cccagcaagt cgcccagcag  900
gcggtcaatt ctgcacccag cgagttcacg acttgggcca aactcacgga gacgtacatc  960
gagttggggc aactcgacca ggctttgttg acactcaact catgtccaat gtttacttat  1020
aacgaaagag atctccatcg gatgcctacc cctgcaaagt ccaatatgcc agtcaagaag  1080
tttatcgcag actccaattt ggtggatgaa gattcgtcac gagagaacga ggccgatatc  1140
gctctcctcc gtctccccgc tcccaacctc cgcggcacat tcgccaaagc gtactccctc  1200
ctcactctcc ttgtctctaa gattggttgg gatgagcttc tcaaaattag atcctccgtc  1260
ttcgtcatgg aagaggaata tcggctgcat aaaacgaacg tttctgttga tatgaatggc  1320
gaagcgggtg acggcgcgtc cattgcgggc ttgaagagga cctcgtccga agaggtcaac  1380
actcccagcg atatacctac catcaggata tcaagcgagt cgatgcgcac tcctaatacg  1440
gctccaggac cagggttcag cgaaaaggca agtactcaca agcccgctct ggagaagccc  1500
gagacagcac aagcgaatga agatcccaat tcgcctttgg ggatgaagag tgaaggggaa  1560
cagccggttt cggcgttttc tcataagcga ttatgtgaga gatggttaga taacctcttt  1620
ttagttctgt atgaagactt gagagtctac accatttgga gagcagagat atctcatttc  1680
aaaacccagc acatgtcata ccgaaagact ggtaccgagt gggagatcct tggtgaactt  1740
gccacacgtt tgcatcacaa agaagaagcc aaggacgcgt accaacgctg tctcgactcc  1800
aaattcagcg caaaagcact tatgaagctt cttgaaacgt atgcgaatga gggcgatctt  1860
caaaagacct tgacggcggc tgtgaggctg acaacctatc accatcgatg gtatatggac  1920
gcgtcatacc cgtccatggt cgcgcattat ttgtacaagg tcggactcat acatggacat  1980
gccaaattac aatacacaat gctcagtatg aacctgccgg tcgggatctt tgaaataatg  2040
caaggctata tgaaatacgg ggcgacgttc aacgtcgaag gttcagaatt ctag        2094

SEQ ID NO: 10          moltype = AA  length = 697
FEATURE                Location/Qualifiers
source                 1..697
                       mol_type = protein
                       organism = Cryptococcus neoformans
SEQUENCE: 10
MSELFKDIPE FVETDIGESL AARTETLGSF RELGPPDLCH VMKVYGKPPT QREIGSYHYC  60
SGIEASSSAS LAAYLNSLQF SVEDSSAWFG KGSAWKVRSG TYCCFNAFSR VDMRVEANIP  120
GGVDAFVVDL HGQRHPATPE LWQETYLSAI LRAIRYADDA SYRLAGYRKL DPITTPEAEE  180
RFLKAAEALF FKGWQLGSDP EIQVATVVTN HLTSAILKYF SDSFRLHRAA NLFERMMDKE  240
PEVAALVAKS YIGMNEEIKA VKIMNAALAA NPQSYPILHA QVDFLLSKHK YEWAQQVAQQ  300
AVNSAPSEFT TWAKLTETYI ELGQLDQALL TLNSCPMFTY NERDLHRMPT PAKSNMPVKK  360
FIADSNLVDE DSSRENEADI ALLRLPAPNL RGTFAKAYSL LTLLVSKIGW DELLKIRSSV  420
FVMEEEYRLH KTNVSVDMNG EAGDGASIAG LKRTSSEEVN TPSDIPTIRI SSESMRTPNT  480
APGPGFSEKA STHKPALEKP ETAQANEDPN SPLGMKSEGE QPVSAFSHKR LCERWLDNLF  540
LVLYEDLRVY TIWRAEISHF KTQHMSYRKT GTEWEILGEL ATRLHHKEEA KDAYQRCLDS  600
KFSAKALMKL LETYANEGDL QKTLTAAVRL TTYHHRWYMD ASYPSMVAHY LYKVGLIHGH  660
AKLQYTMLSM NLPVGIFEIM QGYMKYGATF NVEGSEF                           697

SEQ ID NO: 11          moltype = DNA  length = 1662
FEATURE                Location/Qualifiers
source                 1..1662
                       mol_type = genomic DNA
                       organism = Cryptococcus neoformans
CDS                    1..1662
SEQUENCE: 11
atgtcgttag cggacgccct tctggcagac cttgatggtc tctcggatga cgaagctcga  60
tctccttctc ctggccccga ggcctcctcc tcgtcaatgc cgcctcctgg tttgcccaac  120
aaaggaaaac gtcccgccag cgctatggaa gtcgatgatg gcgaaggagg tgcgaatgaa  180
gatgagggag acgatatgaa gctggaagac gggacgagtg ctgtgggatt tgtacctgaa  240
ggaggtgtaa ggcctgcaga tgagctggac aaggaggaag tggaaaaaac cgatatgaag  300
ggtgtcgagg atgtgaagaa agtagccagg ttggcaggaa gccagaagct tcgagatgtt  360
ctggcagata tcataaaata caccgagtct cccaccgata tgtcttcgtc tgccggtccc  420
ctcgaggaga atccagagta ccatcttgtt gtcactgcga acaacatgtc cgtcgaggtt  480
gacaacgaga ttctcatcgt gcacaaattc attcgtgacc actatgctcc tcgatttccg  540
gaactcgaac agctcattgc cgaaccttgg acatacattg ccgccgttaa tgccatcggt  600
cagtctgaag atctaacgaa ggtcacattc cccaacaccc tccctgcggc tactgtactc  660
```

-continued

```
tctatcactc ttactgctac gacttcccgt ggtcggccgc tcacgcctgc agagtgggaa  720
acaattcagc gcgccatcgc tgtcgcccaa aatctccgtt cggcgcgaga acaaattttt  780
tcctacgtcg agtcccgtat ggctgctgta gcacctaatt tgtctgctat tgtgggcacc  840
ggtatcgctg ccaaattact tggtttagca ggtggtctcc atgcgtttag tcgacagccg  900
agttgtaatg tgatgctttt tggcgcgatg aagaagactt tggccacctc tcatctttct  960
gctgcctctc agcaacgaca taccggcttt atcttccaaa gctctatagt acagagtgcc  1020
cagcctgaag atcgaagaag agctcagcga gcggtgtctg ccaagtgtgc tcttgcggcc  1080
aggatcgatg caggaaaggg gtctagggac ggatcttatg gaagaaaggtg tttggcggat  1140
ttgcaaaaga ggattgaaaa gatggcggaa cctcctccca acaagatgat caaggcgttg  1200
cctatccctc aggagactaa caggaagaag cgtggtggta agagagctcg aaaagccaag  1260
gaagcgtacg cccagaccga attgagaaag ttacaaaacc gaatggagtt tggcaaggcg  1320
gaagaagaga tcggggtgga cgacgagact gttgggtttgg gtatgatcgg ttccgccgga  1380
agggtccgag gcgagatggc agatgcgagg agtaaagcta aactttctcg agccaacaaa  1440
cttcgaactc agctccttgg tcgctcagtc acatccaacg acgctgccag cggtatggcc  1500
acctccttat cattcacgcc tgtccaaggt cttgaaatag ttacaccctc cctctctgca  1560
gcccagaaag tacaggctgc gaatgacaga tggttctccg gggtacatt tacgcatgta  1620
aggaaggggg gaagcagtat tccgggacag gaacagaaat ag                    1662
```

```
SEQ ID NO: 12          moltype = AA  length = 553
FEATURE                Location/Qualifiers
source                 1..553
                       mol_type = protein
                       organism = Cryptococcus neoformans
SEQUENCE: 12
MSLADALLAD LDGLSDDEAR SPSPGPEASS SSMPPPGLPN KGKRPASAME VDDGEGGANE  60
DEGDDMKLED GTSAVGFVPE GGVRPADELD KEEVEKTDMK GVEDVKKVAR LAGSQKLRDV  120
LADIIKYTES PTDMSSSAGP LEENPEYHLV VTANNMSVEV DNEILIVHKF IRDHYAPRFP  180
ELEQLIAEPW TYIAAVNAIG QSEDLTKVTF PNTLPAATVL SITLTATTSR GRPLTPAEWE  240
TIQRAIAVAQ NLRSAREQIF SYVESRMAAV APNLSAIVGT GIAAKLLGLA GGLHAFSRQP  300
SCNVMLFGAM KKTLATSHLS AASQQRHTGF IFQSSIVQSA QPEDRRRAQR AVSAKCALAA  360
RIDAGKGSRD GSYGRKCLAD LQKRIEKMAE PPPNKMIKAL PIPQETNRKK RGGKRARKAK  420
EAYAQTELRK LQNRMEFGKA EEEIGVDDET VGLGMIGSAG RVRGEMADAR SKAKLSRANK  480
LRTQLLGRSV TSNDAASGMA TSLSFTPVQG LEIVTPSLSA AQKVQAANDR WFSGGTFTHV  540
RKGGSSIPGQ EQK                                                    553
```

```
SEQ ID NO: 13          moltype = DNA  length = 759
FEATURE                Location/Qualifiers
source                 1..759
                       mol_type = genomic DNA
                       organism = Cryptococcus neoformans
CDS                    1..759
SEQUENCE: 13
atgtcatcaa ctgatctcgg aggccaagct gccgtcatca ctggcggtgg taagaatctt  60
ggtgctttga ttgcgaagac tctcgccaag cagggagtca acgttgcgat ccattacaac  120
tcggccagtt ccaagtccga gacagaagct acattgaaga cactcggatc gtatggggtc  180
aaagccgctg ctttccaggc caatcttacc actgaggcat cagttgagaa actcttctca  240
gacgcagcag ctgctcttgg agtgtccaag ttcgatatcg ccatcaatac ggtcggtaag  300
gttcttaaaa agcctatcgt tgaaacaaca gagcaaggat tcgacgacat gttcctagtc  360
aactcaaagt gtgccttctt ttttatcaag catgcggcca agaatctcaa cgagggggc  420
acgattatat cactcgtgac ttcactcctt ggagcatttg cgcctggtta ttcaacttat  480
caaggcagta aagctcctgt agagtggttc actaagtcgg ctgccaagga gcttcagcct  540
aagaatatta gggtcaactg tgtggctccg gggccaatgg acactccctt cttttacggg  600
caagagactg aagatgccgt tgctttccat aaaagccagg cgctcacagg acggctcaca  660
gatattaaag atattgcacc attggtggag ttcctttgca aggataagtg gattaccgga  720
caagtcatct tctcaaatgg aggttacacg actcgctga                        759
```

```
SEQ ID NO: 14          moltype = AA  length = 252
FEATURE                Location/Qualifiers
source                 1..252
                       mol_type = protein
                       organism = Cryptococcus neoformans
SEQUENCE: 14
MSSTDLGGQA AVITGGGKNL GALIAKTLAK QGVNVAIHYN SASSKSETEA TLKTLGSYGV  60
KAAAFQANLT TEASVEKLFS DAAAALGVSK FDIAINTVGK VLKKPIVETT EQGFDDMFLV  120
NSKCAFFFIK HAAKNLNEGG TIISLVTSLL GAFAPGYSTY QGSKAPVEWF TKSAAKELQP  180
KNIRVNCVAP GPMDTPFFYG QETEDAVAFH KSQALTGRLT DIKDIAPLVE FLCKDKWITG  240
QVIFSNGGYT TR                                                     252
```

```
SEQ ID NO: 15          moltype = DNA  length = 2199
FEATURE                Location/Qualifiers
source                 1..2199
                       mol_type = genomic DNA
                       organism = Cryptococcus neoformans
CDS                    1..2199
SEQUENCE: 15
atgcagcacc accccgcggt agcagcacag ccgggccgca ctattgcccc tatcccgcac  60
caccgcccac agcaaccccg gatcactcct tacacaccaa acgtacgcga cctcaaccca  120
ggacctaaga acagactcat cctcgccctc cgctccaaca tccccctttga agtcgactgg  180
gcgctaccgc agcttgttgt cgcaagtttc gaccagtcgg acgggttcaa gctcgaggca  240
```

-continued

```
tggccagaca gcatttgcgc gttgaaggaa tggccggcca agtggcttga aggactagaa  300
agggaagctg cagtgtttga gatgaaagct gggcgattgg attttgaggg ggacgagaat  360
gatgaagagg ggaggatggc aaagcgcaga aaaagggatc tggcgctggg ggcggtggta  420
gagtgggaga acgatctcaa ggtggaacaa cgggcgacca actctttgct cgtcctcaga  480
aacgcatcct tcaacgcacc caacgcaaag atcctctcaa gctcaagctt cctcgctttt  540
ctagccgatt tcttctcttt gcctctaccg tttctccagc atctttgcct gagaacccca  600
gagcctatac atcatatcct catcattgtc cagtccatct tcccccattt gcgcgtggac  660
atgccaggta tcgaccgcat caagcacatc tttggcgtcg tcttccctca gctttttgtt  720
gatacccgcg atatcgcaat gatgaacaac cttatccctc tcatgatgat gggccagaca  780
atccccaata accaccctcc tccgcctgaa ctcatccctc atcttctcca gcttctcgtt  840
ctccgtccag caggcccact tctcgatttg actcttgaca tcctcatctc cctctccaca  900
aatcccatcc actcccgtgc catactttct catacttctt tcccgcatca tctcaaatcc  960
atcacagcct tactcgaaca tcaagctcgt ccggtggtga atgcccttga cccaccgcct  1020
tctacgagag ggaaaatggt gcgtaaccca gcgggaccga gttgcagagc agaggaactt  1080
aatcaaaggc ggacgaagga acgagaggcc gcattgggac atatggatcc catggctgga  1140
ggtagaccgg tgtacaatga ggtaggggat aagccaccga catttagtcc ggcgacgaag  1200
aagaggcttt tcaggatgaa agaacccgaa aggtctatcg agtggatgca ccaggcattc  1260
gtctactcat cgacagccca agtccttcaa gtgacattct ggcacgccta ccgagatttc  1320
ttcaccaacc cagcttgcgt agaaccaatg ttgagtgcat ctgatgtgat caagaatgtc  1380
actgcagctt tccctggagc gagcgcaaaa gtttggaccg atgcgagtgg tgcgcaaaag  1440
tttgtgattg ctggtgtcgg gttcaggaag cgatcagatg acgatgaaag gtttacatgt  1500
tactggcatg catgcaccca acggtactca gctaccaacc ccgtccaact gctcgaacac  1560
attagcaact accatctcca aacccttttct gcaccccaat gccaatgggg ctcatgcgat  1620
cacaacctct gcacgtactc tcatctcctc acccatatcc ccctcggcca gcctccatcc  1680
tccatctccg tccctgacgc catctcttgc catatcgcag accatagtag ctccgtcttg  1740
cagcgcaaga tcaccaatcg taccgtccct cctttatcca gcgttcgtct agccgttcag  1800
ggggcattta cccctgtcga cgctcgtcga caacctactg gcgccgccct tctcgcggcg  1860
ttacttatcc gtaacctcgc ccgtaccctc cgtgccgaga tctcgctcgc cgtgcccgaa  1920
ttgtctcatg ctcaaacgca agaaacggca gatgaagctc aagcgagaaa aaaacacctt  1980
ctcgaagaga ggtatggatt gccaatcccg gattcggtgt tgaaagaaga agaagaggag  2040
caggcgaatg tgcagcaagg ccaagattta gatatgagtg aggaagagag ggagagggcg  2100
aaaaaggcgt ttgagaatgt ggaggagagg attatgaagg tcatgttgga gaatgttagt  2160
gggataacgc agtatcttgg tgatgcgctt gggctgtag                        2199

SEQ ID NO: 16          moltype = AA  length = 732
FEATURE                Location/Qualifiers
source                 1..732
                       mol_type = protein
                       organism = Cryptococcus neoformans
SEQUENCE: 16
MQHHPAVAAQ PGRTIAPIPH HRPQQPRITP YTPNVRDLNP GPKNRLILAL RSNIPFEVDW  60
ALPQLVVASF DQSDGFKLEA WPDSICALKE WPAKWLEGLE REAAVFEMKA GRLDFEGDEN  120
DEEGRMAKRR KRDLALGAVV EWENDLKVEQ RATNSLLVLR NASFNAPNAK ILSSSSFLAF  180
LADFFSLPLP FLQHLCLRTP EPIHHILIIV QSIFPHLRVD MPGIDRIKHI FGVVFPQLFV  240
DTRDIAMMNN LIPLMMMGQT IPNNHPPPPE LIPHLLQLLV LRPAGPLLDL TLDILISLST  300
NPIHSRAILS HTSFPHHLKS ITALLEHQAR PVVNALDPPP STRGKMVRNP AGPSCRAEEL  360
NQRRTKEREA ALGHMDPMAG GRPVYNEVGD KPPTFSPATK KRLFRMKEPE RSIEWMHQAF  420
VYSSTAQVLQ VTFWHAYRDF FTNPACVEPM LSASDVIKNV TAAFPGASAK VWTDASGAQK  480
FVIAGVGFRK RSDDDERFTC YWHACTQRYS ATNPVQLLEH ISNYHLQTFS APQCQWGSCD  540
HNLCTYSHLL THIPLGQPPS SISVPDAISC HIADHSSSVL QRKITNRTVP PLSSVRLAVQ  600
GAFTPVDARR QPTGAALLAA LLIRNLARTL RAEISLAVPE LSHAQTQETA DEAQARKKHL  660
LEERYGLPIP DSVLKEEEEE QANVQQGQDL DMSEEERERA KKAFENVEER IMKVMLENVS  720
GITQYLGDAL GL                                                      732

SEQ ID NO: 17          moltype = DNA  length = 1305
FEATURE                Location/Qualifiers
source                 1..1305
                       mol_type = genomic DNA
                       organism = Cryptococcus neoformans
CDS                    1..1305
SEQUENCE: 17
atgagactca cgattattgc cccagactcg gttcatgagc acgaagtgtc cccttccttg  60
ctcatccaag acatcatcaa catcgttgag gcaactgccg accttccccc ggctgttatt  120
gttctcacaa gtgacgccgg tacaccactc acggacccca caagaactct cgaaagctat  180
gggttaaatg gagagaccgc caccatcttc cttacaccta caggaccacc cgtcgcttct  240
tcgtcttcca ttccattccc tgatgcagat gccgacattg aaaggatgcg tttacaagcg  300
ctcggaaatc cttctttgat gaatgatttg cgtgagcgtg atccggaaac ctttgccgct  360
attcaagggg gtactcaaag cttcaaaaaa gccctccaac tggcgcaatc aagacaaaga  420
gatgccgaat tcgaaaagca acgccagatt gaagcactca atgccgaccc ttatgacatt  480
gaagctcaga aaaagattga ggaagcaatt cggatggagg ccgttttgga gaatatgcag  540
cacgctatgg aatattcccc tgagtcgttt ggaaacgtga ccatgctgta tatcaatgtg  600
gaagtaaatg gtcatcctgt taaggcattc gttgattctg gtgcacaaac aacgatcatt  660
tcccctgaat gtgccgagca atgtggaatc atgcgcctgc ttgatactcg tttcgcgggt  720
atggccgaag gagtaggaac agctcgtatc ctcggtcgta tccactctgc ccaaattaag  780
ctcggctcac tctacctccc ttgtgcattc tccgtcctcg aaggccgttc tgtcgacctc  840
ttatttggtc ttgacatgct taaacgccat caatgctgta tcgacctctc cacgaacacg  900
ctccggataa ataacactga agtacccttt ttgtcggagc acgagctgcc tgacaaggcg  960
agaagacgtg gggaggcgca agtggccggg gaaatgggtg atgcggcagg gcaaggcgtg  1020
aaagcgggtg tggcgagtcc gaagattggg aagaagacgt ttccgggaga ggggcatgcg  1080
```

-continued

```
cttggtgcgg gcagctcgac tggaccaggg acggctacgg ggagtgcaag tgcgacaggt  1140
gcaaggactg gggggactgc aagtgtcccc tcgccttcaa ataggtggaa agaggacgat  1200
attcaaacgc ttgtgaacct gggtgcccct cgagcgcaag ctatacagct acttgaagcg  1260
tcaggtggaa acgtggatgt tgctgcttct atgctctttg gttag                  1305

SEQ ID NO: 18           moltype = AA  length = 434
FEATURE                 Location/Qualifiers
source                  1..434
                        mol_type = protein
                        organism = Cryptococcus neoformans
SEQUENCE: 18
MRLTIIAPDS VHEHEVSPSL LIQDIINIVE ATADLPPAVI VLTSDAGTPL TDPTRTLESY  60
GLNGETATIF LTPTGPPVAS SSSIPFPDAD ADIERMRLQA LGNPSLMNDL RERDPETFAA  120
IQGGTQSFKK ALQLAQSRQR DAEFEKQRQI EALNADPYDI EAQKKIEEAI RMEAVLENMQ  180
HAMEYSPESF GNVTMLYINV EVNGHPVKAF VDSGAQTTII SPECAEQCGI MRLLDTRFAG  240
MAEGVGTARI LGRIHSAQIK LGSLYLPCAF SVLEGRSVDL LFGLDMLKRH QCCIDLSTNT  300
LRINNTEVPF LSEHELPDKA RRRGEAQVAG EMGDAAGQGV KAGVASPKIG KKTFPGEGHA  360
LGAGSSTGPG TATGSASATG ARTGGTASVP SPSNRWKEDD IQTLVNLGAP RAQAIQLLEA  420
SGGNVDVAAS MLFG                                                    434

SEQ ID NO: 19           moltype = DNA  length = 3555
FEATURE                 Location/Qualifiers
source                  1..3555
                        mol_type = genomic DNA
                        organism = Cryptococcus neoformans
CDS                     1..3555
SEQUENCE: 19
atgtcttcgc cagaaccaga ggagcctcgc agaggtgcaa gggtcaggaa gcaggttaat  60
aagtttgatg ctagccagca gaacgggagg ggcaagagaa agcacattga agacagggag  120
gacgacgacc aggagggttt gataccagac ccggaagacg agtctgatca cgaaccaact  180
cccaagaaga agaagccggc ggcaccacga aaatctcgag cttctgcggg tactaccaag  240
aaggacggac caaagacaaa aacaaagcct gcagctgaag gcgtgagcga aatcgtagaa  300
aagactgatt cgcctttatt taatgctctc cagcaacccg atatcgccct tcaacctctg  360
attgatgagt ggatcgagac ctaccaacaa gccgctggtg atgaaatatc agagcagaaa  420
tccattcacg aactggttgt cttcttcatt cgatgttgcg gtatgactac cgagatcgag  480
caagctgaag caacggatga cgatggtatc cccgatgtca tcgagcgagt gcaggatgaa  540
agcgttcgcg tagcgttggc gacttatccc ttaatttcca aagcaaagaa ttttaagccc  600
ttcaagtcca atttgaacga gttcatttca cactttattt catcgctcgc tctcacacct  660
atcctctttc acactgccga caatactcct cactcatctc tgctcatccc acttctcctc  720
aactggctga tgtgtatgtc atcatcaact cttcgaccca tccgtcatac ctcaacatac  780
gtgacgctca ggatgaactc ggctttgtgt gacgttgctg cggatgtgag caaagacctg  840
agcgttaagc aaaggcagcg agatgcagaa gtcagaaaag ctggagctac aaatgcagcg  900
cagaagagag tgaaggctgc cgaggacagg gtcaaggaag tgcaagaaag aaagcaaact  960
ttagaagagt tgatgcagga gatctttgat gtgatgttcg tccaccgagt tcgcgatgcc  1020
gatcccaaca ttcgaaccga ttgtctgcgt gaattaggtc tgtgggccaa aaaacaccca  1080
gagtactacg tttcgacttc ttatctctcc tacttcaccc gtggctgtaa cgatacccac  1140
gctcatgccc gacttgagac tgtcaaggct cttgccaacc tctacatccg agaaaccttt  1200
atcagtaacg ctcgaacctt gacgatgcgt ttagcgccta gggtgattga gatggccacc  1260
agggatgtgg atttgaatgt gagggtagtg gctttgcagg tgattacact tatagacaag  1320
acgggtattc tgcaagacga ggaggacgag gaaagagata aggtggcgaa gcttgttttc  1380
gaccaggagc ctcgaattcg aaaagctgca ggggcgttca tccttggttt gtgggaagag  1440
aggaaagaag gcctcaaagc agtctggtcg ggtctgagag cgaacaaaaa gaagcgtgca  1500
gcaaacatca ccgaagacga aatgtccaac tacctcaact ggaaatccct cgctgcagtt  1560
ctcctctaca cctctaaatc cctggacgac gacccttctg gacaaccctc tgccctcaaa  1620
ccaagcctac tcattccgtc tttacccaat acacagatga caagggcgac tgctgccgtc  1680
gagtctatcg gtgctgagca tgagctgtgg aaagactggg agagcttggt ggactatctt  1740
ttggtggatc actcgactaa cgaagaagat atgtggctgc tccgtgaaga tgaggaaact  1800
ttcatgttgc aggtgctttt ggcttgtatt aagcgggaag aaaatgaaga ggatgagccg  1860
gataggacca aaacgttgat aaaggttttg cctcggttat ttgccaagca tcaggctgat  1920
gttggtcgaa tgactgggat tttatctgtt cccggacaca tgaagctcag tctctatctc  1980
gacatgcgca tgtcctctgc ctacgagtcc ctctgggatg acatcagcaa acagttccta  2040
aaatacactt cccctaccat cctcacagca tccatttctg cgatcagcca tctcgtcggc  2100
aactcgtccc tttcatccat caatgaaacc aagctttctg agctgcacga gtctctcttc  2160
gcttctctaa gagatgcgat tggctctgaa gatgttgcgc ttgtcacttt ggaggacgag  2220
cagatcagcc agctggaagc aatcatgctg aggataacgt tactgcagag aagtatggat  2280
ttggtagatg tcatggagga tgaggaaggg cagcagagta gcggctggga cattatctgt  2340
gcgtttgctg ataggggcaa attggggtac aaggaggaag ctactatggt agactatgct  2400
gttcaaatca tcttcctcca catcacttgg ctcttcaagc ggttcaccaa ggaagatgcg  2460
caagatgcca ccaagattga tctcctttcc acccgacgcg ataccgccct tcagacattt  2520
aaccagcttt tcctcggaga aacgaccaat accgccagtg ctgtacgacg tcaagccttc  2580
atctctttca tcaatacgta cgtattgttc gccaaacgtg cagagggtag gggaggagct  2640
ccagcgagcg acgtttgttc tgtgacgatg ccggaagaag tacagcatag actgggaggg  2700
gcgttccaag cggtgattga gaggtatgct tccgtcgtgg agactagatc agcaggacgg  2760
gaagagagtc agcagccccc cgaactcact cctgatgaga tgcacgagga tttccagttt  2820
ttccaactcg tttccgtttt tgtcggtgcc atccgatgtg gtgtcctcga ggttgaacat  2880
gccaaggaac ctcttgccca ttacagtcgt tttggtccaa cgtacgatgc gatcgtcaag  2940
aagctcgttg atgtacttcg agatgagggt atctacaata gggaggcaga tgcggtgcag  3000
catgttgcgg gaagcgcctt gcagcaatcg ttcaacatct tcctcgactc tgaggaagac  3060
gaaccaactg ctcctctggc ccttgcccgt gttattgcaa ctgcgttcgt catccatggt  3120
```

-continued

```
tcccaattcg ctatcctaag acaattgcat ccatctgatg tttgcgattt ccacctcgaa  3180
gcgcttgact ttgtttctct caaagtctca acgattgtca aacaagaagg aaatgcaagg  3240
aacaaggagc aaaaatccag actaacaagg aaaaagtggg cagtgctcac attcttcaag  3300
gtgctcgtcc ctcttctcgc gcctgtcaca ggtagagatg ctctcaagat caaggctcat  3360
ctcgaagatg taatcgactc ttctggggtg caactgacaa ccaacaaggg ttgggatggc  3420
taccgagcgt acgaaaagag attagtaggg atcgcaagca aggacccgaa tgtgaaaatg  3480
atggctagca agaaggttgt agaaagggag gatactgaac agggtgatga agacaatgtc  3540
tttgcaaggc aatga                                                   3555

SEQ ID NO: 20          moltype = AA  length = 1184
FEATURE                Location/Qualifiers
source                 1..1184
                       mol_type = protein
                       organism = Cryptococcus neoformans
SEQUENCE: 20
MSSPEPEEPR RGARVRKQVN KFDASQQNGR GKRKHIEDRE DDDQEGLIPD PEDESDHEPT  60
PKKKKPAAPR KSRASAGTTK KDGPKTKTKP AAEGVSEIVE KTDSPLFNAL QQPDIALQPL  120
IDEWIETYQQ AAGDEISEQK SIHELVVFFI RCCGMTTEIE QAEATDDDGI PDVIERVQDE  180
SVRVALATYP LISKAKNFKP FKSNLNEFIS HFISSLALTP ILFHTADNTP HSSLLIPLLL  240
NWLMCMSSST LRPIRHTSTY VTLRMNSALC DVAADVSKDL SVKQRQRDAE VRKAGATNAA  300
QKRVKAAEDR VKEVQERKQT LEELMQEIFD VMFVHRVRDA DPNIRTDCLR ELGLWAKKHP  360
EYYVSTSYLS YFTRGCNDTH AHARLETVKA LANLYIRETF ISNARTLTMR LAPRVIEMAT  420
RDVDLNVRVV ALQVITLIDK TGILQDEEDE ERDKVAKLVF DQEPRIRKAA GAFILGLWEE  480
RKEGLKAVWS GLRANKKKRA ANITEDEMSN YLNWKSLAAV LLYTSKSLDD DPSGQPSALK  540
PSLLIPSLPN TQMTRATAAV ESIGAEHELW KDWESLVDYL LVDHSTNEED MWLLREDEET  600
FMLQVLLACI KREENEEDEP DRTKTLIKVL PRLFAKHQAD VGRMTGILSV PGHMKLSLYL  660
DMRMSSAYES LWDDISKQFL KYTSPTILTA SISAISHLVG NSSLSSINET KLSELHESLF  720
ASLRDAIGSE DVALVTLEDE QISQLEAIML RITLLQRSMD LVDVMEDEEG QQSSGWDIIC  780
AFADRGKLGY KEEATMVDYA VQIIFLHITW LFKRFTKEDA QDATKIDLLS TRRDTALQTF  840
NQLFLGETTN TASAVRRQAF ISFINTYVLF AKRAEGRGGA PASDVCSVTM PEEVQHRLGG  900
AFQAVIERYA SVVETRSAGR EESQQPPELT PDEMHEDFQF FQLVSVFVGA IRCGVLEVEH  960
AKEPLAHYSR FGPTYDAIVK KLVDVLRDEG IYNREADAVQ HVAGSALQQS FNIFLDSEED  1020
EPTAPLALAR VIATAFVIHG SQFAILRQLH PSDVCDFHLE ALDFVSLKVS TIVKQEGNAR  1080
NKEQKSRLTR KKWAVLTFFK VLVPLLAPVT GRDALKIKAH LEDVIDSSGV QLTTNKGWDG  1140
YRAYEKRLVG IASKDPNVKM MASKKVVERE DTEQGDEDNV FARQ                    1184

SEQ ID NO: 21          moltype = DNA  length = 897
FEATURE                Location/Qualifiers
source                 1..897
                       mol_type = genomic DNA
                       organism = Cryptococcus neoformans
CDS                    1..897
SEQUENCE: 21
atgaagtact ctgctaccgc agtcgccgtt atgggtgccc tcgccattca agccacccca  60
atcaagagag atgcttacac cccaaccgac attgatatcc tacagtatgc gttgactctc  120
gagcacctgg agaacaactt ctactcctgc gccctcaaca acatggacgc tcaagcgttc  180
gccgatgccg gattcccagc ctgggtacgg aacaggtttg agcagattgc cgctcacgag  240
gcctcccacg tcgccgttct ctccgatgcc ctcggcgctg acgccaccaa gccatgcgag  300
tactccttcc catacaccga cgccaaatcg ttcaccgctc tcgctcaggt cattgagaat  360
gttggtgttt ctgcttacct cggtgccgcc ggtttcatca tggacaagac ctacttgacc  420
gttgctggtt ccattctcac caccgaggcc cgccaccagg cctggatcgc ttccgccgtt  480
aacaagcaga acccatggtc cggcccatac gacactcctc tcggtctctc cgatgtctac  540
tccattgccg ctgccttcat caccagctgt ccatcctcca acccaactct cccagtcaag  600
gcattcccag ctctcactct ctcttgcgac tccgccggtt cgactgccac cctcaactat  660
accggcgctg attcatccga cacccttatt ctctactctg gcctcacgac cctcgctctc  720
cccatcaccg acatgatggt caccatccca tcctctcttc agggcattgc ttacgcagtc  780
gtgtcttcaa cgtctaacac caccatggtt gacgactcta acaccattgc cggcccagcc  840
atcattgacc ttcctttcgc ttcttccgcc agcaacccca acttcactgg tatgtaa     897

SEQ ID NO: 22          moltype = AA  length = 298
FEATURE                Location/Qualifiers
source                 1..298
                       mol_type = protein
                       organism = Cryptococcus neoformans
SEQUENCE: 22
MKYSATAVAV MGALAIQATP IKRDAYTPTD IDILQYALTL EHLENNFYSC ALNNMDAQAF  60
ADAGFPAWVR NRFEQIAAHE ASHVAVLSDA LGADATKPCE YSFPYTDAKS FTALAQVIEN  120
VGVSAYLGAA GFIMDKTYLT VAGSILTTEA RHQAWIASAV NKQNPWSGPY DTPLGLSDVY  180
SIAAAFITSC PSSNPTLPVK AFPALTLSCD SAGSTATLNY TGADSSDTLI LYSGLTTLAL  240
PITDMMVTIP SSLQGIAYAV VSSTSNTTMV DDSNTIAGPA IIDLPFASSA SNPNFTGM    298

SEQ ID NO: 23          moltype = DNA  length = 534
FEATURE                Location/Qualifiers
source                 1..534
                       mol_type = genomic DNA
                       organism = Cryptococcus neoformans
CDS                    1..534
SEQUENCE: 23
atgtctctaa ctagtgtcac tcgcgtcgta tccaaatcca tcctcggcgc ttcctttact  60
```

-continued

```
agcacaactc gcaggcttac cactaccgtt cccagatttg gtagaatgcc tcctcctgct  120
cacaagatgg cccacttccc gaggatcaca tcctctcttc cctcagaaca ctctgagttt  180
agaacagtga tgtggacggg cgagagcagt caacttgtcc tcatgactat ccctgtcgga  240
ggagaaatag gggaagaaat tcaccatgtt gaccaacact tggttttcac ctctggtact  300
gccaaggcca ttgttggagg agaagaaaaa gagatcaagg ctggagatct tgtcatcgtt  360
cctcagggta ccaagcataa cttcgtcaat acgggcccta cccctctttg cctttttact  420
gtatatgctc cggccgagca tgccgagaca acagtcaaca aaacgaagga ggaaggggat  480
aaattggaag acgagggcaa ggatgagcct ccaaagtggg cagttaggaa gtag        534

SEQ ID NO: 24          moltype = AA  length = 177
FEATURE                Location/Qualifiers
source                 1..177
                       mol_type = protein
                       organism = Cryptococcus neoformans
SEQUENCE: 24
MSLTSVTRVV SKSILGASFT STTRRLTTTV PRFGRMPPPA HKMAHFPRIT SSLPSEHSEF  60
RTVMWTGESS QLVLMTIPVG GEIGEEIHHV DQHLVFTSGT AKAIVGGEEK EIKAGDLVIV  120
PQGTKHNFVN TGPTPLCLFT VYAPAEHAET TVNKTKEEGD KLEDEGKDEP PKWAVRK     177

SEQ ID NO: 25          moltype = DNA  length = 1074
FEATURE                Location/Qualifiers
source                 1..1074
                       mol_type = genomic DNA
                       organism = Cryptococcus neoformans
CDS                    1..1074
SEQUENCE: 25
atgccaactg tactcctcac aggtatcacg ggatttctgt ctgcgcacgt cgcccatacc  60
ttcctgaagc atgactggat agtgcacggc acacttcggt ccagctcgaa ggtagcgtta  120
atcgaagtta ttcctgaata ctctccttat atttcgtcag gcaaactaaa actcttcgtt  180
gtcggacctc ttgagaatgc cgattacact gaagccatga aaggcgttga tgctgtggtc  240
cacactgcgt ctccggtaga gtttggtgga gacaatttta gagagagcca tttgaaacct  300
gctttggaag gaacaagggg tgtcctcaga gctgtagcca aagagaagaa tgtaaagtcc  360
gtcgtctaca ctagtacttt tggagccgtt ggtgatcata ggtatcatcc cactgagatc  420
aaaggcaaag ttatcactga ggataactgg aacccgtata ccttggaaga gctggataag  480
atggtggaat ctggagagtc aggcaacccc acatttcctc caggatatct gttctataaa  540
ggagccaaga agtacgcgga actcgctgct tgggaatgcc agaaagaagc gagagaacag  600
ggtgctgaat ggtctttggc cacgatgaac tgtgtgatga tctgggggcc tccaattcaa  660
cctctcacat cactcagtca tgggggcatg tcgaccgagt tcctttggat gcttgcagga  720
gggaaagatg cccatatcat ggacagtctc tatccctatt acgtcgatgt tcgggatgct  780
gctgaagcac actatcaagc caccgtccgt agagcgcaag gaaggtttat catctctgcc  840
ggcccttatg atttccaaga gttcgcagac atgcttaggg agctttatcc tgagcaaaaa  900
gaacgattcg cccttggtgc tcccggcaaa tatatgtaca gagatccagg agtgtacgtg  960
ctcacaaatg aaaagagtca aagggaactt ggtattactt accgtccaaa acaagagact  1020
ctcaaagatg catttgacag gtttttcgct ttggagaaac aaggattgaa gtaa        1074

SEQ ID NO: 26          moltype = AA  length = 357
FEATURE                Location/Qualifiers
source                 1..357
                       mol_type = protein
                       organism = Cryptococcus neoformans
SEQUENCE: 26
MPTVLLTGIT GFLSAHVAHT FLKHDWIVHG TLRSSSKVAL IEVIPEYSPY ISSGKLKLFV  60
VGPLENADYT EAMKGVDAVV HTASPVEFGG DNFRESHLKP ALEGTRGVLR AVAKEKNVKS  120
VVYTSTFGAV GDHRYHPTEI KGKVITEDNW NPYTLEELDK MVESGESGNP TFPPGYLFYK  180
GAKKYAELAA WECQKEAREQ GAEWSLATMN CVMIWGPPIQ PLTSLSHGGM STEFLWMLAG  240
GKDAHIMDSL YPYYVDVRDA AEAHYQATVR RAQGRFIISA GPYDFQEFAD MLRELYPEQK  300
ERFALGAPGK YMYRDPGVYV LTNEKSQREL GITYRPKQET LKDAFDRFFA LEKQGLK     357

SEQ ID NO: 27          moltype = DNA  length = 2781
FEATURE                Location/Qualifiers
source                 1..2781
                       mol_type = genomic DNA
                       organism = Cryptococcus neoformans
CDS                    1..2781
SEQUENCE: 27
atgtttagga agagaattct ttatctttct tctttttcaa tccctttgta cacagtccca  60
gcccacagtt attcctgtac ttttcagacc aaccagcgcc cttctactct cctcaaacgc  120
gtacattcgc tcgctatgtc cttcccgcca gtgcagcccg ccgacaatgg catggcggtc  180
gttgctccca atctcgagtc taaccctacc actgttgcgt cccacgcccc acaaattgcc  240
gtcaaggatg aaaatgatag tatgagcgag gatgagcagc ctttggcgaa aagcaaagcg  300
aatggagcga ggaagagagt cgaaaacagc agtgacgagg aagagaaacc tctcagcaaa  360
aagcccagag ccaatggtgt caacaagaaa agggtcgtcg ccagcagtga tgaagaaagc  420
gatgtttcac ctcctgctaa gaggcctgtt tccaagcaat ccaaacctgc cacccccgat  480
tctgaatctg atgacgatca acctctcgcc aagaaggcta acggactggc cgcatccaaa  540
cgtcaggcta aaaaagcgga ggaattatca gaagaaagct cggaggaaga aaagcctctt  600
gcgaaggttg ccaagagggt atcagcaaag aagatgaaga gcgagactga ggactctgag  660
gaagaccggc ctcttgcaaa gaagaaggct cctgttaagc gtgctccagc aaagaaatcg  720
gcgaagaagg aacctagtga gagtgaagag gatgagaagc ctttagcgaa gaacgctaga  780
gggaaggcca aggcggcgac ggtgaaggaa gagaaaggta agaagacaaa gaaggagaaa  840
```

-continued

```
gaagaggaag aagaggagga aaggtacaag tggtgggaac aggatgcttt gggtgatggg  900
tcatccaagt ggacggtcct tgagcacaac gctgttctct tccctcctcc ttatgttcct  960
ttacccaaga acgtgaaaat gaagtacgat ggcgtctcac ttaccctccc tcccgagtct  1020
gaagaagtcg ccggtttctt cggtgccctc cttgaaaccg actatgctca agatgccaaa  1080
ttccgtgaaa actttttccg agactttaag gctatcgtcg aaaaatatcc acccaaggag  1140
gacgtcaagg ttaagaagtt ggaaaagtgc gattttagac cgatgtttga gtactttgaa  1200
aaggagaagg agaagaagaa ggcgttgact aaggaagaga aaaaggcgat taaagcggag  1260
aaggacaagc ttgaagcacc gtatctctat gcgaatgttg atggaaggaa ggaaaaggtc  1320
ggcaacttcc gtgcagaacc tcctggattg ttcaagggtc gtggtgaaca tcccaagaag  1380
ggtactgtca agaaccgtct ccgacctgaa gatatcatta tcaacattgg caaagaagct  1440
cctatccctg tgcccaacat tcccggtcag tggaagggta tccagcatga taacacagtg  1500
acttggctcg ctcattggaa ggagaatgtc aacggtaacg ccaaatacgt cttcttgagc  1560
gctggtagtg cgtggaaagg tcaaagtgat cgtgccaagt ttgaaaaggc ccgtgagctt  1620
atcaaacatg tcgacaaaat tcgaaaagac tacactgccg acctcaaatc caaagtcatg  1680
gctgaccgac aacgtgccac cgccctgtac tttatcgatc gtctggctct gcgagcgggt  1740
aatgaaaagg gtgaagatga agcggatact gtcggctgtt gttctctgcg atacgaacac  1800
gtgacgctct ctccaccgaa tactatcatc tttgatttcc tcggtaagga ctcgatgagg  1860
ttccatcagg aagtcgaggt cgatccgcaa gtgttcaaga acataaaact gtttaaggct  1920
gatccgaaga agaagggtga cgatatcttt gaccgactga ccaccactct tcttaacaag  1980
cacctcaaca gcatgatgcc tggtcttacc gccaaggttt tccgtaccta caacgcctca  2040
tggactttcc aagaacaact caaaaacaca cctaagaacg gaactgtagc cgagaagatt  2100
gcggcgtaca acactgccaa tagggatgtt gccatcttgt gtaatcacca aaagagtgtc  2160
agcaagggtt ttgagggcag ttttgccaaa gccgaggata agattcgtgc cctcaagtat  2220
cagcgtctca agcttcgtct ccaacttttt tctcttaacc ccaagattaa gaagaagcat  2280
cccgagcttg cggaggatga gtctgatgtg gatgacgaat ttatggagcg ccacgaagcc  2340
gaattactcg aaaaagcttt ggagaacgca aagaagaaat gggatacgga taatgtcaag  2400
cttgaagggg atgggaagaa aaagaagacg aagggagagt tggatgagag gttgagtgag  2460
atcaaggcag agtttaagga gttgaagaag gagaggaagg ctaaaaagat tgatgccaag  2520
agaggagcca cggaggagaa acttcttgct caggtcgcca ggatcgacga acgtatcgct  2580
accgccaaag tccagcttca agatcgagac aagctcaagg atgttgcttt gggcacatcc  2640
aagattaact atatcgatcc aagactaact gtcgcgtggg cgaagaagtt tgatgttcct  2700
ctcgaaaaac tgttctccaa aaccctgcga gaaaagttcc cttgggctga ggcggaggct  2760
ggaccggact gggttttcta g                                           2781

SEQ ID NO: 28          moltype = AA  length = 926
FEATURE                Location/Qualifiers
source                 1..926
                       mol_type = protein
                       organism = Cryptococcus neoformans
SEQUENCE: 28
MFRKRILYLS SFSIPLYTVP AHSYSCTFQT NQRPSTLLKR VHSLAMSFPP VQPADNGMAV  60
VAPNLESNPT TVASHAPQIA VKDENDSMSE DEQPLAKSKA NGARKRVENS SDEEEKPLSK  120
KPRANGVNKK RVVASSDEES DVSPPAKRPV SKQSKPATPD SESDDDQPLA KKANGLAASK  180
RQAKKAEELS EESSEEEKPL AKVAKRVSAK KMKSETEDSE EDRPLAKKKA PVKRAPAKKS  240
AKKEPSESEE DEKPLAKNAR GKAKAATVKE EKGKKTKKEK EEEEEERYK WWEQDALGDG  300
SSKWTVLEHN AVLFPPPYVP LPKNVKMKYD GVSLTLPPES EEVAGFFGAL LETDYAQDAK  360
FRENFFRDFK AIVEKYPPKE DVKVKKLEKC DFRPMFEYFE KEKEKKKALT KEEKKAIKAE  420
KDKLEAPYLY ANVDGRKEKV GNFRAEPPGL FKGRGEHPKK GTVKNRLRPE DIIINIGKEA  480
PIPVPNIPGQ WKGIQHDNTV TWLAHWKENV NGNAKYVFLS AGSAWKGQSD RAKFEKAREL  540
IKHVDKIRKD YTADLKSKVM ADRQRATALY FIDRLALRAG NEKGEDEADT VGCCSLRYEH  600
VTLSPPNTII FDFLGKDSMR FHQEVEVDPQ VFKNIKLFKA DPKKKGDDIF DRLTTTLLNK  660
HLNSMMPGLT AKVFRTYNAS WTFQEQLKNT PKNGTVAEKI AAYNTANRDV AILCNHQKSV  720
SKGFEGSFAK AEDKIRALKY QRLKLRLQLF SLNPKIKKKH PELAEDESDV DDEFMERHEA  780
ELLEKALENA KKKWDTDNVK LEGDGKKKKT KGELDERLSE IKAEFKELKK ERKAKKIDAK  840
RGATEEKLLA QVARIDERIA TAKVQLQDRD KLKDVALGTS KINYIDPRLT VAWAKKFDVP  900
LEKLFSKTLR EKFPWAEAEA GPDWVF                                      926

SEQ ID NO: 29          moltype = DNA  length = 1125
FEATURE                Location/Qualifiers
source                 1..1125
                       mol_type = genomic DNA
                       organism = Cryptococcus neoformans
CDS                    1..1125
SEQUENCE: 29
atggcccacc accacttcgt aggcataaac ccggcaggcc tctccttctc ccatcccacc  60
ccgccagcag accaccccgc gcccccctcc tcgggcagca tccacacccc agcaaacttc  120
gccagcattc aagaacccat cacagaccca tccgctgtcg ccgcccgccg acgcggtcgt  180
ccttccacaa ggggcgaagc tggcgtcact ccgccccccag agatcggatg gtgggaggac  240
cgtgcgccca gctggcacaa ggatgccatg cagggcggca agtcttctat ggagctcctg  300
atggaatggt cagaggagat gaagaatcaa ggccactact actggatggg cgtcagggat  360
ggcggcaatc tgcatcaagg tgcttcgcgt tttagggact acttatatgc ccagcatggt  420
cctattaggc ggtcaagtaa ggctatcaga aataaagtgg agaatattaa gcaaaagttc  480
tttgaagccc aggaatggct caaggatccc aatggggacc ataccaccat gaccattccg  540
gacgtcgaaa aaaaactcaa caagatctgt cgcaactacc gcttctggga aaccatcttc  600
gtagagcttc ctccagttga ccacgaagct ggccagaatg ccgaagggtc ttcatccaac  660
cagactcttc agtctgcttc tcaaactgcc gttcgacagg gtaatgggcc cctcatccgc  720
ggtattcctg ttccggaaat gggacaggca gcggccgatg atgcgcagcg aaatgtccgc  780
cgacgcctta atgatggcag ctctgccact attccttccg actcatcttt ggttggtcgc  840
gtgctccctg ctagctacct cgaacgcacc cgtgaagaac gcgatcgcga aaagcatgaa  900
```

-continued

```
ttagcgaaaa agcagcaagc cctcaacagg gaacaatatg aactcgagca gaagaaagat  960
gagagagatc agaagagatt tgagtgggag cagactaagc atctggtgga gacggcttta  1020
aaaatccgag aattggatat cattccgttg gaagcggcga tgatcaaagc tagagctctt  1080
tatggccagg cgcgagagga agatcaagct gaagctactc tttaa                 1125

SEQ ID NO: 30          moltype = AA  length = 374
FEATURE                Location/Qualifiers
source                 1..374
                       mol_type = protein
                       organism = Cryptococcus neoformans
SEQUENCE: 30
MAHHHFVGIN PAGLSFSHPT PPADHPAPPS SGSIHTPANF ASIQEPITDP SAVAARRRGR  60
PSTRGEAGVT PPPEIGWWED RAPSWHKDAM QGGKSSMELL MEWSEEMKNQ GHYYWMGVRD  120
GGNLHQGASR FRDYLYAQHG PIRRSSKAIR NKVENIKQKF FEAQEWLKDP NGDHTTMTIP  180
DVEKKLNKIC RNYRFWETIF VELPPVDHEA GQNAEGSSSN QTLQSASQTA VRQGNGPLIR  240
GIPVPEMGQA AADDAQRNVR RRLNDGSSAT IPSDSSLVGR VLPASYLERT REERDREKHE  300
LAKKQQALNR EQYELEQKKD ERDQKRFEWE QTKHLVETAL KIRELDIIPL EAAMIKARAL  360
YGQAREEDQA EATL                                                   374

SEQ ID NO: 31          moltype = DNA  length = 1251
FEATURE                Location/Qualifiers
source                 1..1251
                       mol_type = genomic DNA
                       organism = Cryptococcus neoformans
CDS                    1..1251
SEQUENCE: 31
atggacgcca ccactcttac agggcacgtc aaggagctca atgctgcaaa ccaagcggga  60
aaatcagatg aagttatctc tctgctcaag aaacttcagg ctgaggttgt tcctacagaa  120
gatctccttc gatcatcgaa agctggtgtc gcagtcggca agcttcgtac ccacgccaca  180
ccatcagtct caagtcttgc caaggagata gttaagaagt ggagagatgc ggtcgaggag  240
acaaagaaga agagaaaaag agcagaaggt gatgaaggaa aagatgtaaa gaaggagaag  300
gaggaaggga acgggaaacg agtcaaggcg gaaacggggt cattagcggc gacaccatca  360
gctagcacac ccgcctcggc ctctacaccc gatgtcaaag cgacctcccc tcctgtccgt  420
caacctcttt caaccattga ctcatcacgc actacgcctc gaaccgccaa aagcgatgga  480
gtggccgaca gcctgagagc tgattcgagc gaaggaggca gtgtagatag cgtgagggac  540
aagtgtgtga tcatgattta tgacgcattg gcgttggata gcacggctga aataaagatt  600
ttgaaagagc gcgccattgg aattgagcgc gcagcgaata aagctatgaa cttctcaaca  660
ggaaacgatt atcgcgctaa aatgagatca ctattcctca acttgaaaga caagggtaat  720
cccgctttga gaaacgagat tgtcttgggc tacgtcagca ccgaaaaagt cgctagcatg  780
tccaaagatg aaatggcctc tgaaagcgtt cgaatgctaa aggagaagat tgcgagtgac  840
aacttgttca aggccaaggc tgtcggagtc acccaagctg agacagacgc gttcaagtgc  900
ggacggtgtc accagaggaa atgtacttat taccagatgc agacaagaag cgcggatgaa  960
cctatgacta cttttgttac gtatgtgtct gacctgactc caaaagaatc attgctgact  1020
acgtgtacga cttgctcttt ttattcagat gtactaattg taacaacagg tggaaattca  1080
gctagtttcg gattttgcct ctggggagca ttgtatcttt cgggtttttt gtcacgtcgt  1140
ctatgcagcc agtatattta cgaggcgtat cgttgtgatt tgcgtgtcaa tgtcacaaag  1200
ccattaagtg ccgtaaatat gcctttttgc agtgttctga aattcaaatg a          1251

SEQ ID NO: 32          moltype = AA  length = 416
FEATURE                Location/Qualifiers
source                 1..416
                       mol_type = protein
                       organism = Cryptococcus neoformans
SEQUENCE: 32
MDATTLTGHV KELNAANQAG KSDEVISLLK KLQAEVVPTE DLLRSSKAGV AVGKLRTHAT  60
PSVSSLAKEI VKKWRDAVEE TKKKRKRAEG DEGKDVKKEK EEGNGKRVKA ETGSLAATPS  120
ASTPASASTP DVKATSPPVR QPLSTIDSSR TTPRTAKSDG VADSLRADSS EGGSVDSVRD  180
KCVIMIYDAL ALDSTAEIKI LKERAIGIER AANKAMNFST GNDYRAKMRS LFLNLKDKGN  240
PALRNEIVLG YVSTEKVASM SKDEMASESV RMLKEKIASD NLFKAKAVGV TQAETDAFKC  300
GRCHQRKCTY YQMQTRSADE PMTTFVTYVS DLTPKESLLT TCTTCSFYSD VLIVTTGGNS  360
ASFGFCLWGA LYLSGFLSRR LCSQYIYEAY RCDLRVNVTK PLSAVNMPFC SVLKFK      416

SEQ ID NO: 33          moltype = DNA  length = 657
FEATURE                Location/Qualifiers
source                 1..657
                       mol_type = genomic DNA
                       organism = Cryptococcus neoformans
CDS                    1..657
SEQUENCE: 33
atggattacc aaaatcgagc aggtgcaaac aagggtagtg gtggtgtcgc tggtgcatcc  60
gagacagcag tggacaggag agaacgtctt cgaaaacttg ctttggagac tattgacttg  120
gccaaagatc cctatatcct taggacccat ctcggtacat tagaatgccg tctttgtctc  180
actcttcacg tcaacgaggg ttcttacctt gcccacactc aaggaaagaa acatcaaaca  240
aaccttgcta ggcgtgcagc caaggacaac aaggatcaga cattaatgat ccaagctccc  300
acagccgcgc aacaagtgaa gaagaaagtg tttgttaaga ttggaagacc tggatacaaa  360
atcatcaaaa ttcgagagcc tgtcagtcaa aggatgggtt tattattcac tgtgtcttta  420
cctgagataa aagcgggaga gaggccaaga aggaggttca tgtctgcttt tgaacaacgg  480
cgagagattc ccaataaagc tttccagtac ttagttttgg cagccgagcc atacgagacc  540
atagcatttg ccatcccctc aaaagagatg gttgacgttg atgaagaccc ggagtcgaca  600
```

-continued

```
tgggagcact gggatgccga cgagaaggtt tacagttgtc aattcttgta taaataa     657

SEQ ID NO: 34          moltype = AA  length = 218
FEATURE                Location/Qualifiers
source                 1..218
                       mol_type = protein
                       organism = Cryptococcus neoformans
SEQUENCE: 34
MDYQNRAGAN KGSGGVAGAS ETAVDRRERL RKLALETIDL AKDPYILRTH LGTLECRLCL  60
TLHVNEGSYL AHTQGKKHQT NLARRAAKDN KDQTLMIQAP TAAQQVKKKV FVKIGRPGYK  120
IIKIREPVSQ RMGLLFTVSL PEIKAGERPR RRFMSAFEQR REIPNKAFQY LVLAAEPYET  180
IAFAIPSKEM VDVDEDPEST WEHWDADEKV YSCQFLYK                          218

SEQ ID NO: 35          moltype = DNA  length = 813
FEATURE                Location/Qualifiers
source                 1..813
                       mol_type = genomic DNA
                       organism = Cryptococcus neoformans
CDS                    1..813
SEQUENCE: 35
atgacagtca aggcagagca agatctctat cttgacccct ccattcggga ttgggtcctt  60
atccctatca ccctaatcat gctactcgtc ggtgtgttaa gacactacat cacgcaattc  120
cttaactctg caccaaaaaa acaaacagca gctgccgttc gcgaacaacg cgcacttggt  180
cgctcagctc tgcttcgggc aactgcgact ctgtcccccc ttccgcctgc ctcttacaag  240
gctctctcgg gatcccttgc tgcttcactt tctactggtg agtatatcaa gcccgcccca  300
gagtcaaagg gggatgcttc tcccgccaat cctctcgaag gtgctgggat ggaaaatgcg  360
atggacggta tgaaaaagca ggccgtaatg atggtaccca acatggttat catgcagtat  420
atcaacgtct ttttttccgg atttatcctt atgcgtctgc catttccttt aaccgcaggc  480
tttaagtcgt tgctgtcaag ggatattccc atggctgatc tcgatgtgcg atgggtttcc  540
gctttgtcct ggtattttct caacttgttt ggcttgaacg gtgttttcaa actaattctt  600
ggagctgaga atgctgctgt agacagccgt gacctcacct cgctgtctgc actttctggg  660
gcaggaggcc ctatgcccgg ccccggcggt ccaccagaca tggtcaagct tttcaaggcc  720
gaggttgaga acttggcatt ggcagaaagt tcatacaagt gggtcggcga cggagtagaa  780
gatagagttt tgagagcttg ggcaaagtt taa                                813

SEQ ID NO: 36          moltype = AA  length = 270
FEATURE                Location/Qualifiers
source                 1..270
                       mol_type = protein
                       organism = Cryptococcus neoformans
SEQUENCE: 36
MTVKAEQDLY LDPSIRDWVL IPITLIMLLV GVLRHYITQF LNSAPKKQTA AAVREQRALG  60
RSALLRATAT LSPLPPASYK ALSGSLAASL STGEYIKPAP ESKGDASPAN PLEGAGMENA  120
MDGMKKQAVM MVPNMVIMQY INVFFSGFIL MRLPFPLTAG FKSLLSRDIP MADLDVRWVS  180
ALSWYFLNLF GLNGVFKLIL GAENAAVDSR DLTSLSALSG AGGPMPGPGG PPDMVKLFKA  240
EVENLALAES SYKWVGDGVE DRVLRAWGKV                                   270

SEQ ID NO: 37          moltype = DNA  length = 1365
FEATURE                Location/Qualifiers
source                 1..1365
                       mol_type = genomic DNA
                       organism = Cryptococcus neoformans
CDS                    1..1365
SEQUENCE: 37
atgaccgcgg tgaacagcaa ccagggcacc ggcaaactga gcggccgcgt gggcattgtg  60
ggcaccggcc atcgcgcgcg cctgtatacc accgcggtgg cgagccgcgc gaacaccagc  120
ctggtggcgc tgtgcgatac caacgatgcg cgcatggatt ggcataacaa aatgctgcgc  180
gaagcgggcc gcccggaagc gaaaaaatat gcggcggaag attttcgcaa aatgctggaa  240
caggaaaaac tggatgtgct ggtggtgacc accattgatt atacccatga tatgtatatt  300
attccggcgc tgaaagcggg cattaaagtg ctgagcgaaa aaccgatgac caccaacgtg  360
gataaatgca aagcgattct gaacgcggtg aacgaaagca aaggcagcct gaccgtgctg  420
tttaactatc gctataaccc gattcattgg aaagtggcgg aagtgattgc gaaaggcgaa  480
attggcgaag tgaaaagcgt gcattttgaa tggctgctgg ataccgtgca tggcgcggat  540
tattttcgcc gctggcatcg ctataaagat cgcagcggcg gcctgatgat tcataaaagc  600
agccatcatt ttgatctggt gaacttttgg attcagagcg tgccgcagag cgtgtttggc  660
atgggcagcc tggcgtttta tggcaaagaa aacggcaaaa aaagcggctg gggcaaaaac  720
tatgaacgcg cgcgcgatgc gaaagaagcg gaaaacgatc cgtttgcgat tcatctgggc  780
gatgaagaag gcctgaaagg cctgtatttt gatgcggaac atattgatgg ctatcatcgc  840
gatatgaacg tgtttgcgga tgatattacc attgaagatg atatgagcgt gctggtgcat  900
tatgaaagcg gcgtgaacat gacctatcat ctgaccgcgt atagcccgtg ggaaggctat  960
cgcgtgatgt ttaacggcac ccatggccgc ctggaactgg aagtggtgga aaacgcgttt  1020
cgcctgccga ttccgaaagg cagcaacaac gcgagcgaac atgtgcatgg cgatagcgcg  1080
ctgccgaacg aaggccatag caaaattacc ctgcataaac tgtggcagca gccggtgaac  1140
gtgccgtatc aggaagcgaa aggcggccat ggcggcggcg atgaagcgat gctggatgaa  1200
atttttggcc cgaaagaagg cgaagaagaa cgcaaatgcc cggtgaacgg cctgagcgcg  1260
gatcagaaag atggcgcgct ggcgatggcg gtgggcctgg cggcgaacga aagctttaaa  1320
aacggcaaac aggtgtttat taaagaactg ctgggcggca ccctg                  1365

SEQ ID NO: 38          moltype = AA  length = 455
```

-continued

```
FEATURE                Location/Qualifiers
source                 1..455
                       mol_type = protein
                       organism = Cryptococcus neoformans
SEQUENCE: 38
MTAVNSNQGT GKLSGRVGIV GTGHRARLYT TAVASRANTS LVALCDTNDA RMDWHNKMLR  60
EAGRPEAKKY AAEDFRKMLE QEKLDVLVVT TIDYTHDMYI IPALKAGIKV LSEKPMTTNV  120
DKCKAILNAV NESKGSLTVL FNYRYNPIHW KVAEVIAKGE IGEVKSVHFE WLLDTVHGAD  180
YFRRWHRYKD RSGGLMIHKS SHHFDLVNFW IQSVPQSVFG MGSLAFYGKE NGKKSGWGKN  240
YERARDAKEA ENDPFAIHLG DEEGLKGLYF DAEHIDGYHR DMNVFADDIT IEDDMSVLVH  300
YESGVNMTYH LTAYSPWEGY RVMFNGTHGR LELEVVENAF RLPIPKGSNN ASEHVHGDSA  360
LPNEGHSKIT LHKLWQQPVN VPYQEAKGGH GGGDEAMLDE IFGPKEGEEE RKCPVNGLSA  420
DQKDGALAMA VGLAANESFK NGKQVFIKEL LGGTL                            455

SEQ ID NO: 39          moltype = DNA  length = 1338
FEATURE                Location/Qualifiers
source                 1..1338
                       mol_type = genomic DNA
                       organism = Cryptococcus neoformans
CDS                    1..1338
SEQUENCE: 39
atgagcgcga ttcgcgcgct gaacatgcgc aaaaccgcga gcgcgctgaa agcgccggtg  60
gcgtttaaac gcaccctggc gaccccggtg aacagcctgt ataccagcgt gctgccggcg  120
aaaattccgg cggcgctgca tctgaaaagc ggccagagct attttggcag cagctttggc  180
agcgaaaaca gcaaatttgg cgaaaccgtg tttagcacca gcattaccag ctataccgat  240
agcatgaccg atccgagcta tctgggccag attctggtgt ttaccagccc gatgattggc  300
aactatggcg tgccgagcaa caccagcagc cagtttccgg gcattccgtt tctggaaagc  360
gaaaaaattc agtgcaccgg cgtggtggtg agcgatgtgg cgctgaaata tagccattat  420
caggcggtgg aaagcctgca tgaatggtgc aaacgctatg atgtgccggg cattaccggc  480
gtggataccc gcgcgattac cagcctgctg cgcgatcagg gcaccaccct gggccgcctg  540
gcggtgggcg atgaagcggg caaaccggcg ccgcaggaag cggaatattg ggatccgagc  600
aaagaaaacc tggtggcgca ggcgagcacc aaaaaagcgt atgtgctgaa cgaaaaaggc  660
agcggcccgc gcattgcggt gctggatttt ggcaccaaag cgaacattct gcgcagcctg  720
attcgccgcg atgcggtggt gaccgtgctg ccgtgggatt ttgattttaa caccgtgcgc  780
gatcagtttg atggcctgtt tctgagcaac ggcccgggcg atccgaaaat gattatggat  840
agcgcgatgc gcgtgcgcca gaccattaac gaatggaaca aaccgatttt tggcatttgc  900
atgggccatc aggtgctggg cctggcggcg ggcctggaag cgtatcgcat gacctttggc  960
aaccgcggcc ataaccagcc ggtgctggcg ctggcgagca gcggcagcat taaagcgggc  1020
cgcgtgtatg tgaccagcca gaaccatcag tatgcgctgc gcctgaccga agattttccg  1080
gaaggctggg cgccgttttt tattaactgc aacgatagca gcgtggaagg cattattagc  1140
accccggaaa gcggcaaacg catttggggc gtgcagtttc atccggaaag cgcgggcggc  1200
ccgctggata ccattgaaat gtttaccgat tttgtgaacg aatgcgatgt gagccgcaaa  1260
ggctttagcg gcagcgcgat gattgcgaac gaagtgaaag tggatggcca tgcggcgaaa  1320
gcggcgagcg tgagcgcg                                               1338

SEQ ID NO: 40          moltype = AA  length = 446
FEATURE                Location/Qualifiers
source                 1..446
                       mol_type = protein
                       organism = Cryptococcus neoformans
SEQUENCE: 40
MSAIRALNMR KTASALKAPV AFKRTLATPV NSLYTSVLPA KIPAALHLKS GQSYFGSSFG  60
SENSKFGETV FSTSITSYTD SMTDPSYLGQ ILVFTSPMIG NYGVPSNTSS QFPGIPFLES  120
EKIQCTGVVV SDVALKYSHY QAVESLHEWC KRYDVPGITG VDTRAITSLL RDQGTTLGRL  180
AVGDEAGKPA PQEAEYWDPS KENLVAQAST KKAYVLNEKG SGPRIAVLDF GTKANILRSL  240
IRRDAVVTVL PWDFDFNTVR DQFDGLFLSN GPGDPKMIMD SAMRVRQTIN EWNKPIFGIC  300
MGHQVLGLAA GLEAYRMTFG NRGHNQPVLA LASSGSIKAG RVYVTSQNHQ YALRLTEDFP  360
EGWAPFFINC NDSSVEGIIS TPESGKRIWG VQFHPESAGG PLDTIEMFTD FVNECDVSRK  420
GFSGSAMIAN EVKVDGHAAK AASVSA                                      446

SEQ ID NO: 41          moltype = DNA  length = 843
FEATURE                Location/Qualifiers
source                 1..843
                       mol_type = genomic DNA
                       organism = Cryptococcus neoformans
CDS                    1..843
SEQUENCE: 41
atgagcgtgc cgagcctgaa aagcgcgctg aaaaaaccga ccaaaagctt tgataccccg  60
ccggcgggcc cgagcaaact gagcgtggcg gcggcggtgc cggaaaaaag caaagcgaaa  120
gcgaaacaga gcgtgagcat tgcggaaaaa ccgcagcgcc tgcgcggccc ggatctggaa  180
agcgaaagcg aaggcaacgc gagcggcttt gaagatgaaa gcgcgagcga agtggaagtg  240
gatgaagatg aagaaatgaa caccgatgaa gaaattgaaa aagcgaaaga aggcaaaccg  300
aaaaaaagca ccaaacgcaa aaaagcgccg accaccgcgg cggattttgg cgcgaccctg  360
accagcctgc tggcggatcc gctgaccaaa agcaacaaaa aagcgaaaac cgcggatagc  420
accaaaaaag cggcggcggc gccgattctg gcgctgagcg cgcataaact gccgaccaaa  480
gcgagcgtga gcctggaagc gaaagcgaaa cgccagctga aagcggaaaa agaagaaaaa  540
gaagatcgcg cgcgcgtgca gaacgtgctg gaaggctgga gcggcgatgg cgtggtgggc  600
ggccaggaat ttgaacgcaa cctgcgcaaa accgcgcaga aaggcgtggt gaaactgttt  660
aacgcgattc tggtggcgag caaaaacgcg gaagcggcgc agaccaccct gagcgaaaaa  720
```

-continued

```
gcgcgcctga aaccggaagc ggcgaaaaaa aaagaaaaag ataacattct gggccgcggc  780
ggcaaagaag atgtgctgac caaagaaagc tttctggaaa tggtgcgcaa aggcagcagc  840
aaa                                                                 843

SEQ ID NO: 42          moltype = AA  length = 281
FEATURE                Location/Qualifiers
source                 1..281
                       mol_type = protein
                       organism = Cryptococcus neoformans
SEQUENCE: 42
MSVPSLKSAL KKPTKSFDTP PAGPSKLSVA AAVPEKSKAK AKQSVSIAEK PQRLRGPDLE  60
SESEGNASGF EDESASEVEV DEDEEMNTDE EIEKAKEGKP KKSTKRKKAP TTAADFGATL  120
TSLLADPLTK SNKKAKTADS TKKAAAAPIL ALSAHKLPTK ASVSLEAKAK RQLKAEKEEK  180
EDRARVQNVL EGWSGDGVVG GQEFERNLRK TAQKGVVKLF NAILVASKNA EAAQTTLSEK  240
ARLKPEAAKK KEKDNILGRG GKEDVLTKES FLEMVRKGSS K                       281

SEQ ID NO: 43          moltype = DNA  length = 600
FEATURE                Location/Qualifiers
source                 1..600
                       mol_type = genomic DNA
                       organism = Cryptococcus neoformans
CDS                    1..600
SEQUENCE: 43
atgacctgcg cgctgattcc gctgctgcgc aaaagcgatc tgcgcagcgt ggtgattatt  60
gcgagcattg cgggcctggc gaaccagcgc gcgaccggca gcgtgagcta tggcgtgagc  120
aaagcggcgg cgattcatct gggcaaactg ctggcgggcc gcctgcatcc gctgaaaatt  180
cgcgtgaaca ccatttgccc gggcattttt ccgagcgaaa tgaccggcaa aaacgatgcg  240
ggccagggcc tggaatatga tattggcgaa attccgacca aagcggcgaa acgcagcacc  300
gtgggccgcc cgggcctgcc ggaagaaatt gtgggcccgg tgctgctgct gagcagcaaa  360
gcgggcggct attttgatgg cgcgatgctg accgtggatg gcggccgcct gatggtgagc  420
ggcccgtttt gctttgtgtt tagcccgagc agcctgccgg tggataacct gcgctgcttt  480
ctgctgctga ccaccgtggg caaccgcgtg ccggcgttta tgatggtgag cgattgcctg  540
cgcattcgca tttttgaact gaacgaacag cgcaaaaacg aaaccgatgt ggaaatgggc  600

SEQ ID NO: 44          moltype = AA  length = 200
FEATURE                Location/Qualifiers
source                 1..200
                       mol_type = protein
                       organism = Cryptococcus neoformans
SEQUENCE: 44
MTCALIPLLR KSDLRSVVII ASIAGLANQR ATGSVSYGVS KAAAIHLGKL LAGRLHPLKI  60
RVNTICPGIF PSEMTGKNDA GQGLEYDIGE IPTKAAKRST VGRPGLPEEI VGPVLLLSSK  120
AGGYFDGAML TVDGGRLMVS GPFCFVFSPS SLPVDNLRCF LLLTTVGNRV PAFMMVSDCL  180
RIRIFELNEQ RKNETDVEMG                                               200

SEQ ID NO: 45          moltype = DNA  length = 1440
FEATURE                Location/Qualifiers
source                 1..1440
                       mol_type = genomic DNA
                       organism = Cryptococcus neoformans
CDS                    1..1440
SEQUENCE: 45
atgctggtga acagcagcag catgctggtg acccgcaccc atggcctgat gggcgatgaa  60
gcgtggaaag aactggcgaa atatggcctg acccgctgga gcgatgatgg cgcgtttctg  120
accgtgccgg cgcgcggctg cagcatgtgc gaagtggatc cggtgctgtg cgaagaaatt  180
ggcgaagata acctgaaacg cagcctggcg tttagcggca ccaaccgccg cctgaaacgc  240
gtgctggcga aactgcgccg cggcgaaacc attaacgtgg gcgcgattgg cggcagcgtg  300
accaaaggct atggcctgaa ccgctataac gaaccgtatt atccggatac cccgaccaac  360
ctgcatcgca ttatttttga tcatctggtg agcctgtatc cggcgccgaa cggcgtgaaa  420
accgatgata gcggccgcaa agaaggcaaa catggctata ttaacggcgg ccagggcgcg  480
accggcaccg gctattttag ctattgctgg gaagaacatg tgccggcgga tctggatctg  540
atttttctgg aacaggcgat taacgatgaa ctgctgctgc gcaacattga tagctatgaa  600
ctgctggtgc gcagcctgct ggatctgccg accagcccgg cgattgtgaa cctgcatgtg  660
tttgcgctga tgtttaacag cattaccctg ggcggcgatc tgcatcagag cattgcgcag  720
ttttatgatc tgccggtgct gagcctgcgc aacgcgctgc tgaacgatat gctgaaaaac  780
gaaagcctga ttagcgaata ttttttttgtg catccggaag gcgatattga tctgcgccat  840
attagccgca aaggccataa cgtgatgggc cgcattggcg cggcgtatat ggatagccag  900
atttgcgaaa tggataaata tgaacagggc attccgggcg cggatagcat gagcattgat  960
cagctgtatc cggtggaacc gattccgcgc atgcagatta acatgaaata tgataaagat  1020
ctggtgctgc cgaccattaa accgcagtgc tttagcgcga acagcgaaaa acatccgctg  1080
gtgccggtgg aaaacaacgg ctggcgcaaa tggaactgga aagaaaaaca ttatctggtg  1140
gcggatgtgc cgggcagccg cgtgagcttt aaactgaaaa ccaacatggg caaaattgaa  1200
gtgcagtatc tgcgcagcta tcagtatcat cagggcagcg cgaaatgctg ggtggatgaa  1260
gaagtggaaa aagcgattaa actggatggc tattggaaag aaccgtataa cattggccgc  1320
gcggtgacca ttcgcgaagg cctggaaccg ggcgaacata ccctgacctg cgaactgctg  1380
aaacagaccg cggatccgga aggcggcctg gaatttcgcc tgattagcat tatgagcatt  1440

SEQ ID NO: 46          moltype = AA  length = 480
FEATURE                Location/Qualifiers
```

-continued

```
source                  1..480
                        mol_type = protein
                        organism = Cryptococcus neoformans
SEQUENCE: 46
MLVNSSSMLV TRTHGLMGDE AWKELAKYGL TRWSDDGAFL TVPARGCSMC EVDPVLCEEI  60
GEDNLKRSLA FSGTNRRLKR VLAKLRRGET INVGAIGGSV TKGYGLNRYN EPYYPDTPTN  120
LHRIIFDHLV SLYPAPNGVK TDDSGRKEGK HGYINGGQGA TGTGYFSYCW EEHVPADLDL  180
IFLEQAINDE LLLRNIDSYE LLVRSLLDLP TSPAIVNLHV FALMFNSITL GGDLHQSIAQ  240
FYDLPVLSLR NALLNDMLKN ESLISEYFFV HPEGDIDLRH ISRKGHNVMG RIGAAYMDSQ  300
ICEMDKYEQG IPGADSMSID QLYPVEPIPR MQINMKYDKD LVLPTIKPQC FSANSEKHPL  360
VPVENNGWRK WNWKEKHYLV ADVPGSRVSF KLKTNMGKIE VQYLRSYQYH QGSAKCWVDE  420
EVEKAIKLDG YWKEPYNIGR AVTIREGLEP GEHTLTCELL KQTADPEGGL EFRLISIMSI  480

SEQ ID NO: 47           moltype = DNA  length = 1176
FEATURE                 Location/Qualifiers
source                  1..1176
                        mol_type = genomic DNA
                        organism = Cryptococcus neoformans
CDS                     1..1176
SEQUENCE: 47
atgagctttg atgcggtggt gattggcagc ggcgtgattg gcctgagcat tgcgcgcgaa  60
ctgcataacc gcggcctgaa agtggcgatt gtggcgcgcg atctggcgga agatagcatt  120
agcgtgggct ttgcgagccc gtgggcgggc tgcaactggt ttagctttgc ggaaggcggc  180
accccggcgg cggaatggga taccattacc tttggcaaac tggcgaaact ggcgaaagat  240
catccgcata tttgccagaa aattccgttt tgcagcgtgt gggatctgcc gaaaagcgat  300
gcggaaagcg aaccgtggtt taaagatctg gtgtttgatt ataaaaacct gaaaagcacc  360
ccgggccagc cgctgccggg cggcaaaaaa tttggccata gctttgcgag ctatgtgctg  420
catgcgccga actatattcg ccatctgagc agcgaaaccc gcgcgctggg cattccggtg  480
catcgctatc gcctgagcag cctggatgaa gcgtataacc tgagcggcat tggcaaagtg  540
agcctggtgg tgaacgcgag cggcctgggc gcgaaagcgc tgattggcgt ggaagatgaa  600
aaagtgtatc cgggccgcgg ccagaccgtg ctggtgcgcg cgccgggctt taaagcgtgc  660
attatgcata ccgaaggctt ttatgcggat ctggatgaaa gcggccgcga agtgaccccg  720
ccgccgccgg cgtatattat tccgcgcccg ggcccggaag gccatgtggt gctgggcggc  780
gtgtatcagc gcgataactg gagcaccctg ccggatctga aagaagcgga acgcattctg  840
aaagattgct ataacctggc gccggaactg gcgggcccga acggcaaaac ctggaaagat  900
attgaaatta ttagccataa cgtgggcctg cgcccggcgc gcgaaggcgg cccgcgcctg  960
gaaattgaag aacgcgaagt gggcaccggc gcgaacgaag gcaacgcgta tgatgtggcg  1020
ccgatgattg gccgcattgg cgaacgccgc aaagtggcgg tggtgcatgc gtatggcatt  1080
ggcagcgcgg gctttcaggc gagcctgggc atggcggaaa aagcgagcga tctgaccgtg  1140
aaatatctga gcggcaaacg cagcccggcg cgcctg                           1176

SEQ ID NO: 48           moltype = AA  length = 392
FEATURE                 Location/Qualifiers
source                  1..392
                        mol_type = protein
                        organism = Cryptococcus neoformans
SEQUENCE: 48
MSFDAVVIGS GVIGLSIARE LHNRGLKVAI VARDLAEDSI SVGFASPWAG CNWFSFAEGG  60
TPAAEWDTIT FGKLAKLAKD HPHICQKIPF CSVWDLPKSD AESEPWFKDL VFDYKNLKST  120
PGQPLPGGKK FGHSFASYVL HAPNYIRHLS SETRALGIPV HRYRLSSLDE AYNLSGIGKV  180
SLVVNASGLG AKALIGVEDE KVYPGRGQTV LVRAPGFKAC IMHTEGFYAD LDESGREVTP  240
PPPAYIIPRP GPEGHVVLGG VYQRDNWSTL PDLKEAERIL KDCYNLAPEL AGPNGKTWKD  300
IEIISHNVGL RPAREGGPRL EIEEREVGTG ANEGNAYDVA PMIGRIGERR KVAVVHAYGI  360
GSAGFQASLG MAEKASDLTV KYLSGKRSPA RL                                392

SEQ ID NO: 49           moltype = DNA  length = 198
FEATURE                 Location/Qualifiers
source                  1..198
                        mol_type = genomic DNA
                        organism = Cryptococcus neoformans
CDS                     1..198
SEQUENCE: 49
atgccgggct ttcaggatgt gatttataac accttttttc gccgcaacag cgtgtttgtg  60
gcgaccacct ttattgcggc gtttagcttt agcatgggct ttgatctggc gaccaccgcg  120
ttttgggata gccataaccg cggcaaacag tggaaagata ttcgccataa atatattgaa  180
gcggcgggcg atgatgaa                                                198

SEQ ID NO: 50           moltype = AA  length = 66
FEATURE                 Location/Qualifiers
source                  1..66
                        mol_type = protein
                        organism = Cryptococcus neoformans
SEQUENCE: 50
MPGFQDVIYN TFFRRNSVFV ATTFIAAFSF SMGFDLATTA FWDSHNRGKQ WKDIRHKYIE  60
AAGDDE                                                             66

SEQ ID NO: 51           moltype = DNA  length = 1368
FEATURE                 Location/Qualifiers
source                  1..1368
```

-continued

```
                        mol_type = genomic DNA
                        organism = Cryptococcus neoformans
CDS                     1..1368
SEQUENCE: 51
atgagcagcg gcaacgtgcc gaaaattgaa cgcctgagct gcgtgccgaa cgattatccg  60
tggggcgaag tgggcaacga tagcctggcg gcgcgcctgg cgagcaaaaa cggcgcggtg  120
agctttgatc tgaaaccgga acaggcgtat gcggaactgt ggatgggcac ccatccgaac  180
aacccggcgc atctgtttag cagcccggat accctgctga gcacccatct gaaaaaaaac  240
ccgagcctgc tgggcgcggc gaaccgcttt agcccgccgt ttaccggcgc gaaaggcagc  300
ggcgcggaag gccaggaaga aggccatgtg ccgtttctgt ttaaagtgct gacctgcaaa  360
caggcgctgc cgctgcagat tcatccggat aaagcgctgg cgaaaaaact gcatgaagaa  420
aacccgaaac agtttggcga tattaaccat aaaccggaaa ttgcggtgtg cctgagcgat  480
cgctttctgg gctttgcgag ctttcgcccg tatgataaaa ttgcgagcct gctgaaaagc  540
gtgcaggaaa ttagcctgct gccgagcctg ctgcagaaaa gcattaaaag ctttattagc  600
gcgccgagcg cggaaaccct gcagccgacc tgggaaggct ttattaaact gggcgataac  660
gaagaaagcg tgaaaaaatt tagcgatcgc gtgctgagcc agggcctgaa agcgtttgat  720
agcgtggata ttgaagatga agataaaaac cgcctggtgc gcgcggtgga actgggcaaa  780
aaatataacc cgggcgatgc gggcctgttt agcagcctgc tgtttctgaa cctgattgaa  840
ctgaaaaaag atcagggcat gtatgtgggc gcggatggcc cgcatgcgtg gctggaaggc  900
gaaattgtgg aactgatggc gattagcgat aacgtgctga acgtgggctt taccagcgat  960
gatagcaaag atgatccgag cctggtggcg aaagcggtga cctgcacccc gaaagcgatt  1020
aaagatctgc tgctggatgc gagcaaatat agcaaaagcc agaacggccg caccaccgtg  1080
tatagcaccc cgtttgaaga atttagcatt atgaaaattg cgggcgatga aattctgagc  1140
ccgctggatg gcgcgggcgt ggcggtggtg ctggaaggcg aatggaccgt ggaagatcag  1200
gaaggcacca aacgcggcgg cgaaggcacc gatggcgaag gcggcgaagg caccatttgg  1260
tttattggca gcgcgaccga aaccaaatgg accgcgaaag gcggcaaagg ccagatttgg  1320
attgcgtttt atgataaaac cgcgaaaaaa gatgatgtgg gcaaaaaa              1368

SEQ ID NO: 52           moltype = AA  length = 456
FEATURE                 Location/Qualifiers
source                  1..456
                        mol_type = protein
                        organism = Cryptococcus neoformans
SEQUENCE: 52
MSSGNVPKIE RLSCVPNDYP WGEVGNDSLA ARLASKNGAV SFDLKPEQAY AELWMGTHPN  60
NPAHLFSSPD TLLSTHLKKN PSLLGAANRF SPPFTGAKGS GAEGQEEGHV PFLFKVLTCK  120
QALPLQIHPD KALAKKLHEE NPKQFGDINH KPEIAVCLSD RFLGFASFRP YDKIASLLKS  180
VQEISLLPSL LQKSIKSFIS APSAETLQPT WEGFIKLGDN EESVKKFSDR VLSQGLKAFD  240
SVDIEDEDKN RLVRAVELGK KYNPGDAGLF SSLLFLNLIE LKKDQGMYVG ADGPHAWLEG  300
EIVELMAISD NVLNVGFTSD DSKDDPSLVA KAVTCTPKAI KDLLLDASKY SKSQNGRTTV  360
YSTPFEEFSI MKIAGDEILS PLDGAGVAVV LEGEWTVEDQ EGTKRGGEGT DGEGGEGTIW  420
FIGSATETKW TAKGGKGQIW IAFYDKTAKK DDVGKK                           456

SEQ ID NO: 53           moltype = DNA  length = 1962
FEATURE                 Location/Qualifiers
source                  1..1962
                        mol_type = genomic DNA
                        organism = Cryptococcus neoformans
CDS                     1..1962
SEQUENCE: 53
atgacccgcg attttgatag cctgtttttt accggcccga tttttgtgga ttatagcttt  60
accgcgcgcc atctggaaag ctttctgagc agctttccgc cgcaggtgag ccatgcgatg  120
agcagcgcga gcaccccgac cgcgccgtat ctggaagatc tggtgcgcaa cagcctggat  180
cagaccctgc cgtgggtggt gcagaaatat ggcggcacca gcgtgggcaa aagcctggat  240
aacattacca aaattgtggg cagctatatt gataacggca gcaaagtggc gattgtgtgc  300
agcgcgcgca gcacccagac caaaagcctg ggcaccacca acctgctgct gcaggcgagc  360
cgcgaagcgc tgcagccggc gctgagcagc agcggcgatg gccgcagcgg cagcatgagc  420
ggcaccgcga ccccgtttta tccgaaacgc gtgggcagcg gctttttttgg caaagatcag  480
agcaccagca tggtgagcag cgtgagcagc ctgagccagc tggaaccgca gctgggccgc  540
agcggcagcc cgagcccgtt tcagagcagc agcagccgca gcccgccgcg cagcccggcg  600
accccgagcc aggatagcag cgtgagccag gaaccggcgt ttcatgcgac cgtggatctg  660
attaaaaaag gccatctgga agcggcgcgc gcgagcctga aagaaggccc gctgcgcgat  720
gaactggaag aagaaattag acgcgattgc gaaagcctgc gcagctttct gtatgcggcg  780
cagattattg atgaaattag cccgcgcagc caggatagca ttgtgggcac cggcgaacgc  840
ctggcgtgca aaattgtggc ggcggcgctg cgcgatcgcg gcgtggatag cgaactggtg  900
gtgctggata acattgtgga tgcgagcatg agcgcggcga gcgaagcgat tagcgtggat  960
gcgggcgatc agggcgtggc gcagctgggc caggaatttt atgatcagct gagctttcgc  1020
ctgggcgaac gcctgcgcga atgcggccag cgcgtgccgg tggtgaccgg ctattttggc  1080
ccggtgccgg gcagcctgct ggcgcagatt ggccgcggct ataccgatct gtgcgcggcg  1140
ctgtgcgcgg tgggcctgaa agcgagcgaa ctgcaggtgt ggaaagaagt ggatggcatt  1200
tttaccgcgg atccgcgcaa agtgccgagc gcgcgcctgg tgccgattat taccccggat  1260
gaagcggcgg aactgaccta ttatggcagc gaagtgattc atccgtttac catggaacag  1320
gtgattcgcg cgcgcattcc gattcgcatt aaaaacgtgg aaaacccgag cggcgcgggc  1380
accgtgattt atccggatct gggctttccg cgcggcctgg ataccgaacc gccgaaagcg  1440
gaacgcattg tggaaggcgt ggatgaacgc atgccgaccg cggtgaccat taaagatgaa  1500
attattgtgc tgaacattca tagcaaccgc aaaaccctga gccatggctt tctggcgcgc  1560
atttttggca ccctggatcg cgcgggcgtg gtggtggatc tgattagcac cagcgaagtg  1620
catgtgagca tggcgatgca ggattttctg aaccgcaaac gcctggaacg cctggtgaaa  1680
gatctggaaa aaattggcga agtgaccgtg agcaaagata tggcgattct gagcctggtg  1740
```

```
ggccgcaaca tgcgcaacgc gattggcagc gcgggcctga tgtttgcgag cctggcgcgc  1800
gcgatgatta acattgaaat gattagccag ggcgcgagcg aaattaacat tagctgcgtg  1860
attgaaaaca aagatgcgat taaagcgctg aacgtgattc atgaaagctg cctgagctat  1920
ccgcgcagcc cggcgaccga aatggcgggc ctgcagctgc ag                     1962

SEQ ID NO: 54          moltype = AA  length = 654
FEATURE                Location/Qualifiers
source                 1..654
                       mol_type = protein
                       organism = Cryptococcus neoformans
SEQUENCE: 54
MTRDFDSLFF TGPIFVDYSF TARHLESFLS SFPPQVSHAM SSASTPTAPY LEDLVRNSLD  60
QTLPWVVQKY GGTSVGKSLD NITKIVGSYI DNGSKVAIVC SARSTQTKSL GTTNLLLQAS  120
REALQPALSS SGDGRSGSMS GTATPFYPKR VGSGFFGKDQ STSMVSSVSS LSQLEPQLGR  180
SGSPSPFQSS SSRSPPRSPA TPSQDSSVSQ EPAFHATVDL IKKGHLEAAR ASLKEGPLRD  240
ELEEEIERDC ESLRSFLYAA QIIDEISPRS QDSIVGTGER LACKIVAAAL RDRGVDSELV  300
VLDNIVDASM SAASEAISVD AGDQGVAQLG QEFYDQLSFR LGERLRECGQ RVPVVTGYFG  360
PVPGSLLAQI GRGYTDLCAA LCAVGLKASE LQVWKEVDGI FTADPRKVPS ARLVPIITPD  420
EAAELTYYGS EVIHPFTMEQ VIRARIPIRI KNVENPSGAG TVIYPDLGFP RGLDTEPPKA  480
ERIVEGVDER MPTAVTIKDE IIVLNIHSNR KTLSHGFLAR IFGTLDRAGV VVDLISTSEV  540
HVSMAMQDFL NRKRLERLVK DLEKIGEVTV SKDMAILSLV GRNMRNAIGS AGLMFASLAR  600
AMINIEMISQ GASEINISCV IENKDAIKAL NVIHESCLSY PRSPATEMAG LQLQ        654

SEQ ID NO: 55          moltype = DNA  length = 1269
FEATURE                Location/Qualifiers
source                 1..1269
                       mol_type = genomic DNA
                       organism = Cryptococcus neoformans
CDS                    1..1269
SEQUENCE: 55
atgccgaaac agtggccgac cattgtgaaa ctggaaacct ttattccgag cgcgcatggc  60
agcggcggcg attatcatcg ccagggcggc gatcattgga ttgtgcaggg caacattagc  120
tgcccgatgc ataaatatga agaatataaa gtgagccgca ccagctgggg cattggcgtg  180
ctgggcagca tttttgtgaa agtgcatgcg agcgatggca ccgtgggcta tgcgaccggc  240
tttggcggcc cgccggcgtg ctggctgatt gaagaacatt ttaaacgctt tattgtgggc  300
caggatccgc gcgataccaa caaaatgtgg gatcagatgt ttcgcgcgag catgttttat  360
ggccgcaaag gcctgccgct ggcggcgatt agcgtggtgg atctggcgat ttgggatctg  420
ctgggcaaaa ttcgcggcga accgatttat aaaatgattg gcggccgcac caaaaaagat  480
attccgctgt atctgaccgg cccgcgcccg gaagtggcga aaaaactggg cttttggggc  540
agcaaagtgg cgctgccgca tggcccgccg gatggccatg aaggcattcg caaaaacgtg  600
gaatatctga aagcgtgcaa agaagcggtg ggcccggatt atccggtgca ggtggattgc  660
tatatgagcc tggatgtgcc gtataccatt gcgctggtga aagcgtgcga aaaagcgggc  720
gtggaaatta actggtggga agaagtgctg catccggatg attttgatgg ccatattaaa  780
ctgaaagaag cgctgccgta tgtgaaattt accaccggcg aacatgaata tagcaaatat  840
ggctttcgca aactgattga aaaccgcgcg gtggatatta ttcagccgga tgtgatgtgg  900
ctgggcggcc tgaccgaact gattaaagtg gcggcgatgg cggcggcgta tgatattccg  960
gtggtgccgc atggcagcgg cccgtatagc tttcaggcga ttatgagctt tccgaacagc  1020
gatttttgcg aatatattgc gaacagcccg gatggcaaaa gcattgaacc gagctttggc  1080
aacctgtttc tgaacgaagt gctgccgcgc aacggccgcg tggatctgac cgatgaaccg  1140
ggctttggcc tggaactgaa cccgagcgcg gaactggtgc cgtataaaag ctttttttacc  1200
ccgagcaaaa gcctgggcgc ggcgggcgaa gtggaagatg atggcaaagc gaaagtgaac  1260
ggcaaacat                                                          1269

SEQ ID NO: 56          moltype = AA  length = 423
FEATURE                Location/Qualifiers
source                 1..423
                       mol_type = protein
                       organism = Cryptococcus neoformans
SEQUENCE: 56
MPKQWPTIVK LETFIPSAHG SGGDYHRQGG DHWIVQGNIS CPMHKYEEYK VSRTSWGIGV  60
LGSIFVKVHA SDGTVGYATG FGGPPACWLI EEHFKRFIVG QDPRDTNKMW DQMFRASMFY  120
GRKGLPLAAI SVVDLAIWDL LGKIRGEPIY KMIGGRTKKD IPLYLTGPRP EVAKKLGFWG  180
SKVALPHGPP DGHEGIRKNV EYLKACKEAV GPDYPVQVDC YMSLDVPYTI ALVKACEKAG  240
VEINWWEEVL HPDDFDGHIK LKEALPYVKF TTGEHEYSKY GFRKLIENRA VDIIQPDVMW  300
LGGLTELIKV AAMAAAYDIP VVPHGSGPYS FQAIMSFPNS DFCEYIANSP DGKSIEPSFG  360
NLFLNEVLPR NGRVDLTDEP GFGLELNPSA ELVPYKSFFT PSKSLGAAGE VEDDGKAKVN  420
GKH                                                                423

SEQ ID NO: 57          moltype = DNA  length = 1743
FEATURE                Location/Qualifiers
source                 1..1743
                       mol_type = genomic DNA
                       organism = Cryptococcus neoformans
CDS                    1..1743
SEQUENCE: 57
atggcgaacg cgccgcatgg cggcgtgctg aaagatctgc tggtgcgcga tgcggcgctg  60
catgatagcc tgctgcagga agcgcgcagc ctgaacgata tttttctgac cgaacgccag  120
ctgtgcgatc tggaactgat tctgaacggc ggctttagcc cgctggaagg ctttatgaac  180
gaacgcgatt ataccagcgt ggtggaaacc ctgcgcctgg cgccgtataa cggccagaaa  240
```

-continued

```
catggcgatg tgtttccgat tccgattacc ctggatgtga gccaggaaga tattaacacc  300
ctgggcctga aacagggcgg ccgcgtggcg ctgcgcgatc cgcgcgatga tgcggcgctg  360
gcgattctga ccgtgagcga tatttatcgc ccgaacaaag cgattgaagc ggaaaaagtg  420
atgggcgcgg atgatattgc gcatccgagc gtggcgtatc tgcgcaacaa cgtgaaagaa  480
ttttatgtgg gcggcaaagt gcaggcgatt caggcgccga cccattttga ttatgtgccg  540
ctgcgcttta ccccggcgga actgcgcgcg cattttcata aactggcgtg gcgcaaagtg  600
gtggcgtttc agacccgcaa cccgatgcat cgcgcgcatc gcgaactgac cgtgcgcgcg  660
gcgcgccagc gccgcgcgaa cgtgctgatt catccggtgg tgggcctgac caaaccgggc  720
gatgtggatc attataccg  cgtgcgcgcg tatcaggcgc tgatgccgag ctatccggaa  780
ggcatggcgc atctggcgct gctgccgctg gcgatgcgca tggcgggccc gcgcgaagcg  840
gtgtggcatg cggtgattcg caaaaacttt ggcgcgaccc attttattgt gggccgcgat  900
catgcgggcc cgggcaaaaa cagccagggc caggattttt atggcccgta tgatgcgcag  960
gaactggtga cccagtttaa agatgaactg cagattgaaa tggtgccgtt tcaggcgatg  1020
acctatctgc cgggcagcga tgaatatcag ccggtggatg aagtgccgaa aggcaccccg  1080
accgcggata ttagcggcac cgaactgcgc aaacgcctgc gcaccggcgc gagcattccg  1140
gattggttta gctataccgg cgtggtgaaa gtgctgcgcg aaagctatcc gccgcgcccg  1200
cagcagggct ttaccattct gctgaccggc ctgcataaca gcggcaaaga taccattgcg  1260
cgcgcgctgc aggtgaccct gcagcagcag ggcagccgca gcgtgagcct gctgctgggc  1320
gaagaactgc gcagcgatct ggatccgcag attggccgcg cgattacccc ggaacagaaa  1380
catattaacc tggaacgcat tggctttgtg gcgggcgaac tgaccaaagc gggcgcggcg  1440
gtgattgcgg cgccgaccgc gccgtatgaa cgcagccgcc aggcgtttaa aaaacaggtg  1500
gtgggcagcg gcggcggcaa ctattttctg gtgcatgtgg cgaccccgct ggaatggtgc  1560
gaaaaagtgg atcgccgcgg cctgtataaa gcggcgcgcg cgggcgaaat taaaaacctg  1620
accggcgtgg atgatgtgta tgaagcgccg gaagatgcgg atctggtgtg cgatctgcgc  1680
aacgataccg tgccggaaat tgtgcatagc attattatga ttctggaaag ccagaacctg  1740
gtg                                                                1743
```

```
SEQ ID NO: 58          moltype = AA  length = 581
FEATURE                Location/Qualifiers
source                 1..581
                       mol_type = protein
                       organism = Cryptococcus neoformans
SEQUENCE: 58
MANAPHGGVL KDLLVRDAAL HDSLLQEARS LNDIFLTERQ LCDLELILNG GFSPLEGFMN  60
ERDYTSVVET LRLAPYNGQK HGDVFPIPIT LDVSQEDINT LGLKQGGRVA LRDPRDDAAL  120
AILTVSDIYR PNKAIEAEKV MGADDIAHPS VAYLRNNVKE FYVGGKVQAI QAPTHFDYVP  180
LRFTPAELRA HFHKLAWRKV VAFQTRNPMH RAHRELTVRA ARQRRANVLI HPVVGLTKPG  240
DVDHYTRVRA YQALMPSYPE GMAHLALLPL AMRMAGPREA VWHAVIRKNF GATHFIVGRD  300
HAGPGKNSQG QDFYGPYDAQ ELVTQFKDEL QIEMVPFQAM TYLPGSDEYQ PVDEVPKGTP  360
TADISGTELR KRLRTGASIP DWFSYTGVVK VLRESYPPRP QQGFTILLTG LHNSGKDTIA  420
RALQVTLQQQ GSRSVSLLLG EELRSDLDPQ IGRAITPEQK HINLERIGFV AGELTKAGAA  480
VIAAPTAPYE RSRQAFKKQV VGSGGGNYFL VHVATPLEWC EKVDRRGLYK AARAGEIKNL  540
TGVDDVYEAP EDADLVCDLR NDTVPEIVHS IIMILESQNL V                    581
```

```
SEQ ID NO: 59          moltype = DNA  length = 1716
FEATURE                Location/Qualifiers
source                 1..1716
                       mol_type = genomic DNA
                       organism = Cryptococcus neoformans
CDS                    1..1716
SEQUENCE: 59
atgcacatcg catacattct cggcctcgta cccctcgctt tcgccggtgt catcaagcac  60
gaccctccca agttccagcc tattcagtct accaggattg tgcggctgca cccaaacggg  120
gacaaaagca agtgcgttga cctcctgggt aatactcgcc aggatggtca gcccgtgcag  180
atttgcgact gcgacggtac cccggctcag gactgggtcc tcaatgccgg ccgcggtcag  240
accaaggtcc agctcgccgg caccagtttc tgtctcgatg ccacccaccc ttacgcagcc  300
gacgggacca acatgaagat ctggaagtgc ttggacgtcc aacagcaaga ctggtattgg  360
acgagtgata acagaatcgt tctccgcgac cagggcaagt gcctcgactg ggccactggg  420
gatcggtctg atttcaacca gctgcaggtc tggcggtgca gcacggataa caacaatcag  480
gtctggacaa cgggaccgga ctacggtggg aaccatgggg gtgatgctgg tgggaacccc  540
ggaggtaatc aaggcgatga ttcaagaggc aaaaccaata ctggtggaaa ccccggaggt  600
aatcaaggtg gtgattcagg agggaaaacc aatcacatca ttcccgaccc cccagggcca  660
gaccccaaca gcgagcccct caaccccgcc cttgaagcca ttgttaacgt caccgaggca  720
gctggaccct ggccgcccat gatcaacttc gacggcgatt acagcaatga cgacgtgacc  780
gtatcggacc aagtaccgtt cgactactgt atcggggagg ggtctggtaa cccgacggat  840
gatgaaggac agcagcaagg acaaaacttc acagcaaatg tagctgggat agggagagac  900
ttctgcctgg acaattttgg caatcctgac attcggaaca ccatttcttt cgacaacaac  960
accagcattg ggaacggagc ggacactggg cgagcccttc acaagcggac atttgcggat  1020
tcaggggcga cgggtacgcc caaccggtgg agacgagggt cggtgatttc catttgcgtc  1080
gagaggaaca acaattatct ggttccatat gcgtcctccc ccgttcccat ccgagcatcg  1140
gctatcgtcg catccgccat ggtacgtgca atcaacttct ggaacgcagg tctgaacaag  1200
cgattcgtct cgttcgagtt tgtggagaac tgcaacgacg ccgtgttcca tactcttgct  1260
gttgaccaga tcaagtctgc caaagagcct actgtgctcg cgactgcccc cttccctcct  1320
cggggtgaag agggtgctag gaaccgcaac atcttcgtgt ggaatacggc tttcgaggcc  1380
aactttcaga acgtccttac ctttatcatg tcacatgagc tggggcacac tcttggcctg  1440
gcgcatgagg actgcaaatc cagagaccaa ccttgcgaag ttatcactga caaggtggct  1500
gggtcagtcg tggaaagccg tatctccggc agcaccacac agctgttcaa tggccccacc  1560
ccgcttgaca tagcaggggc gaacgagtac tactcacttg cagcgggacc caacaccccg  1620
gagaacatcg tactctggcc tgcgacgagg ggtccgttta tcaactaccc gccgctaccg  1680
```

```
aaatgcaagt ggttcctcgg tatttgctat tactag                       1716

SEQ ID NO: 60          moltype = AA  length = 571
FEATURE                Location/Qualifiers
source                 1..571
                       mol_type = protein
                       organism = Cryptococcus neoformans
SEQUENCE: 60
MHIAYILGLV PLAFAGVIKH DPPKFQPIQS TRIVRLHPNG DKSKCVDLLG NTRQDGQPVQ  60
ICDCDGTPAQ DWVLNAGRGQ TKVQLAGTSF CLDATHPYAA DGTNMKIWKC LDVQQQDWYW  120
TSDNRIVLRD QGKCLDWATG DRSDFNQLQV WRCSTDNNNQ VWTTGPDYGG NHGGDAGGNP  180
GGNQGDDSRG KTNTGGNPGG NQGGDSGGKT NHIIPDPPGP DPNSEPLNPA LEAIVNVTEA  240
AGPWPPMINF DGDYSNDDVT VSDQVPFDYC IGEGSGNPTD DEGQQQGQNF TANVAGIGRD  300
FCLDNFGNPD IRNTISFDNN TSIGNGADTG RALHKRTFAD SGATGTPNRW RRGSVISICV  360
ERNNNYLVPY ASSPVPIRAS AIVASAMVRA INFWNAGLNK RFVSFEFVEN CNDAVFHTLA  420
VDQIKSAKEP TVLATAPFPP RGEEGARNRN IFVWNTAFEA NFQNVLTFIM SHELGHTLGL  480
AHEDCKSRDQ PCEVITDKVA GSVVESRISG STTQLFNGPT PLDIAGANEY YSLAAGPNTP  540
ENIVLWPATR GPFINYPPLP KCKWFLGICY Y                            571

SEQ ID NO: 61          moltype = DNA  length = 1500
FEATURE                Location/Qualifiers
source                 1..1500
                       mol_type = genomic DNA
                       organism = Cryptococcus neoformans
CDS                    1..1500
SEQUENCE: 61
atgccgagcc tgacccagac caaagatctg gcgagcctgc tgagcgatgc gagccatttt  60
aaacagaaag gctatattaa cggcgaatgg gtgagcgcga gcgatggcgc gacctttccg  120
ctgtataacc cggcgaccgg cgcgaaactg gcggatatgc cgcatatgcc gcgcagccag  180
gtggcggaag cgattaacgc ggcgaaagcg gcgtttccgg cgtgggcggc gctgaccgcg  240
tatcagcgcc agaactatct gctgaaactg tttaaagaaa tggaagaaca tagcgaagat  300
ctggcgatta ttctgtgcac cgaaaacggc aaaccgctgg cggaaagccg cgtggaaatt  360
agctatggcg cgagctttct gacctggaac gcggcggaag cgctgcgcac ctatggccag  420
accattccga gcccgtttcc gggcacccgc aacaccgtga ttaaacagcc gattggcgtg  480
tgcggcctga ttaccccgtg gaactttccg aacgcgatga ttacccgcaa aatggcgccg  540
gcgctggcgg cgggctgcac cgtggtgatt aaagcgccgg cggaaacccc gctgagcgcg  600
ctggcgatgt gcgtgctgtg cgaacgcgtg ggcattccgc cgggcgtggt gaacgtggtg  660
accatggata aaggccagcg cgaaatggcg gcgggcctgg aactgtgcga aaacgtgaaa  720
gtgagcaaaa ttagctttac cggcagcacc ccggtgggcc gcctgctgat gaaacagagc  780
agcggcaccc tgaaaaaact gagctttgaa ctgggcggca acgcggcgtt tattattttt  840
gatgatgcgg atctggatct ggcggtgaac ggcgtgattc tgagcaaatt tcgcgcggcg  900
ggccagacct gcatttgcgc gaaccgcatt tttgtgcata gcaaaattta tgatgatttt  960
gcgcgccgcc tggtggaacg cgtgaaagcg tttaaagtgg gcaacggcat tgaagaaggc  1020
gtgaccattg gcccgctggt gagccagcgc ggcgtggaaa aagtggaacg ccatgtgcag  1080
gatgcggtgg gcctgggcgc gaaagtgctg gtgggcggca aacgcattga taaaggcgaa  1140
ggcagctgct tttatgaacc gaccgtgctg gtggatgtgc cgcgccagtg cgcggtgagc  1200
aacgaagaaa cctttggccc gctggcgccg ctgtttaaat ttgatgatga agatgatgtg  1260
gtggaacgcg cgaacagcag cgaagtgggc ctggcggcgt atttttttac caaagatctg  1320
gcgcgcaccc atcgcgtggc ggaaaaactg gaagtgggca tggtggcggt gaacaccggc  1380
gcgattgcgc agagctgcgt gccgtttggc ggcgtgaaac agagcggctt tggccgcgaa  1440
ggcggcccga gcggcattga tgaatttatg gtggaaaaac tgattaccat tggcggcctg  1500

SEQ ID NO: 62          moltype = AA  length = 500
FEATURE                Location/Qualifiers
source                 1..500
                       mol_type = protein
                       organism = Cryptococcus neoformans
SEQUENCE: 62
MPSLTQTKDL ASLLSDASHF KQKGYINGEW VSASDGATFP LYNPATGAKL ADMPHMPRSQ  60
VAEAINAAKA AFPAWAALTA YQRQNYLLKL FKEMEEHSED LAIILCTENG KPLAESRVEI  120
SYGASFLTWN AAEALRTYGQ TIPSPFPGTR NTVIKQPIGV CGLITPWNFP NAMITRKMAP  180
ALAAGCTVVI KAPAETPLSA LAMCVLCERV GIPPGVVNVV TMDKGQREMA AGLELCENVK  240
VSKISFTGST PVGRLLMKQS SGTLKKLSFE LGGNAAFIIF DDADLDLAVN GVILSKFRAA  300
GQTCICANRI FVHSKIYDDF ARRLVERVKA FKVGNGIEEG VTIGPLVSQR GVEKVERHVQ  360
DAVGLGAKVL VGGKRIDKGE GSCFYEPTVL VDVPRQCAVS NEETFGPLAP LFKFDDEDDV  420
VERANSSEVG LAAYFFTKDL ARTHRVAEKL EVGMVAVNTG AIAQSCVPFG GVKQSGFGRE  480
GGPSGIDEFM VEKLITIGGL                                         500

SEQ ID NO: 63          moltype = DNA  length = 1200
FEATURE                Location/Qualifiers
source                 1..1200
                       mol_type = genomic DNA
                       organism = Cryptococcus neoformans
CDS                    1..1200
SEQUENCE: 63
atgtgcagca gccatgcgac cgcggtggaa agcgtgagcc cggcgccgcg caaaagccag  60
tatgaagtga aatatgatcc ggatctggtg ctgaaaagcg cggaatttaa agaactgaaa  120
cagggcgata aagaactgga agatccgaaa gcgaacctgg cgtgcgcgta tgatgaaaaa  180
cataacgtga aaatgattaa caaaccgatt ccgaaagcgc gccaggatga agtggtggtg  240
```

```
catattaaag cgaccggcat ttgcggcagc gatgtgcatt tttggaaaca tggccagatt  300
ggcccgacca tgattgtgac cgatacctgc ggcgcgggcc atgaaagcgc gggcgaagtg  360
gtggaagtgg gcccgggcgt ggaacagtgg aaagtgggcg atcgcgtggc gattgaatgc  420
ggcgtgccgt gcggccaggc gagctgcggc ccgtgcgtga ccggccgcta taacgcgtgc  480
ccgcaggtgg tgtttttttag caccccgccg tatcatggca ccctgacccg ctatcatgcg  540
catccggcga gctggctgca tcgcctgccg gataacctga gctatgaaga aggcgcgctg  600
tgcgaaccgt ttgcggtggc gctggcggcg ctggaacgcg cgggcaaccg cctgggcgat  660
ccggtgctga tttgcggcgc gggcccgatt ggcctggtga ccctgctggc gagccatgcg  720
gcgggctgca ccccgattgt gattaccgat ctgcaggcga gccgcctgga agtggcgaaa  780
aaactgattc cgaccgtgaa aaccgtgcag attgaacgca gctggaccag caaagaaacc  840
agcgaagcga ttaaagaagc ggcgggcacc ggcattcgcg tggcgattga tgcgaccggc  900
tttgaaagca gcattaccgc ggcgatttat agcgtggtgt ttggcggcaa agtgtttgtg  960
attggcgcgg gcccgagcga acagaaatat ccgtttggct attgcagcgc gaacgaaatt  1020
gatctgcagt ttcagtatcg ctatgcgcat cagtatccga aagcgctgcg cattgtgagc  1080
ggcggcctga ttaacctgaa accgctgctg acccatacct ttccgctgaa caaagcggtg  1140
gaagcgtttc atgtggcggc ggatccgacc aaaggcgcga ttaaagtgca gattattgat  1200

SEQ ID NO: 64           moltype = AA  length = 400
FEATURE                 Location/Qualifiers
source                  1..400
                        mol_type = protein
                        organism = Cryptococcus neoformans
SEQUENCE: 64
MCSSHATAVE SVSPAPRKSQ YEVKYDPDLV LKSAEFKELK QGDKELEDPK ANLACAYDEK  60
HNVKMINKPI PKARQDEVVV HIKATGICGS DVHFWKHGQI GPTMIVTDTC GAGHESAGEV  120
VEVGPGVEQW KVGDRVAIEC GVPCGQASCG PCVTGRYNAC PQVVFFSTPP YHGTLTRYHA  180
HPASWLHRLP DNLSYEEGAL CEPFAVALAA LERAGNRLGD PVLICGAGPI GLVTLLASHA  240
AGCTPIVITD LQASRLEVAK KLIPTVKTVQ IERSWTSKET SEAIKEAAGT GIRVAIDATG  300
FESSITAAIY SVVFGGKVFV IGAGPSEQKY PFGYCSANEI DLQFQYRYAH QYPKALRIVS  360
GGLINLKPLL THTFPLNKAV EAFHVAADPT KGAIKVQIID                       400

SEQ ID NO: 65           moltype = DNA  length = 1689
FEATURE                 Location/Qualifiers
source                  1..1689
                        mol_type = genomic DNA
                        organism = Cryptococcus neoformans
CDS                     1..1689
SEQUENCE: 65
atggtgtgcg tgattagcga tccggattgg tggcgccagg cggtggtgta tcagatttat  60
ccgcgcagct ttgcggatgc gaacggcgat ggcattggcg atctgaaagg cattaccgcg  120
cgcgtgccgt atctgaaagc gctgggcgtg gatgcgattt ggctgagccc gttttatccg  180
agcgcgctgc gcgatggcgg ctatgatgtg gcggattatc gcgatgtgga tccgaaaatt  240
ggcaccctgg aagaatttga tgaaatgacc gcggcgtttc agaaagtggg cattcgcgtg  300
attgtggata ttgtgccgaa ccatagcagc gatgatcatg aatggtttca ggcggcgctg  360
aaagcgggca aaggcagccc ggaacgcgaa cgctatattt ttcgcgatgg cctgggcccg  420
aacaaagatc agccgccgac cgattggatt tgcagctttg gcggcagcgc gtggagcccg  480
agcggcatga acgatggcca gtggtatttt cattggtttg atagcagcca gccggattgg  540
aactgggaaa acccggatgt gaaagcggat tttctgaaaa ccctgaaatt ttggggcgat  600
cgcggcgtga gcggctttcg cattgatgtg gcgcatggcc tggcgaaaga tatgagcgaa  660
ccgctgccga actgggaaca gctgaccaaa ctgacccatc agaaactgac caacggcaac  720
agcgaactgg atcatccgct gctggatcgc aaagaagtgc atgatattta tcgcagctgg  780
cgcgaagtgt ttaaccagtt taacccgccg ctgatggcgg tggcggaagc gtgggtggcg  840
ccggatcaga aaccgctgta tgcgagcagc gaaggcctgg gccagacctt tagctttgat  900
attctgctgt gcaactttga tgcggaagaa tatcgccagt gcattaaaag cagcctggcg  960
ggcagcaaaa aaagcgatag caccaccacc tgggtgctga gcaaccatga tgtgatgcgc  1020
catccgaccc gctttggcct gccgaacgtg ccgaacgcga accatgcgat gaccaccgat  1080
acctataaca aatttctgaa aaccaaactg accgatccga aagtggatat tgaacagggc  1140
ctgcgccgcg cgaaagcggc gaccctgatg attctggcgc tgccgggcag cacctatctg  1200
tatcagggcg aagaactggg cctgcaggaa gtggtggaaa ttccggatga agaacgccag  1260
gatccgattt ttattcgcac caaaggcgaa gaagtgggcc gcgatggctg ccgcgtgccg  1320
attccgtggg tggcggatga aaaaaacttt ggctatggcc cgggcaaacg cgcgcatctg  1380
ccgcagccgg cgtggtttaa agattatgcg gtggatgtgg aagaaaaaga tgcgaacagc  1440
gtgctgagcc tgtatcgccg cgcgctgggc ctgcgcaaag gcctgcagag cgcggaagaa  1500
ctggaatggg tggaaaaccc gaacaaagaa gtgctgcatt ttcgccgccc gggcggctgg  1560
gaagtggtgg tgaacattgg caaagatagc gtggatctgc cgaaaggcag cgtgctgatt  1620
agcagcagca acaacgcgct gaaaggcggc agcattccgg gcgaaaccac cgtgtggctg  1680
aaaagcgcg                                                         1689

SEQ ID NO: 66           moltype = AA  length = 563
FEATURE                 Location/Qualifiers
source                  1..563
                        mol_type = protein
                        organism = Cryptococcus neoformans
SEQUENCE: 66
MVCVISDPDW WRQAVVYQIY PRSFADANGD GIGDLKGITA RVPYLKALGV DAIWLSPFYP  60
SALRDGGYDV ADYRDVDPKI GTLEEFDEMT AAFQKVGIRV IVDIVPNHSS DDHEWFQAAL  120
KAGKGSPERE RYIFRDGLGP NKDQPPTDWI CSFGGSAWSP SGMNDGQWYF HWFDSSQPDW  180
NWENPDVKAD FLKTLKFWGD RGVSGFRIDV AHGLAKDMSE PLPNWEQLTK LTHQKLTNGN  240
SELDHPLLDR KEVHDIYRSW REVFNQFNPP LMAVAEAWVA PDQKPLYASS EGLGQTFSFD  300
```

-continued

```
ILLCNFDAEE YRQCIKSSLA GSKKSDSTTT WVLSNHDVMR HPTRFGLPNV PNANHAMTTD  360
TYNKFLKTKL TDPKVDIEQG LRRAKAATLM ILALPGSTYL YQGEELGLQE VVEIPDEERQ  420
DPIFIRTKGE EVGRDGCRVP IPWVADEKNF GYGPGKRAHL PQPAWFKDYA VDVEEKDANS  480
VLSLYRRALG LRKGLQSAEE LEWVENPNKE VLHFRRPGGW EVVVNIGKDS VDLPKGSVLI  540
SSSNNALKGG SIPGETTVWL KSA                                          563

SEQ ID NO: 67          moltype = DNA  length = 729
FEATURE                Location/Qualifiers
source                 1..729
                       mol_type = genomic DNA
                       organism = Cryptococcus neoformans
CDS                    1..729
SEQUENCE: 67
atgccgagcg tggtgtttga tgtggtgggc acctgcttta gctatgataa cggcgcggaa  60
gcgctgcagg cgcgcctggg cccgaaactg gcgaaatatg gcattccgag caaactgctg  120
ttttatagct gggtgtgcag caccgaacgc gattatagct atctgagcca gattaaacag  180
tataaagcgt tttttgcgat tctgagcaac accctgaccc gcgtgctgtt tcaggcgggc  240
gtgccggtgg aagcgctgga tgattttttt accgcggatg atgtggatta tattatgaac  300
gaatataaaa aactgaaagc gcgcccgggc ctggcggaaa tgatgcagac cctgcgcgat  360
ggcggctttg aagtgtggtg ctgcagcgat gcgaacgtgg atcgcgtgaa aggctatttt  420
gataacgcgg gcgtggaaat gccgctggat catattctga gcgcggatat ggtgaaagcg  480
ggcaaaccgg aagcggcggt gtataaattt gcgcgcgaaa aagcgggcag cgatcagccg  540
ggcgaagtga gcgtgtttgc ggcgagccat gcgtgggatt gcgcggcggc gaaagcggcg  600
ggctttctga ccgcgtatac caccacctat gaatatgatg aatgcgaagt gatttttggc  660
aaaagcgatc tggtggcgcc ggatctggtg agcctgggca aaggcattgt ggaaaaatgg  720
ggcaaaaaa                                                          729

SEQ ID NO: 68          moltype = AA  length = 243
FEATURE                Location/Qualifiers
source                 1..243
                       mol_type = protein
                       organism = Cryptococcus neoformans
SEQUENCE: 68
MPSVVFDVVG TCFSYDNGAE ALQARLGPKL AKYGIPSKLL FYSWVCSTER DYSYLSQIKQ  60
YKAFFAILSN TLTRVLFQAG VPVEALDDFF TADDVDYIMN EYKKLKARPG LAEMMQTLRD  120
GGFEVWCCSD ANVDRVKGYF DNAGVEMPLD HILSADMVKA GKPEAAVYKF AREKAGSDQP  180
GEVSVFAASH AWDCAAAKAA GFLTAYTTTY EYDECEVIFG KSDLVAPDLV SLGKGIVEKW  240
GKK                                                                243
```

What is claimed is:

1. A method of treating fungal infections in mammals, the method comprising administering to the mammal a spore germination-inhibiting concentration of a compound, or salts thereof; wherein the compound is selected from the group consisting of:

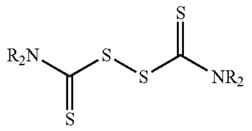

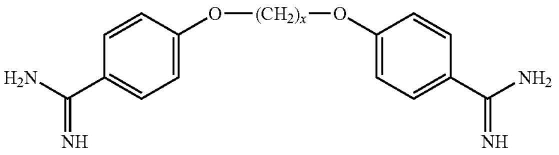

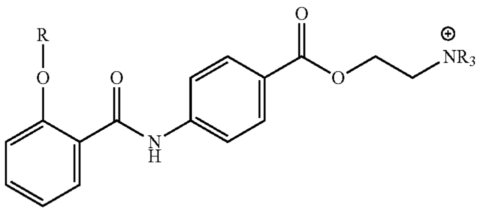

and

-continued

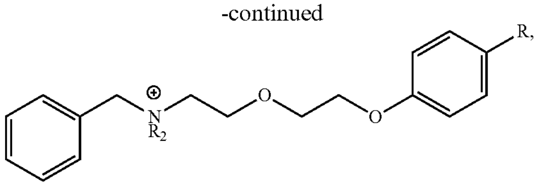

wherein R is linear or branched $C_{1-12}$ alkyl and "x" is an integer of from 1 to 12; and wherein the compound inhibits germination of fungal spores in vivo.

2. The method of claim 1, wherein the compound is:

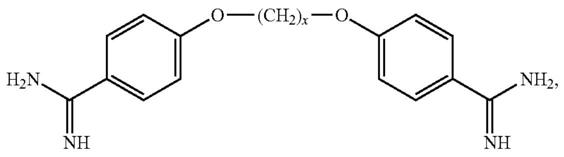

wherein "x" is an integer of from 1 to 12.

3. The method of claim 1, wherein the fungal infection is caused by a spore-producing fungus of a genus selected from the group consisting of *Histoplasma, Blastomyces, Aspergillus, Coccidioides, Sporothrix, Penicillium*, and *Cryptococcus*.

4. The method of claim 3, wherein the spore-producing fungus is a species selected from the group consisting of *Histoplasma capsulatum, Blastomyces dermatitidis, Asper-*

*gillus fumigatus, Coccidioides immitis, Sporothrix schenkii, Penicillium marneffei*, and *Cryptococcus neoformans*.

5. The method of claim 1, wherein administration of the compound to the mammal inhibits fungal spore germination in vivo by at least 70% relative to an untreated control.

* * * * *